(12) United States Patent
Chin et al.

(10) Patent No.: US 9,968,690 B2
(45) Date of Patent: May 15, 2018

(54) NORBORNENE MODIFIED PEPTIDES AND THEIR LABELLING WITH TETRAZINE COMPOUNDS

(71) Applicants: MEDICAL RESEARCH COUNCIL, Wiltshire (GB); NORTH CAROLINA STATE UNIVERSITY, Raleigh, NC (US)

(72) Inventors: Jason Chin, Cambridgeshire (GB); Alexander Deiters, Raleigh, NC (US); Kathrin Lang, Cambridge (GB)

(73) Assignees: Medical Research Council, Wiltshire (GB); North Carolina State University, Raleigh, NC (US)

( * ) Notice: Subject to any disclaimer, the term of this patent is extended or adjusted under 35 U.S.C. 154(b) by 245 days.

(21) Appl. No.: 14/373,292

(22) PCT Filed: Jan. 21, 2013

(86) PCT No.: PCT/GB2013/050121
§ 371 (c)(1),
(2) Date: Jul. 18, 2014

(87) PCT Pub. No.: WO2013/108044
PCT Pub. Date: Jul. 25, 2013

(65) Prior Publication Data
US 2015/0005481 A1 Jan. 1, 2015

Related U.S. Application Data

(60) Provisional application No. 61/588,948, filed on Jan. 20, 2012.

(30) Foreign Application Priority Data

Jan. 20, 2012 (GB) .................................. 1201100.3

(51) Int. Cl.
C07K 1/13 (2006.01)
C07K 7/64 (2006.01)
A61K 38/00 (2006.01)
A61K 49/00 (2006.01)
C12P 21/02 (2006.01)
C07C 271/34 (2006.01)
C12N 9/00 (2006.01)
G01N 33/58 (2006.01)

(52) U.S. Cl.
CPC ........ *A61K 49/0017* (2013.01); *C07C 271/34* (2013.01); *C07K 1/13* (2013.01); *C12N 9/93* (2013.01); *C12P 21/02* (2013.01); *C12Y 601/01026* (2013.01); *G01N 33/582* (2013.01); *C07C 2601/16* (2017.05); *C07C 2602/42* (2017.05)

(58) Field of Classification Search
CPC . C07K 1/13; C07K 7/64; C07K 9/003; A61K 38/00; A61K 49/0017; C12Y 601/01026; G01N 33/582
See application file for complete search history.

(56) References Cited

FOREIGN PATENT DOCUMENTS

| WO | 2010139948 | 12/2010 |
| WO | 2011156686 | 12/2011 |
| WO | 2012104422 | 8/2012 |

OTHER PUBLICATIONS

Devaraj NK et al, Tetrazine-based cycloadditions: application to pretargeted live cell imaging. Bioconjug. Chem. 2008, 19, 2297-2299.*
Schleifenbaum, A. "International Search Report—International Application No. PCT/GB2013/050121" European Patent Office; dated Oct. 9, 2013; pp. 1-10.
Sletten, Ellen M., et al. "Bioorthogonal Chemistry: Fishing for Selectivity in a Sea of Functionality" Angew. Chem. Int. Ed. 2009, 48, pp. 6974-6998.
Kaya, Emine, et al. "A Genetically Encoded Norbornene Amino Acid for the Mild and Selective Modification of Proteins in a Copper-Free Click Reaction" Angew. Chem. Int. Ed. 2012, 571, pp. 4466-4469.
Bianco, Ambra, et al. "Expanding the genetic code of *Drosophila melanogaster*" Nature Chemical Biology; vol. 8; Sep. 2012; pp. 748-750.
Plass, Tilman, et al. "Amino Acids for Diels-Alder Reactions in Living Cells" Angew. Chem. Int. Ed. 2012, 51, pp. 4166-4170.
Lang, Kathrin, et al. "Genetic Encoding of Bicyclononynes and trans-Cyclooctenes for Site-Specific Protein Labeling in Vitro and in Live Mammalian Cells via Rapid Fluorogenic Diels-Alder Reactions" J. Am. Chem. Soc. 2012, 134, pp. 10317-10320.
Lang, Kathrin, et al. "Genetically encoded norbornene directs site-specific cellular protein labelling via a rapid bioorthogonal reaction" Nature Chemistry; vol. 4; Apr. 2012; pp. 298-304.
Devaraj, Neal K., et al. "Tetrazine-Based Cycloadditions: Application to Pretargeted Live Cell Imaging" Bioconjugate Chem. 2008, 19; pp. 2297-2299.
Zeglis, Brian M., et al. "Modular Strategy for the Construction of Radiometalated Antibodies for Positron Emission Tomography Based on Inverse Electron Demand Diels-Alder Click Chemistry" Bioconjugate Chem. 2011, 22, pp. 2048-2059.
Barker, Ian A., et al. "Tetrazine-Norbornene Click Reactions to Functionalize Degradable Polymers Derived from Lactide" Macromol. Rapid Commun. 2011, 32, pp. 1362-1366.

* cited by examiner

*Primary Examiner* — Kagnew H Gebreyesus
(74) *Attorney, Agent, or Firm* — Thomas G. Peterson; Bradley Arant Boult Cummings LLP

(57) ABSTRACT

The invention relates to a polypeptide comprising an amino acid having a norbornene group. Suitably said norbornene group is present as an amino acid residue of a norbornene lysine. The invention also relates to a method of producing a polypeptide comprising a norbornene group, said method comprising genetically incorporating an amino acid comprising a norbornene group into a polypeptide.

9 Claims, 37 Drawing Sheets

9: X = CH, R = TAMRA-X
10: X = N, R = TAMRA-X
11: X = CH, R = Bodipy TMR-X

12: R = TAMRA-X
13: R = Bodipy-FL
14: R = fluorescein

FIG. 4A
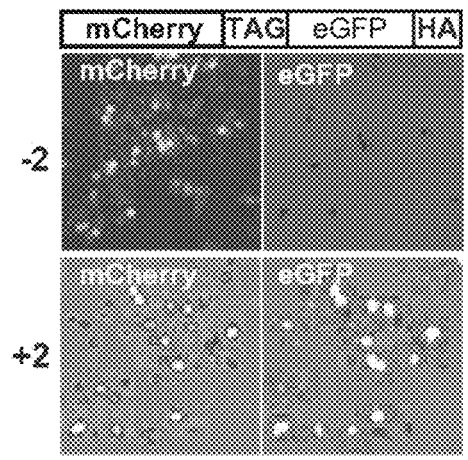
FIG. 4B
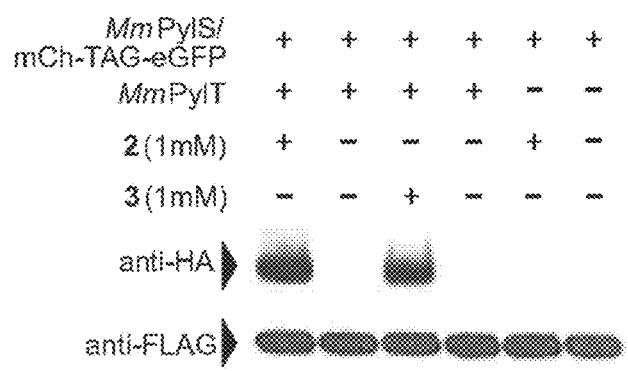
FIG. 4C
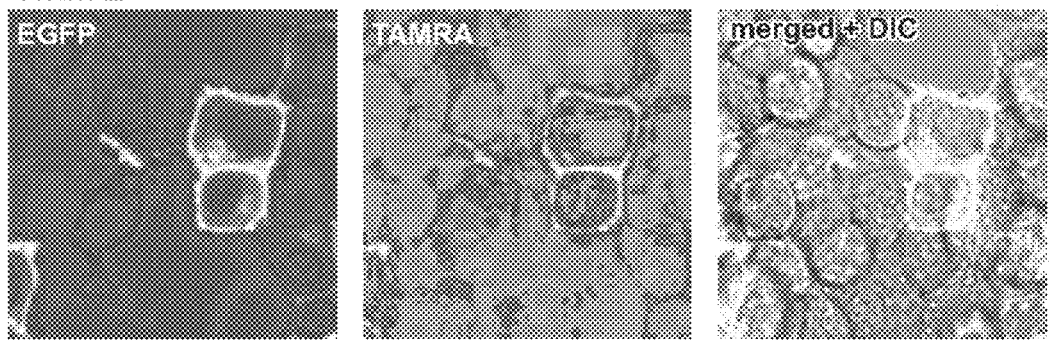
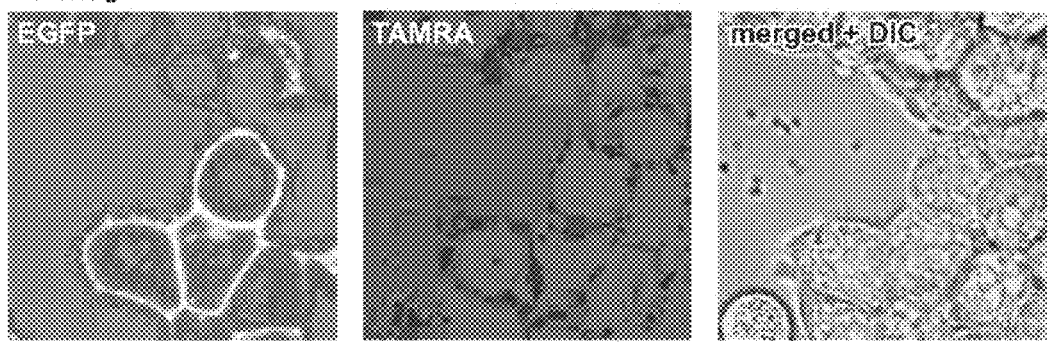

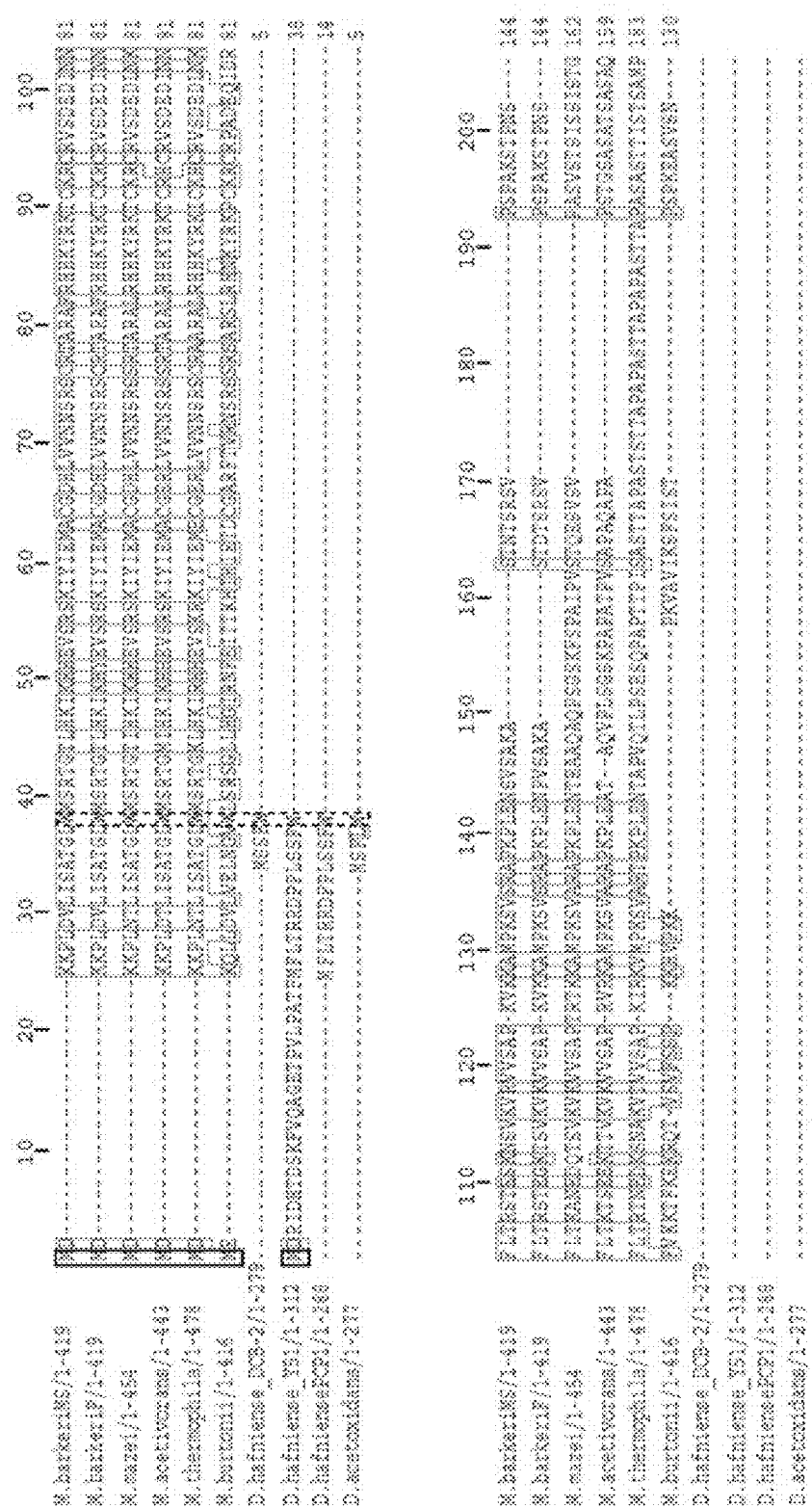
FIG. 5: Alignment of PylS sequences

FIG. 5 (continued)
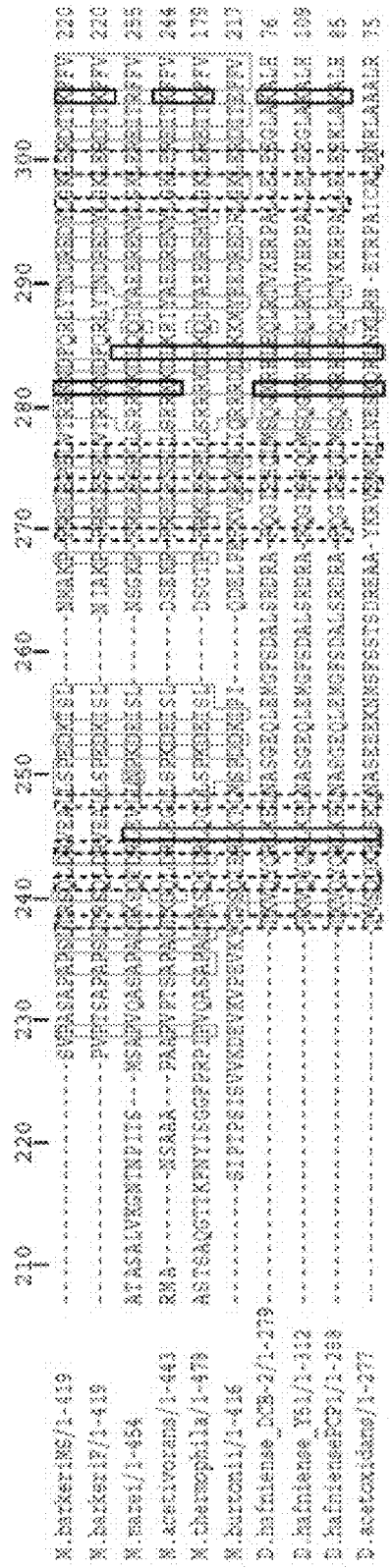
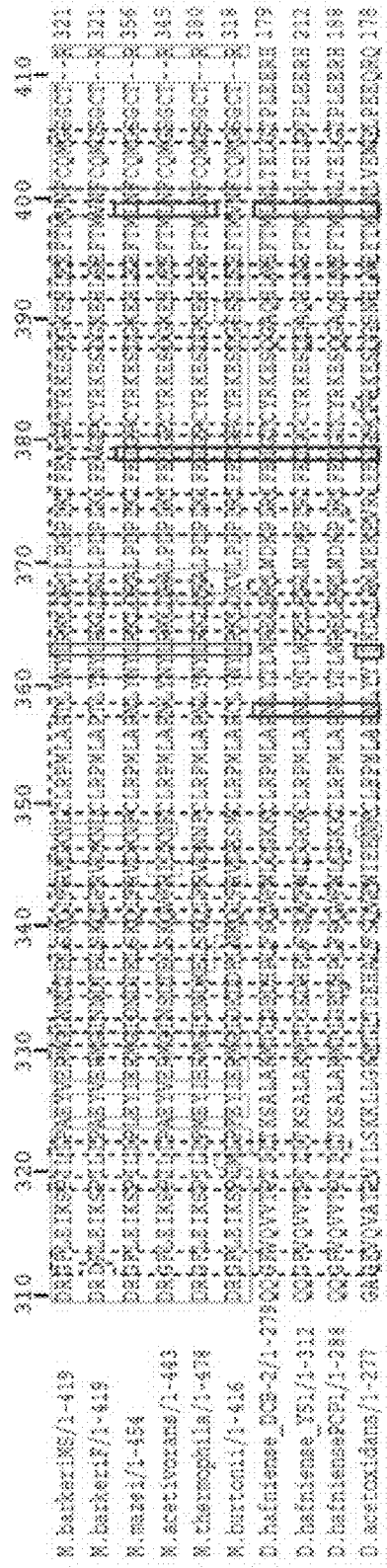

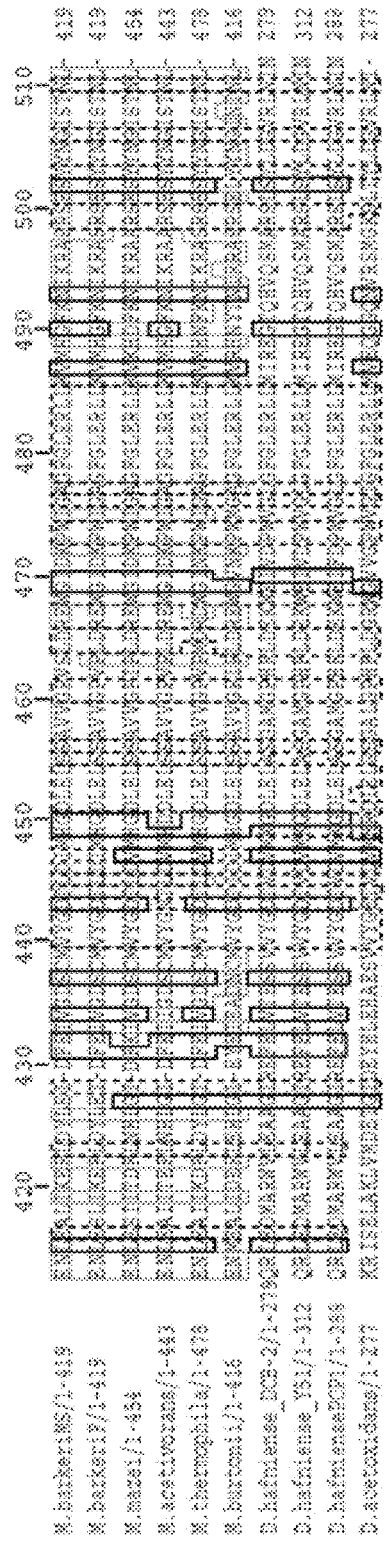
FIG. 5 (continued)
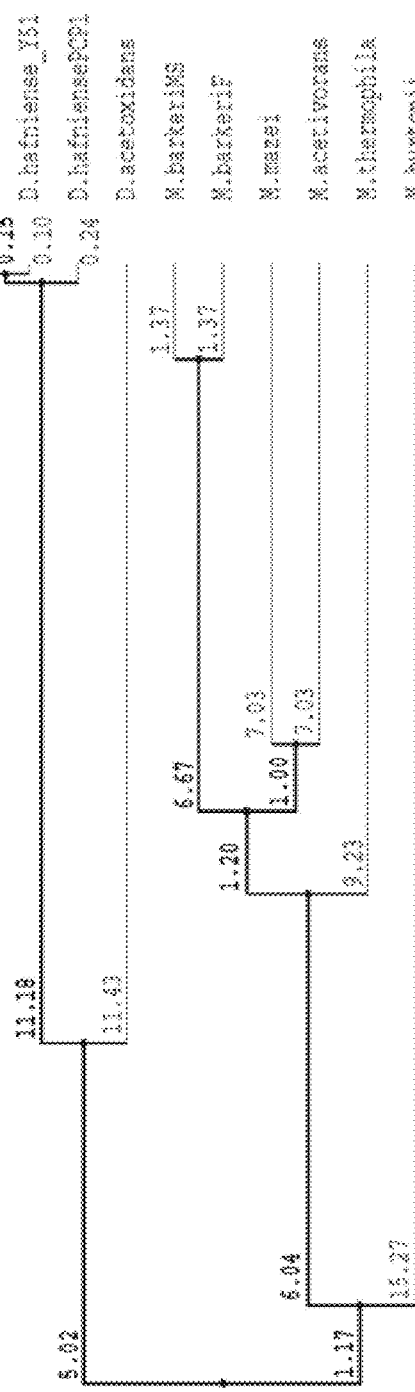
FIG. 6: Sequence identity of PylS sequences FIG. 7: Alignment of the catalytic domain of PylS seqeunces (from 350 to 480; numbering from alignment of FIG. 5)

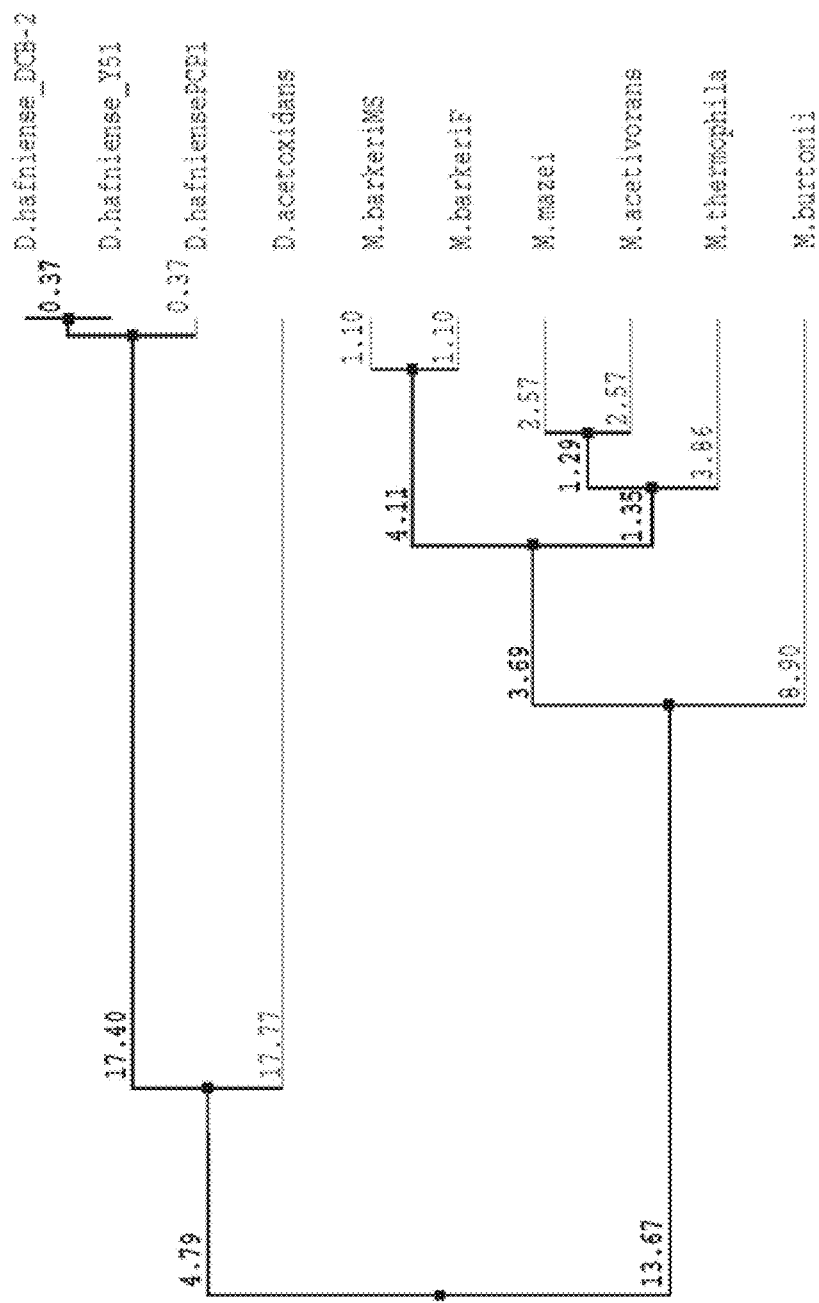
FIG. 8: Sequence identity of the catalytic domains of PylS sequences

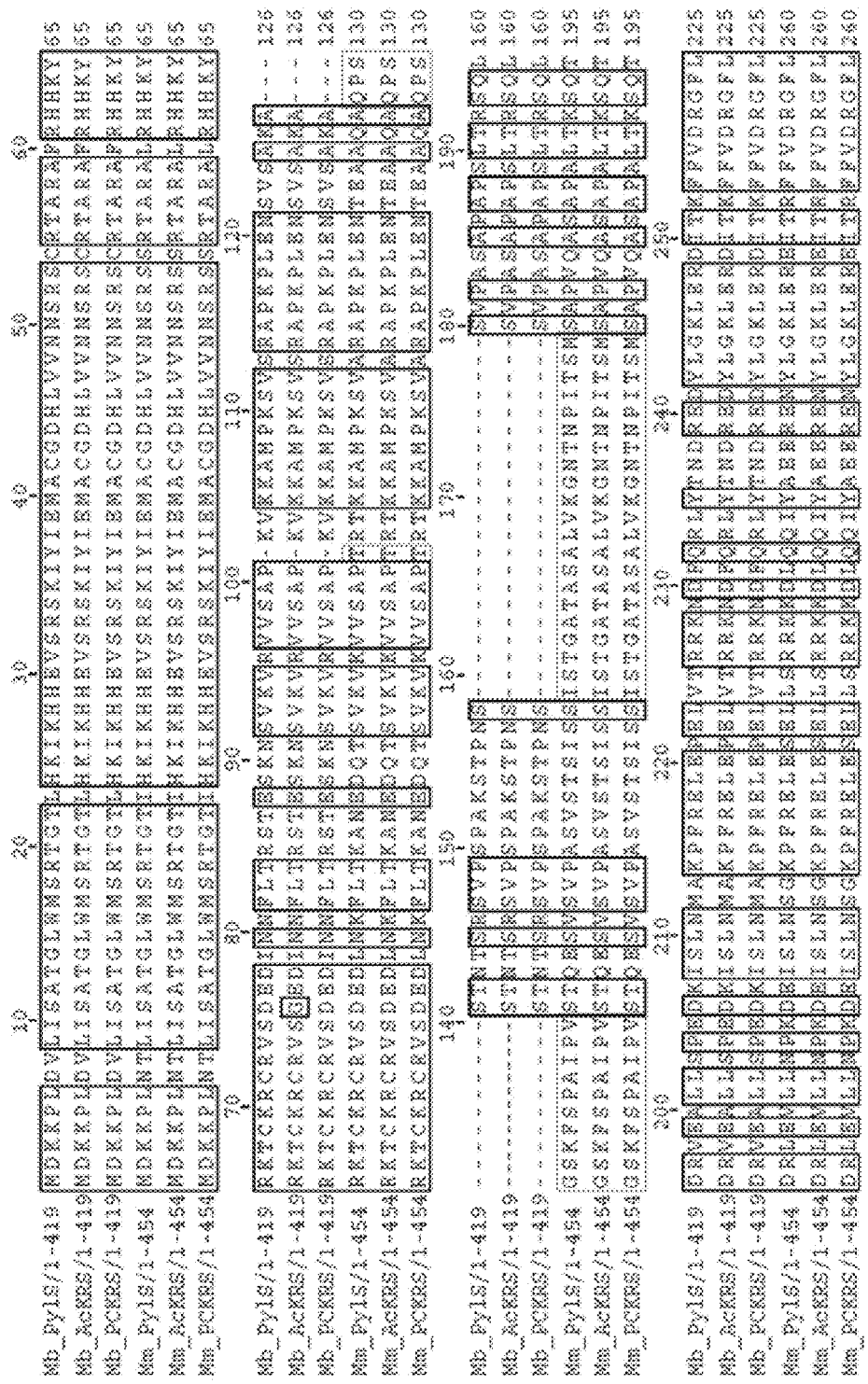
FIG. 9: Alignment of synthetases with transplanted mutations based on *M.barkeri* PylS or *M.mazwi* PylS

| Reaction | Advantages | Applications | Limitations |
|---|---|---|---|
| A. Tetrazine inverse-electron-demand Diels-Alder reaction | highest reaction rates in water, high selectivity, high yields, wide tolerance of functional groups | Genetic encoded in bacterial and mammalian cells followed by protein labelling using fluorescent turn-on probes based on tetrazines | synthesis of (e.g.) tetrazines for reaction with norbornene group |
| B. Oxime and hydrazone ligation | the carbonyl group is absent in proteins | Phe-derived ketones for the labeling of cells with hydrazide-modified fluorophores: cascade blue, Alexa568 and Alexa647; Ser-modified aldehydes linked to hydrazide-biotin and aminooxy-PEG at the N-terminus of proteins | slightly acidic pH and high concentration of reagents (2-5 mM), competition with intracellular electrophiles, e.g., from glucose and pyruvate |
| C. Copper-catalyzed azide-alkyne cycloaddition | small size, inert towards native biomolecules, fast kinetics, reaction partners are easily synthesized | unnatural amino acids with alkyne or azide moieties have been used in proteins to PEGylate, biotinilate, glycosylate, fluorescent label and cross-link proteins | copper cytotoxicity, slow reaction |
| D. Strain-promoted azide-alkyne cycloaddition | absence of toxic copper | biotin labeling of azides within cell-surface glycans, imaging of azide-containing biomolecules in live cells, C. elegans and zebrafish embryo, DNA ligation | demanding synthesis for cyclooctyne derivatives, possible background labeling, slow reaction, low yields in a cellular environment |
| E. Staudinger ligation | phosphine and azide are absent in proteins, inert to native biomolecules, react with each other readily under | addition of new moieties to proteins, FRET imaging of live cells with fluorescent phosphine reagent, cell-surface labeling of cells, site selective protein immobilization | non-specific oxidation of phosphines by air or metabolic enzymes, slow ligation reaction, phosphine-disulfide |

FIG. 12 (continued)

| | | physiological conditions | | bond interactions |
|---|---|---|---|---|
| F. Diels-Alder reaction | | inert and compatible to the biological system, high selectivity, accelerated in aqueous media, high yields | modification of oligonucleotides, ligation of peptides and proteins, site-specific modification of streptavidin or Rab proteins, fluorescent labeling CAL-B lipase | relatively slow, slightly acidic pH, low yields |
| G. Tetrazole-alkene photoinduced cycloaddition | | wide tolerance of functional groups, compatible to aqueous environments, fluorescent cycloadduct | in vitro and in vivo fluorescent labeling and PEGylation of Z-domain protein charged with O-allyltyrosine | requires deactivated alkenes for fast reaction rates, cell damage by low-wavelength irradiation, low yields |
| H. Ruthenium-catalyzed olefin cross-metathesis | | enables the installation of a C-C bond, inert to a range of biological processes | applications with cysteine (S-allylcysteine) have been explored: PEGylation, glycosylation | restricted to allyl sulfides, decomposition of catalyst by air, low yields, low rates |
| I. Thiol-ene reaction | | can proceed at wavelengths ($\lambda$=365–405 nm) close to visible light and in aqueous environments | coupling between amino acids and peptides, alkylation of cysteines, fluorescent markers | competition with other thiols, unknown reactivity of substrates |
| J. Palladium-catalyzed cross-coupling reaction | | broad functional group tolerance | Heck and Sonogashira biotinylation of iodophenylalanine-encoded Rnx protein, biotin labeling of p-bromophenylalanine-Z-domain protein | high catalyst loading, high temperatures, slightly basic pH, low yields, low reaction rate |

● = label   ▓ = biomolecule

FIG. 15A
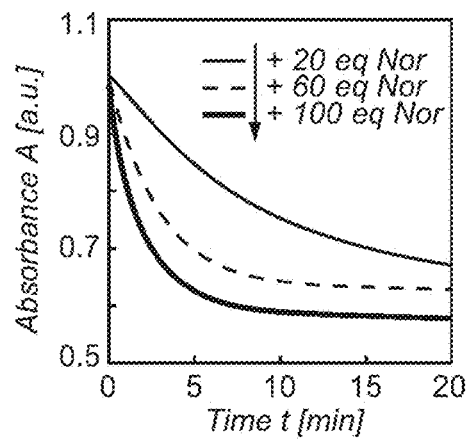
FIG. 15B
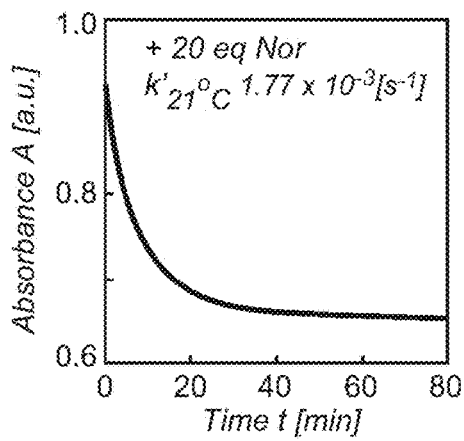
FIG. 15C
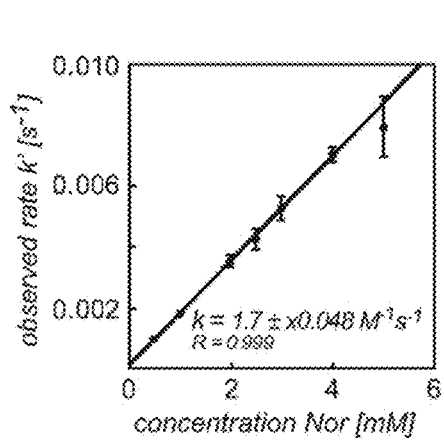
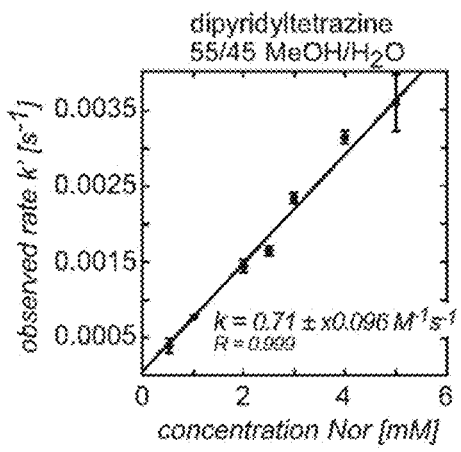
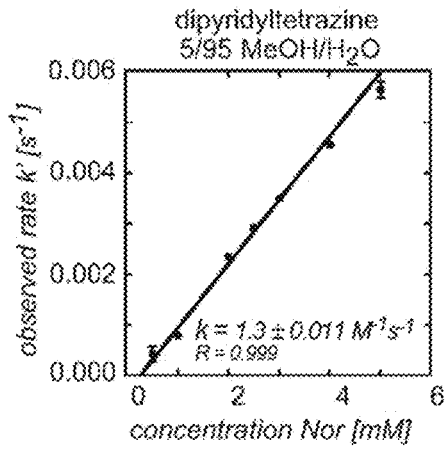
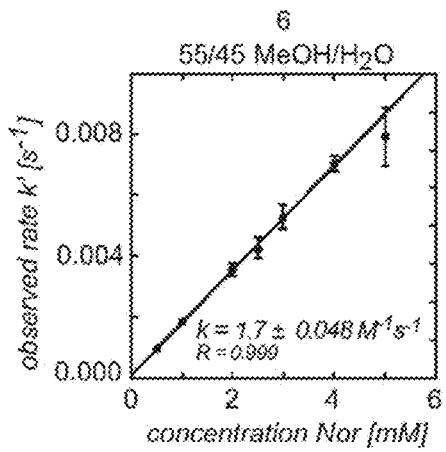

FIG. 16A

| Tetrazine | $k_2 [M^{-1}s^{-1}]^a$ | $k_2 [M^{-1}s^{-1}]^b$ |
|---|---|---|
| 5 | 0.47 ± 0.0069 | 0.94 ± 0.0079 |
| 6 | 1.70 ± 0.048 | 3.41 ± 0.066 |
| 7 | 0.15 | n.d |
| 8 | 5.00 ± 0.096 | 9.46 ± 0.16 |
| 3,6-dipyridyltetrazine | 0.71 ± 0.019 | 1.30 ± 0.011 |

FIG. 16B

| Tetrazine -fluorophore | formula | Mass calculated for $[M+H]^+$ | Mass found for $[M+H]^+$ |
|---|---|---|---|
| 9 (Tet1-TAMRA-X) | $C_{45}H_{43}N_{11}O_6$ | 834.34 | 834.5 |
| 10 (Tet2-TAMRA-X) | $C_{44}H_{42}N_{12}O_6$ | 835.35 | 836.0 |
| 11 (Tet1-Bodipy-TMR-X) | $C_{41}H_{42}BF_2N_{11}O_4$ | 802.65 | 802.8 |
| 12 (Tet4-TAMRA-X) | $C_{45}H_{44}N_{12}O_6$ | 849.35 | 849.5 |
| 13 (Tet4-Bodipy-FL) | $C_{28}H_{26}BF_2N_{11}O_2$ | 598.39 | 598.5 |
| 14 (Tet4-fluorescein) | $C_{35}H_{24}N_{10}O_6S$ | 713.69 | 713.3 |

FIG. 17
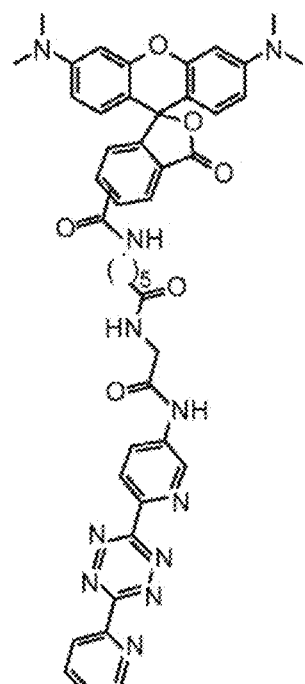
9 (5-TAMRA-X)
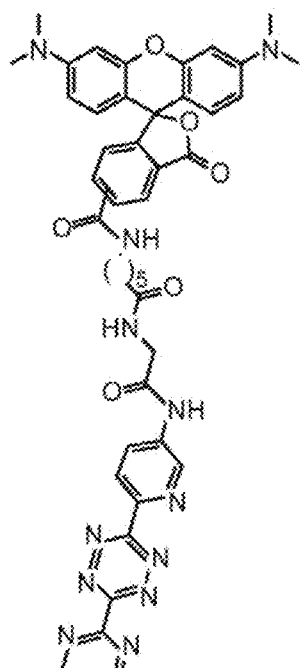
10 (6-TAMRA-X)
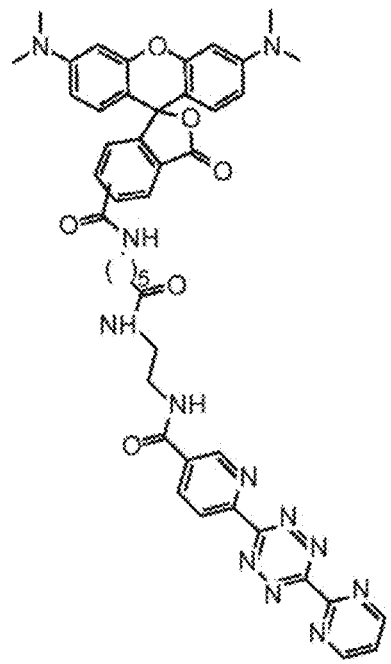
12 (8-TAMRA-X)
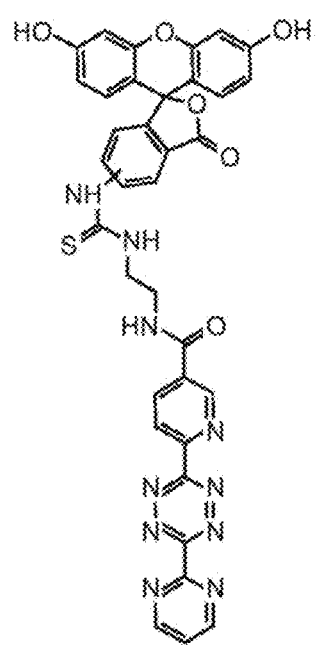
14 (8-fluorescein)

FIG. 22
sf-GFP-2 + 20 eq 12
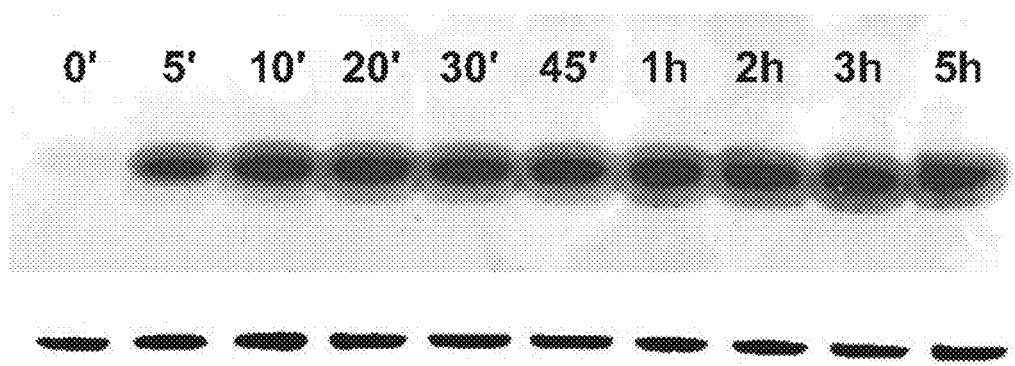
sf-GFP-2 + 20 eq 9
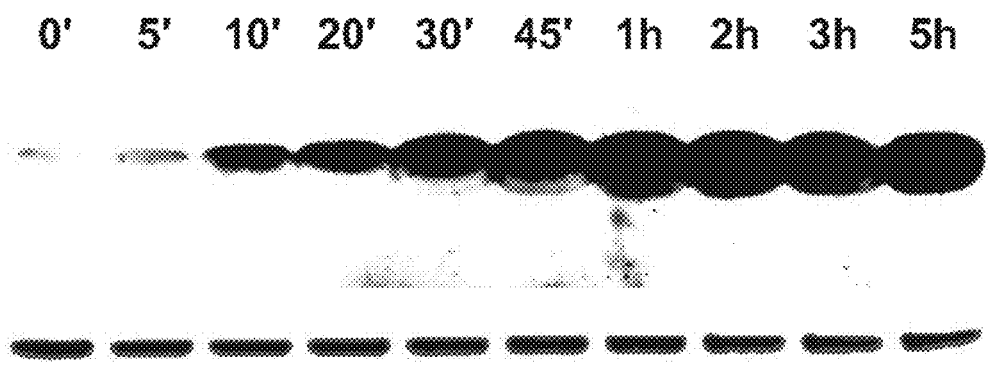

2hs labeling with tetrazine-dye conjugate 9

1nM 2

FIG. 25
4hs labeling with tetrazine-dye conjugate 9
1nM 2
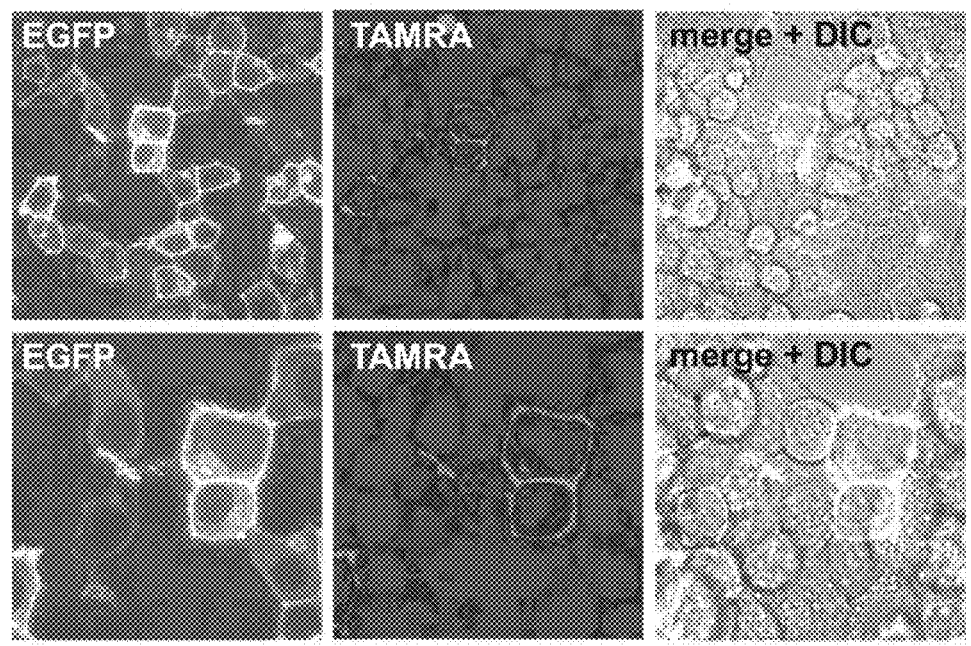
1nM 3
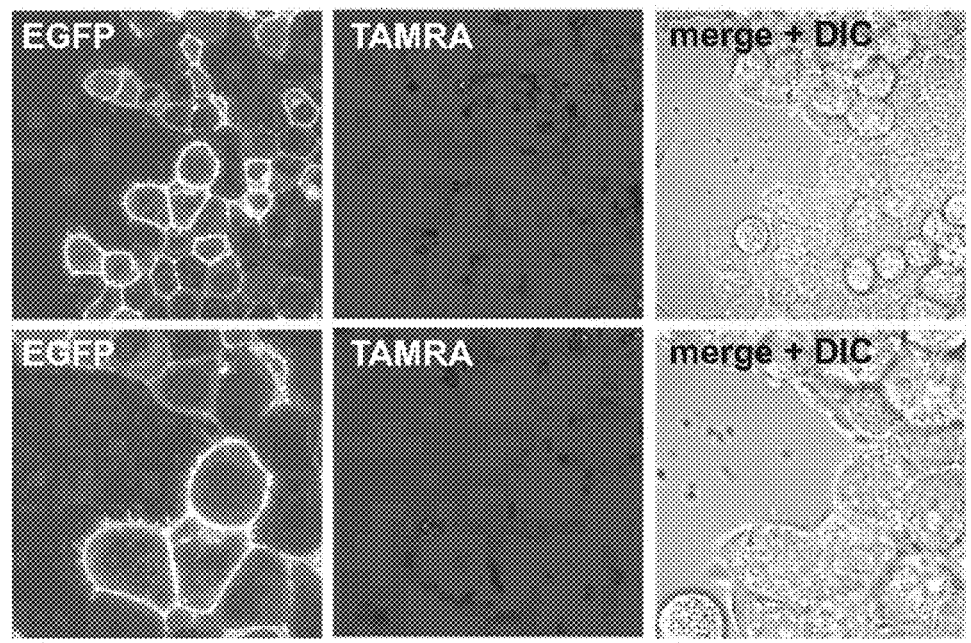

FIG. 26
8hs labeling with tetrazine-dye conjugate 9
1nM 2
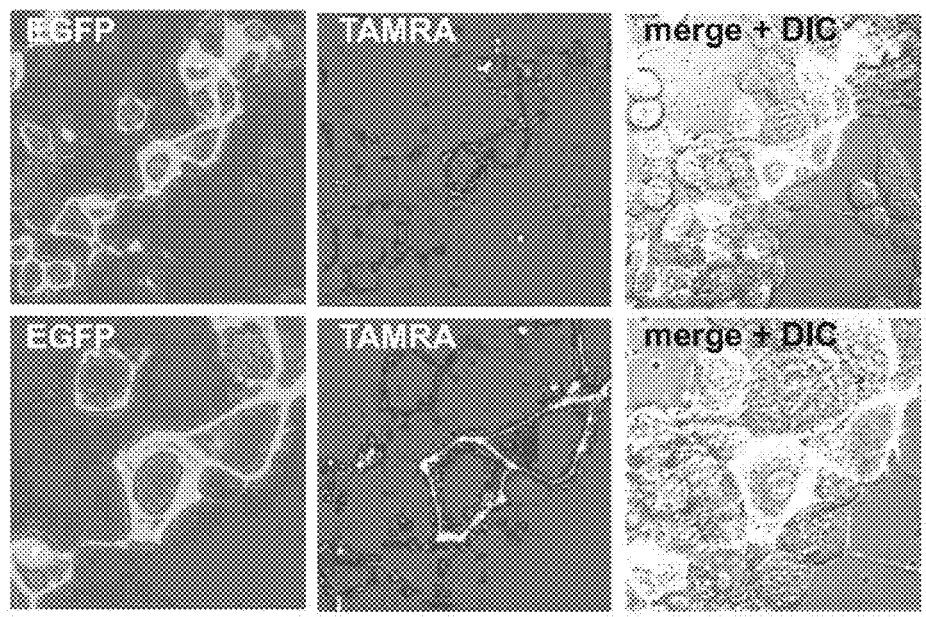
1nM 3
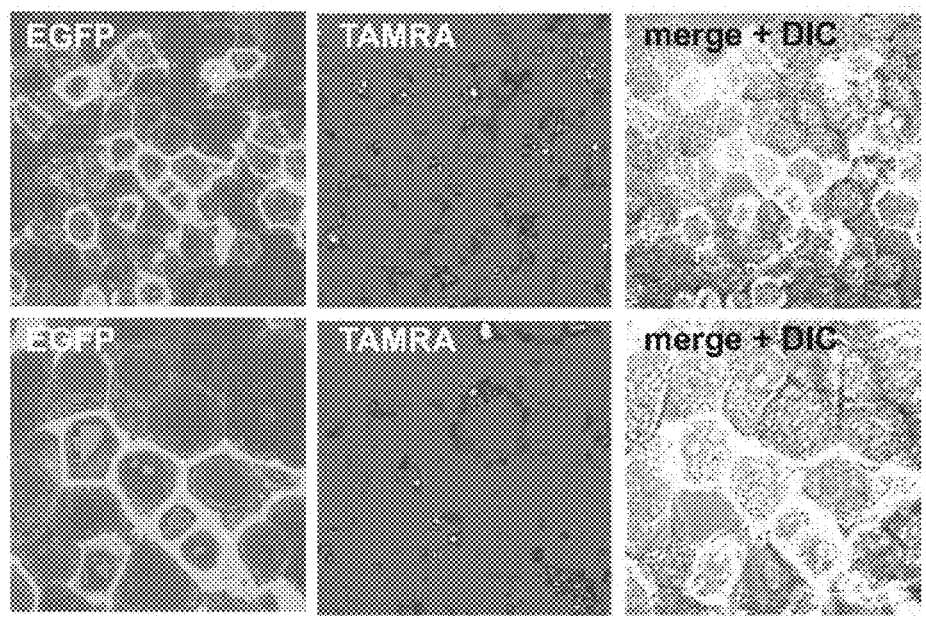

FIG. 27
16hs labeling with tetrazine-dye conjugate 9
1nM 2
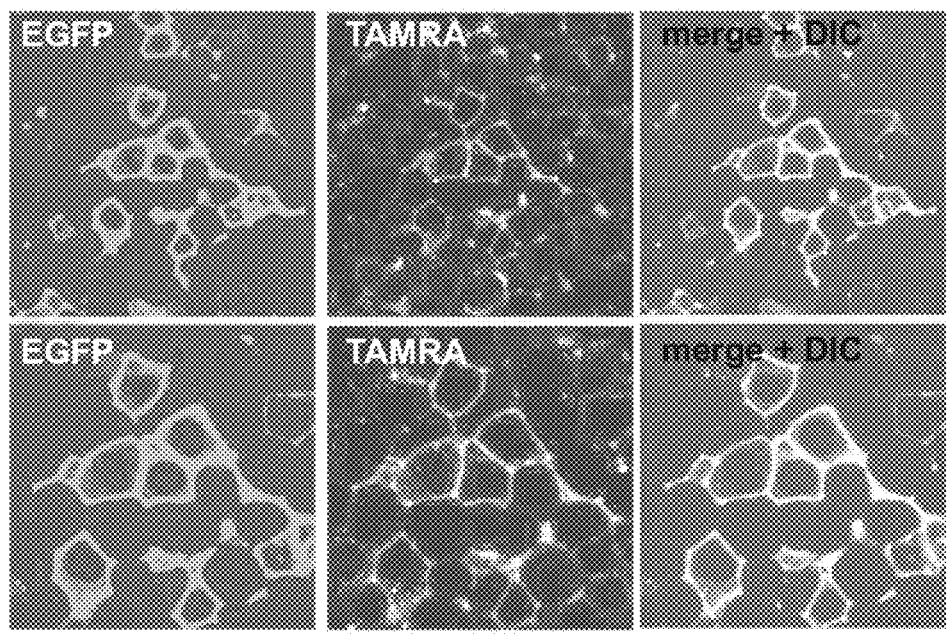
1nM 3
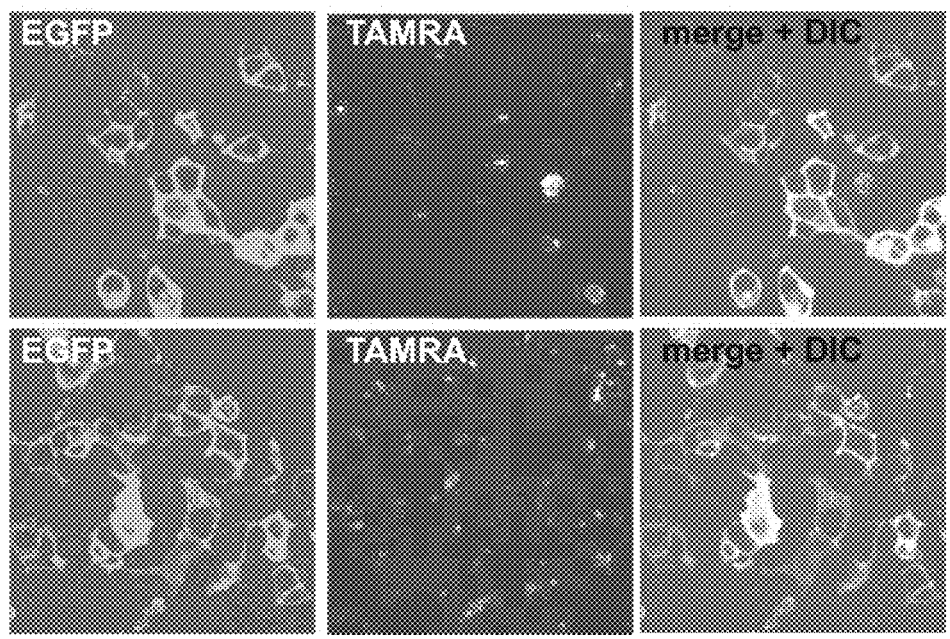

16hs labeling with DiBO-TAMRA dye
1nM 4

TAMRA imaged at higher contrast

16hs labeling with DiBO-TAMRA dye
1nM 4

US 9,968,690 B2

NORBORNENE MODIFIED PEPTIDES AND THEIR LABELLING WITH TETRAZINE COMPOUNDS

CROSS-REFERENCE TO RELATED APPLICATIONS

This application is a national stage under 35 U.S.C. 371 of International Application PCT/GB2013/050121, filed on Jan. 21, 2013 (currently pending). International Application PCT/GB2013/050121 cites the priority of U.S. provisional patent application No. 61/588,948 filed Jan. 20, 2012. International Application PCT/GB2013/050121 also cites the priority of British Patent Application 1201100.3, filed Jan. 20, 2012 (expired).

FIELD OF THE INVENTION

The invention relates to site-specific incorporation of bio-orthogonal groups via the (expanded) genetic code. In particular the invention relates to incorporation of a norbornene group into polypeptide.

BACKGROUND TO THE INVENTION

The site-specific incorporation of bio-orthogonal groups via genetic code expansion provides a powerful general strategy for site specifically labeling proteins with any probe. However, the slow reactivity of the bio-orthogonal functional groups that can be genetically encoded has limited this strategy's utility.

There is a pressing need for general methods to site-specifically label proteins, in diverse contexts, with user-defined probes.

Current protein labeling methods involve the use of fluorescent protein fusions, 1-4 self-labeling proteins (e.g., SNAPtag, HALOtag, CLIPtag),[5-8] ligases (e.g., biotin ligase, lipolic acid ligase, sortase, and phosphopantetheinyl-transferase)[9-15] and self-labeling tags (e.g., tetracysteine and tetraserine) [16,17] While some of these approaches allow rapid labeling and have had substantial impact on biological studies, they require the use of protein fusions and/or the introduction of additional sequences into the protein of interest. This can disturb the structure and function of the protein and make it challenging to place probes at any position in a protein.

Moreover, the range of probes that can be incorporated by some of these methods is limited.[3,4,18].

Ideal methods for protein labeling would i) allow probes to be easily placed at any position in a protein in diverse cells, ii) be rapid and quantitative, iii) be specific for a user-defined site in a protein, iv) show .'turn on.' fluorescence, with minimal off-site or background labeling, and v) allow for labeling with diverse probes. In principle, the genetically encoded, site specific incorporation of unnatural amino acids bearing bioorthogonal functional groups would allow the labeling of specific proteins at defined sites with essentially any probe.

Bio-orthogonal groups, including azides, alkynes, ketones, anilines, alkenes, tetrazoles, and [1,2] aminothiols have been genetically encoded using amber suppressor aminoacyl tRNA synthetase/tRNACUA pairs.[19-29] For established reactions that have been demonstrated on proteins the rate constants for the corresponding model reactions[30] are in the range of $10{-}2\ M{-}1\ s{-}1$ to $10{-}4\ M{-}1\ s{-}1$ (although for emerging approaches higher rates have been reported).[29,31,32]

The rates of established reactions are clearly sufficient to allow useful labeling of metabolically incorporated azido- and keto-bearing glycan analogs presented at high density on the cell surface, and the labeling of amino acid analogs incorporated throughout the proteome.[33-35] However the sluggishness of established bio-orthogonal reactions often makes it challenging to quantitatively label proteins at defined sites in vitro, and may account for the fact that there are currently no examples of labeling proteins expressed on the mammalian cell surface using genetically encoded unnatural amino acids.

The present invention seeks to overcome problem(s) associated with the prior art.

SUMMARY OF THE INVENTION

Recent advances in bio-orthogonal chemistry have demonstrated that strained alkenes, including norbornenes and trans-cyclooctenes, react rapidly and specifically with tetrazines in a reverse electron demand Diels Alder cycloaddition to form stable adducts with rate constants orders of magnitude faster than established bio-orthogonal reactions.[36-38] The present inventors have produced a system, including methods and novel reagents, for genetically encoding a component of these reactions. This provides an effective strategy for realizing rapid site-specific protein labeling.

More specifically, we demonstrate the genetic encoding of a norbornene amino acid using the pyrrolysyl-tRNA synthetase/tRNACUA pair in E. coli and mammalian cells. We provide a series of tetrazine-based probes that exhibit "turn-on" fluorescence upon their rapid reaction with norbornenes. We demonstrate that the labeling of an encoded norbornene is specific with respect to an entire proteome and thousands of times faster than established encodable bio-orthogonal reactions. We explicitly show the advantages of this approach over state of the art bioorthogonal reactions for protein labeling in vitro and on mammalian cells, demonstrating the first bio-orthogonal site specific labeling of a protein on the mammalian cell surface.

We further teach that genetically encoded norbornene directs site-specific protein labeling on the surface of mammalian cells via a rapid bio-orthogonal cycloaddition.

DETAILED DESCRIPTION OF THE INVENTION

In one aspect the invention provides a polypeptide comprising an amino acid having a norbornene group. The incorporation of a norbornene group has numerous advantages which are described and demonstrated herein.

Suitably norbornene group is present as an amino acid residue of a norbornene lysine.

In one embodiment the invention provides a polypeptide comprising a single amino acid having a norbornene group. Having only a single amino acid bearing a norbornene group provides a precisely defined polypeptide product. Having only a single amino acid bearing a norbornene group avoids problems of multiple labelling or incomplete labelling (if a reaction does not go to completion, heterogeneous products can result which can be a problem which is usefully addressed by having only a single amino acid bearing a norbornene group). In a preferred embodiment said norbornene group is present as an amino acid residue of a norbornene lysine. Preferably said single amino acid is not the N-terminal amino acid. Preferably the N-terminal amino group does not comprise norbornene. Preferably the amino acid residue bearing the norbornene is an internal amino acid of the polypeptide.

In another aspect, the invention relates to a method of producing a polypeptide comprising a norbornene group, said method comprising genetically incorporating an amino acid comprising a norbornene group into a polypeptide. Genetically incorporating the norbornene group allows precise construction of a defined polypeptide. The location of the norbornene group can be precisely controlled. This advantageously avoids the need to subject the whole polypeptide to complex reaction steps for addition of the norbornene group.

Suitably the method described for producing the polypeptide comprises (i) providing a nucleic acid encoding the polypeptide which nucleic acid comprises an orthogonal codon encoding the amino acid having a norbornene group;

(ii) translating said nucleic acid in the presence of an orthogonal tRNA synthetase/tRNA pair capable of recognising said orthogonal codon and incorporating said amino acid having a norbornene group into the polypeptide chain.

Suitably said orthogonal codon comprises an amber codon (TAG), said tRNA comprises MbtRNA$_{CUA}$ and said tRNA synthetase comprises MbPylRS.

Suitably said amino acid comprising a norbornene group is a norbornene lysine.

Suitably said amino acid is Nε-5-norbornene-2-yloxycarbonyl-L-lysine.

Suitably said amino acid having a norbornene group is incorporated at a position corresponding to a lysine residue in the wild type polypeptide. This has the advantage of maintaining the closest possible structural relationship of the norbornene containing polypeptide to the wild type polypeptide from which it is derived.

Suitably the polypeptide comprises a single norbornene group. This has the advantage of maintaining specificity for any further chemical modifications which might be directed at the norbornene group. For example when there is only a single norbornene group in the polypeptide of interest then possible issues of partial modification (e.g. where only a subset of norbornene groups in the polypeptide are subsequently modified), or issues of reaction microenvironments varying between alternate norbornene groups in the same polypeptides (which could lead to unequal reactivity between different norbornene group(s) at different locations in the polypeptide) are advantageously avoided. Suitably the polypeptide comprises a single norbornene amino acid residue.

A key advantage of incorporation of norbornene group is that is permits a range of extremely useful further compounds such as labels to be easily and specifically attached to the norbornene group.

Suitably said norbornene group is joined to a tetrazine group.

Suitably said tetrazine group is further joined to a fluorophore.

Suitably said tetrazine group is further joined to a PEG group.

Suitably said fluorophore comprises fluorescein, tetramethyl rhodamine (TAMRA) or boron-dipyrromethene (BODIPY).

In another aspect, the invention relates to a novel unnatural amino acid comprising a norbornene group, such as Nε-5-norbornene-2-yloxycarbonyl-L-lysine.

Suitably Nε-5-norbornene-2-yloxycarbonyl-L-lysine corresponds to formula 2:

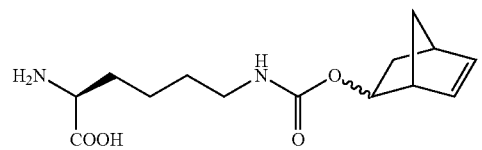 [SMILES: N[C@@H](CCCCNC(=O)OC1CC2C=CC1C2)C(=O)O]

In another aspect, the invention relates to a tetrazine compound joined to a fluorophore.

In another aspect, the invention relates to a tetrazine compound joined to a polyethylene glycol (PEG) group.

Suitably said tetrazine is selected from the group consisting of 5, 6, 7 or 8 of FIG. 10.

Suitably said fluorophore comprises fluorescein, tetramethyl rhodamine (TAMRA) or boron-dipyrromethene (BODIPY).

Suitably said tetrazine compound joined to a fluorophore is selected from the group consisting of 9, 10, 11, 12, 13 or 14 of FIG. 1C.

In another aspect, the invention relates to a method of producing a polypeptide comprising a tetrazine group, said method comprising providing a polypeptide comprising a norbornene group as described above, contacting said polypeptide with a tetrazine compound, and incubating to allow joining of the tetrazine to the norbornene group by a cycloaddition reaction.

Suitably said cycloaddition reaction is an inverse electron demand Diels-Alder cycloaddition reaction.

This chemistry has the advantage of speed of reaction. Thus suitably said reaction is allowed to proceed for 16 hours or less. More suitably said reaction is allowed to proceed for 2 hours or less. Most suitably said reaction is allowed to proceed for 30 minutes or less.

In another aspect, the invention relates to a method of PEGylating a polypeptide comprising carrying out the method as described above wherein said tetrazine compound is a tetrazine compound joined to a PEG group.

It will be noted that certain reaction environments may affect reaction times. Most suitably the shortest times such as 2 hours or less or 30 minutes or less are applied to in vitro reactions.

Reactions in vivo, or in eukaryotic culture conditions such as tissue culture medium or other suitable media for eukaryotic cells, may need to be conducted for longer than 30 minutes or longer than 2 hours to achieve maximal labelling. The skilled operator can determine optimum reaction times by trial and error based on the guidance provided herein.

Suitably said tetrazine compound used in the methods described is a tetrazine compound as described above.

In another aspect, the invention relates to a tetrazine compound selected from the group consisting of 5, 6, 7 or 8 of FIG. 1C. These novel compounds are especially useful as described herein.

Also described is a method of making a polypeptide comprising a norbornene group, said method comprising modifying a nucleic acid encoding said polypeptide to provide an amber codon at one or more position(s) corresponding to the position(s) in said polypeptide where it is desired to incorporate a norbornene group. Suitably modifying said nucleic acid comprises mutating a codon for lysine to an amber codon (TAG).

Targeting (ie. substitution with unnatural amino acid e.g. via amber suppression) is suitably done so that the chosen position is accessible to the tetrazine-fluorophore, i.e. lies on the surface of the folded protein. Thus polar aminoacids in the original wildtype sequences are especially suitable positions to be targeted.

Thus the invention is not limited to mutating lysine codons. In principle the invention can be applied to any position in the polypeptide. Suitably the invention is not applied to the N-terminal amino acid of the polypeptide. When selecting the position of the amino acid to be targeted in the polypeptide of interest, it is advantageous to select a surface residue. Surface residues may be determined by sequence analysis. Surface residues may be determined by three dimensional molecular modelling. Surface residues may be determined by any suitable method known in the art. Advantages of targeting surface residues include better presentation of dyes such as fluors or labels such as biophysical labels. Advantages of targeting surface residues include simpler or more efficient downstream modifications. Advantages of targeting surface residues include less likelihood of disruption of polypeptide structure and/or function by application of the label.

Particularly suitable amino acid residues to target in the polypeptide of interest include non-hydrophobic residues. Suitably hydrophobic residues are not targeted according to the invention. Suitably hydrophilic residues are targeted. Suitably polar residues are targeted. Suitably alanine or lysine are targeted. Suitably lysine is targeted. 'Targeted' preferably means substituting the codon for the residue being targeted for the orthogonal codon and synthesising the polypeptide as described in detail herein.

In another aspect, the invention relates to a homogenous recombinant polypeptide as described above. Suitably said polypeptide is made by a method as described above.

Also disclosed is a polypeptide produced according to the method(s) described herein. As well as being the product of those new methods, such a polypeptide has the technical feature of comprising norbornene.

Mutating has it normal meaning in the art and may refer to the substitution or truncation or deletion of the residue, motif or domain referred to. Mutation may be effected at the polypeptide level e.g. by synthesis of a polypeptide having the mutated sequence, or may be effected at the nucleotide level e.g. by making a nucleic acid encoding the mutated sequence, which nucleic acid may be subsequently translated to produce the mutated polypeptide. Where no amino acid is specified as the replacement amino acid for a given mutation site, suitably a randomisation of said site is used. As a default mutation, alanine (A) may be used. Suitably the mutations used at particular site(s) are as set out herein.

A fragment is suitably at least 10 amino acids in length, suitably at least 25 amino acids, suitably at least 50 amino acids, suitably at least 100 amino acids, suitably at least 200 amino acids, suitably at least 250 amino acids, suitably at least 300 amino acids, suitably at least 313 amino acids, or suitably the majority of the polypeptide of interest.

Genetic Incorporation and Polypeptide Production

In the method according to the invention, said genetic incorporation preferably uses an orthogonal or expanded genetic code, in which one or more specific orthogonal codons have been allocated to encode the specific amino acid residue with the norbornene group so that it can be genetically incorporated by using an orthogonal tRNA synthetase/tRNA pair. The orthogonal tRNA synthetase/tRNA pair can in principle be any such pair capable of charging the tRNA with the amino acid comprising the norbornene group and capable of incorporating that amino acids comprising the norbornene group into the polypeptide chain in response to the orthogonal codon.

The orthogonal codon may be the orthogonal codon amber, ochre, opal or a quadruplet codon. The codon simply has to correspond to the orthogonal tRNA which will be used to carry the amino acid comprising the norbornene group. Preferably the orthogonal codon is amber.

It should be noted that the specific examples shown herein have used the amber codon and the corresponding tRNA/tRNA synthetase. As noted above, these may be varied. Alternatively, in order to use other codons without going to the trouble of using or selecting alternative tRNA/tRNA synthetase pairs capable of working with the amino acid comprising the norbornene group, the anticodon region of the tRNA may simply be swapped for the desired anticodon region for the codon of choice. The anticodon region is not involved in the charging or incorporation functions of the tRNA nor recognition by the tRNA synthetase so such swaps are entirely within the ambit of the skilled operator.

Thus alternative orthogonal tRNA synthetase/tRNA pairs may be used if desired.

Preferably the orthogonal synthetase/tRNA pair are *Methanosarcina barkeri* MS pyrrolysine tRNA synthetase (MbPylRS) and its cognate amber suppressor tRNA (MbtRNACUA).

The *Methanosarcina barkeri* PylT gene encodes the MbtRNACUA tRNA.

The *Methanosarcina barkeri* PylS gene encodes the MbPylRS tRNA synthetase protein. When particular amino acid residues are referred to using numeric addresses, the numbering is taken using MbPylRS (*Methanosarcina barkeri* pyrrolysyl-tRNA synthetase) amino acid sequence as the reference sequence (i.e. as encoded by the publicly available wild type *Methanosarcina barkeri* PylS gene Accession number Q46E77): MDKKPLDVLI SATGLWMSRT GTLHKIKHYE VSRSKIYIEM ACGDHLVVNN SRSCRTARAF RHHKYRKTCK RCRVSDEDIN NFLTRSTEGK TSVKVKVVSA PKVKKAMPKS VSRAPKPLEN PVSAKASTDT SRSVPSPAKS TPNSPVPTSA PAPSLTRSQL DRVEALLSPE DKISLNIAKP FRELESELVT RRKNDFQRLY TNDREDYLGK LERDITKFFV DRDFLEIKSP ILIPAEYVER MGINNDTELS KQIFRVDKNL CLRPMLAPTL YNYLRKLDRI LPDPIKIFEV GPCYRKESDG KEHLEEFTMV NFCQMGSGCT RENLESLIKE FLDYLEIDFE IVGDSCMVYG DTLDIMHGDL ELSSAVVGPV PLDREWGIDK PWIGAGFGLE RLLKVMHGFK NIKRASRSES YYNGISTNL.

Said sequence has been annotated here below as SEQ ID NO.1.

If required, the person skilled in the art may adapt MbPylRS tRNA synthetase protein by mutating it so as to optimise for the norbornene amino acid to be used. The need for mutation depends on the norbornene amino acid used. An example where the MbPylRS tRNA synthetase does not need to be mutated is when the norbornene amino acid used in step (a) is Nε-5-norbornene-2-yloxycarbonyl-L-lysine. An example where the MbPylRS tRNA synthetase may need to be mutated is when the norbornene amino acid is not processed by the MbPylRS tRNA synthetase protein.

Such mutation may be carried out by introducing mutations into the MbPylRS tRNA synthetase, for example at one or more of the following positions in the MbPylRS tRNA synthetase: M241, A267, Y271, L274 and C313.

tRNA Synthetases

The tRNA synthetase of the invention may be varied. Although specific tRNA synthetase sequences may have been used in the examples, the invention is not intended to be confined only to those examples.

In principle any tRNA synthetase which provides the same tRNA charging (aminoacylation) function can be employed in the invention.

For example the tRNA synthetase may be from any suitable species such as from archea, for example from *Methanosarcina barkeri* MS; *Methanosarcina barkeri* str. Fusaro; *Methanosarcina mazei* Go1; *Methanosarcina acetivorans* C2A; *Methanosarcina thermophila*; or *Methanococcoides burtonii*. Alternatively the the tRNA synthetase may be from bacteria, for example from *Desulfitobacterium hafniense* DCB-2; *Desulfitobacterium hafniense* Y51; *Desulfitobacterium hafniense* PCP1; *Desulfotomaculum acetoxidans* DSM 771.

Exemplary sequences from these organisms are the publically available sequences. The following examples are provided as exemplary sequences for pyrrolysine tRNA synthetases:

```
>M. barkeriMS/1-419/
Methanosarcina barkeri MS
VERSION Q6WRH6.1 GI: 74501411
MDKKPLDVLISATGLWMSRTGTLHKIKHHEVSRSKIYIEMACGDHLVVNNSRSCRTARAFRHHKYRKTC

KRCRVSDEDINNFLTRSTESKNSVKVRVVSAPKVKKAMPKSVSRAPKPLENSVSAKASTNTSRSVPSPAK

STPNSSVPASAPAPSLTRSQLDRVEALLSPEDKISLNMAKPFRELEPELVTRRKNDFQRLYTNDREDYLGK

LERDITKFFVDRGFLEIKSPILIPAEYVERMGINNDTELSKQIFRVDKNLCLRPMLAPTLYNYLRKLDRILPGP

IKIFEVGPCYRKESDGKEHLEEFTMVNFCQMGSGCTRENLEALIKEFLDYLEIDFEIVGDSCMVYGDTL

DIMHGDLELSSAVVGPVSLDREWGIDKPWIGAGFGLERLLKVMHGFKNIKRASRSESYYNGISTNL

>M. barkeriF/1-419/
Methanosarcina barkeri str. Fusaro
VERSION YP_304395.1 GI: 73668380
MDKKPLDVLISATGLWMSRTGTLHKIKHYEVSRSKIYIEMACGDHLVVNNSRSCRTARAFRHHKYRKTC

KRCRVSDEDINNFLTRSTEGKTSVKVKVVSAPKVKKAMPKSVSRAPKPLENPVSAKASTDTSRSVPSPAK

STPNSPVPTSAPAPSLTRSQLDRVEALLSPEDKISLNIAKPFRELESELVTRRKNDFQRLYTNDREDYLGKLE

RDITKFFVDRDFLEIKSPILIPAEYVERMGINNDTELSKQIFRVDKNLCLRPMLAPTLYNYLRKLDRILPDPIKI

FEVGPCYRKESDGKEHLEEFTMVNFCQMGSGCTRENLESLIKEFLDYLEIDFEIVGDSCMVYGDTLDI

MHGDLELSSAVVGPVPLDREWGIDKPWIGAGFGLERLLKVMHGFKNIKRASRSESYYNGISTNL

>M. mazei/1-454
Methanosarcina mazei Go1
VERSION NP_633469.1 GI: 21227547
MDKKPLNTLISATGLWMSRTGTIHKIKHHEVSRSKIYIEMACGDHLVVNNSRSSRTARALRHHKYRKTCK

RCRVSDEDLNKFLTKANEDQTSVKVKVVSAPTRTKKAMPKSVARAPKPLENTEAAQAQPSGSKFSPAI

PVSTQESVSVPASVSTSISSISTGATASALVKGNTNPITSMSAPVQASAPALTKSQTDRLEVLLNPKDEISL

NSGKPFRELESELLSRRKKDLQQIYAEERENYLGKLEREITRFFVDRGFLEIKSPILIPLEYIERMGIDNDTELS

KQIFRVDKNFCLRPMLAPNLYNYLRKLDRALPDPIKIFEIGPCYRKESDGKEHLEEFTMLNFCQMGSGC

TRENLESIITDFLNHLGIDFKIVGDSCMVYGDTLDVMHGDLELSSAVVGPIPLDREWGIDKPWIGAGF

GLERLLKVKHDFKNIKRAARSESYYNGISTNL

>M. acetivorans/1-443
Methanosarcina acetivorans C2A
VERSION NP_615128.2 GI: 161484944
MDKKPLDTLISATGLWMSRTGMIHKIKHHEVSRSKIYIEMACGERLVVNNSRSSRTARALRHHKYRKTCR

HCRVSDEDINNFLTKTSEEKTTVKVKVVSAPRVRKAMPKSVARAPKPLEATAQVPLSGSKPAPATPVSA

PAQAPAPSTGSASATSASAQRMANSAAAPAAPVPTSAPALTKGQLDRLEGLLSPKDEISLDSEKPFRE

LESELLSRRKKDLKRIYAEERENYLGKLEREITKFFVDRGFLEIKSPILIPAEYVERMGINSDTELSKQVFRIDK

NFCLRPMLAPNLYNYLRKLDRALPDPIKIFEIGPCYRKESDGKEHLEEFTMLNFCQMGSGCTRENLEAII

TEFLNHLGIDFEIIGDSCMVYGNTLDVMHDDLELSSAVVGPVPLDREWGIDKPWIGAGFGLERLLKV

MHGFKNIKRAARSESYYNGISTNL

>M. thermophila/1-478
Methanosarcina thermophila, VERSION DQ017250.1 GI: 67773308
MDKKPLNTLISATGLWMSRTGKLHKIRHHEVSKRKIYIEMECGERLVVNNSRSCRAARALRHHKYRKIC

KHCRVSDEDLNKFLTRTNEDKSNAKVTVVSAPKIRKVMPKSVARTPKPLENTAPVQTLPSESQPAPTTPIS
```

ASTTAPASTSTTAPAPASTTAPAPASTTAPASASTTISTSAMPASTSAQGTTKFNYISGGFPRPIPVQASAP

ALTKSQIDRLQGLLSPKDEISLDSGTPFRKLESELLSRRRKDLKQIYAEEREHYLGKLEREITKFFVDRGFLEIK

SPILIPMEYIERMGIDNDKELSKQIFRVDNNFCLRPMLAPNLYNYLRKLNRALPDPIKIFEIGPCYRKESDG

KEHLEEFTMLNFCQMGSGCTRENLEAIIKDFLDYLGIDFEIVGDSCMVYGDTLDVMHGDLELSSAVV

GPVPMDRDWGINKPWIGAGFGLERLLKVMHNFKNIKRASRSESYYNGISTNL

>M. burtonii/1-416
Methanococcoides burtonii DSM6242, VERSION YP_566710.1 GI: 91774018
MEKQLLDVLVELNGVWLSRSGLLHGIRNFEITTKHIHIETDCGARFTVRNSRSSRSARSLRHNKYRKPCKR

CRPADEQIDRFVKKTFKEKRQTVSVFSSPKKHVPKKPKVAVIKSFSISTPSPKEASVSNSIPTPSISVVKDEV

KVPEVKYTPSQIERLKTLMSPDDKIPIQDELPEFKVLEKELIQRRRDDLKKMYEEDREDRLGKLERDITEFFV

DRGFLEIKSPIMIPFEYIERMGIDKDDHLNKQIFRVDESMCLRPMLAPCLYNYLRKLDKVLPDPIRIFEIGP

CYRKESDGSSHLEEFTMVNFCQMGSGCTRENMEALIDEFLEHLGIEYEIEADNCMVYGDTIDIMHGD

LELSSAVVGPIPLDREWGVNKPWMGAGFGLERLLKVRHNYTNIRRASRSELYYNGINTNL

>D. hafniense_DCB-2/1-279
Desulfitobacterium hafniense DCB-2
VERSION YP_002461289.1 GI: 219670854
MSSFWTKVQYQRLKELNASGEQLEMGFSDALSRDRAFQGIEHQLMSQGKRHLEQLRTVKHRPALLEL

EEGLAKALHQQGFVQVVTPTIITKSALAKMTIGEDHPLFSQVFWLDGKKCLRPMLAPNLYTLWRELERL

WDKPIRIFEIGTCYRKESQGAQHLNEFTMLNLTELGTPLEERHQRLEDMARWVLEAAGIREFELVTESSV

VYGDTVDVMKGDLELASGAMGPHFLDEKWEIVDPWVGLGFGLERLLMIREGTQHVQSMARSLSYL

DGVRLNIN

>D. hafniense_Y51/1-312
Desulfitobacterium hafniense Y51
VERSION YP_521192.1 GI: 89897705
MDRIDHTDSKFVQAGETPVLPATFMFLTRRDPPLSSFWTKVQYQRLKELNASGEQLEMGFSDALSRDR

AFQGIEHQLMSQGKRHLEQLRTVKHRPALLELEEGLAKALHQQGFVQVVTPTIITKSALAKMTIGEDH

PLFSQVFWLDGKKCLRPMLAPNLYTLWRELERLWDKPIRIFEIGTCYRKESQGAQHLNEFTMLNLTELGT

PLEERHQRLEDMARWVLEAAGIREFELVTESSVVYGDTVDVMKGDLELASGAMGPHFLDEKWEIVD

PWVGLGFGLERLLMIREGTQHVQSMARSLSYLDGVRLNIN

>D. hafniensePCP1/1-288
Desulfitobacterium hafniense
VERSION AY692340.1 GI: 53771772
MFLTRRDPPLSSFWTKVQYQRLKELNASGEQLEMGFSDALSRDRAFQGIEHQLMSQGKRHLEQLRTV

KHRPALLELEEKLAKALHQQGFVQVVTPTIITKSALAKMTIGEDHPLFSQVFWLDGKKCLRPMLAPNLY

TLWRELERLWDKPIRIFEIGTCYRKESQGAQHLNEFTMLNLTELGTPLEERHQRLEDMARWVLEAAGIRE

FELVTESSVVYGDTVDVMKGDLELASGAMGPHFLDEKWEIFDPWVGLGFGLERLLMIREGTQHVQS

MARSLSYLDGVRLNIN

>D. acetoxidans/1-277
Desulfotomaculum acetoxidans DSM771
VERSION YP_003189614.1 GI: 258513392
MSFLWTVSQQKRLSELNASEEEKNMSFSSTSDREAAYKRVEMRLINESKQRLNKLRHETRPAICALENRL

AAALRGAGFVQVATPVILSKKLLGKMTITDEHALFSQVFWIEENKCLRPMLAPNLYYILKDLLRLWEKPV

RIFEIGSCFRKESQGSNHLNEFTMLNLVEWGLPEEQRQKRISELAKLVMDETGIDEYHLEHAESVVYGET

VDVMHRDIELGSGALGPHFLDGRWGVVGPWVGIGFGLERLLMVEQGGQNVRSMGKSLTYLDG

VRLNI

When the particular tRNA charging (aminoacylation) function has been provided by mutating the tRNA synthetase, then it may not be appropriate to simply use another wild-type tRNA sequence, for example one selected from the above. In this scenario, it will be important to preserve the same tRNA charging (aminoacylation) function. This is accomplished by transferring the mutation(s) in the exemplary tRNA synthetase into an alternate tRNA synthetase backbone, such as one selected from the above.

In this way it should be possible to transfer selected mutations to corresponding tRNA synthetase sequences such as corresponding pylS sequences from other organisms beyond exemplary *M. barkeri* and/or *M. mazei* sequences.

Target tRNA synthetase proteins/backbones, may be selected by alignment to known tRNA synthetases such as exemplary *M. barkeri* and/or *M. mazei* sequences.

This subject is now illustrated by reference to the pylS (pyrrolysine tRNA synthetase) sequences but the principles apply equally to the particular tRNA synthetase of interest.

For example, FIG. 5 provides an alignment of all PylS sequences. These can have a low overall % sequence identity. Thus it is important to study the sequence such as by aligning the sequence to known tRNA synthetases (rather than simply to use a low sequence identity score) to ensure that the sequence being used is indeed a tRNA synthetase.

Thus suitably when sequence identity is being considered, suitably it is considered across the tRNA synthetases as in FIG. 5. Suitably the % identity may be as defined from FIG. 5. FIG. 6 shows a diagram of sequence identities between the tRNA synthetases. Suitably the % identity may be as defined from FIG. 6.

It may be useful to focus on the catalytic region. FIG. 7 aligns just the catalytic regions. The aim of this is to provide a tRNA catalytic region from which a high % identity can be defined to capture/identify backbone scaffolds suitable for accepting mutations transplanted in order to produce the same tRNA charging (aminoacylation) function, for example new or unnatural amino acid recognition.

Thus suitably when sequence identity is being considered, suitably it is considered across the catalytic region as in FIG. 7. Suitably the % identity may be as defined from FIG. 7. FIG. 8 shows a diagram of sequence identities between the catalytic regions. Suitably the % identity may be as defined from FIG. 8.

'Transferring' or 'transplanting' mutations onto an alternate tRNA synthetase backbone can be accomplished by site directed mutagenesis of a nucleotide sequence encoding the tRNA synthetase backbone. This technique is well known in the art. Essentially the backbone pylS sequence is selected (for example using the active site alignment discussed above) and the selected mutations are transferred to (i.e. made in) the corresponding/homologous positions.

When particular amino acid residues are referred to using numeric addresses, unless otherwise apparent, the numbering is taken using MbPylRS (*Methanosarcina barkeri* pyrrolysyl-tRNA synthetase) amino acid sequence as the reference sequence (i.e. as encoded by the publicly available wild type *Methanosarcina barkeri* PylS gene Accession number Q46E77):

```
MDKKPLDVLI SATGLWMSRT GTLHKIKHYE VSRSKIYIEM
ACGDHLVVNN SRSCRTARAF RHHKYRKTCK RCRVSDEDIN
NFLTRSTEGK TSVKVKVVSA PKVKKAMPKS VSRAPKPLEN
PVSAKASTDT SRSVPSPAKS TPNSPVPTSA PAPSLTRSQL
DRVEALLSPE DKISLNIAKP FRELESELVT RRKNDFQRLY
TNDREDYLGK LERDITKFFV DRDFLEIKSP ILIPAEYVER
MGINNDTELS KQIFRVDKNL CLRPMLAPTL YNYLRKLDRI
LPDPIKIFEV GPCYRKESDG KEHLEEFTMV NFCQMGSGCT
RENLESLIKE FLDYLEIDFE IVGDSCMVYG DTLDIMHGDL
ELSSAVVGPV PLDREWGIDK PWIGAGFGLE RLLKVMHGFK
NIKRASRSES YYNGISTNL
```

This is to be used as is well understood in the art to locate the residue of interest. This is not always a strict counting exercise—attention must be paid to the context or alignment. For example, if the protein of interest is of a slightly different length, then location of the correct residue in that sequence corresponding to (for example) L266 may require the sequences to be aligned and the equivalent or corresponding residue picked, rather than simply taking the 266th residue of the sequence of interest. This is well within the ambit of the skilled reader.

Notation for mutations used herein is the standard in the art. For example L266M means that the amino acid corresponding to L at position 266 of the wild type sequence is replaced with M.

The transplantation of mutations between alternate tRNA backbones is now illustrated with reference to exemplary *M. barkeri* and *M. mazei* sequences, but the same principles apply equally to transplantation onto or from other backbones.

For example Mb AcKRS is an engineered synthetase for the incorporation of AcK
  Parental protein/backbone: *M. barkeri* PylS
  Mutations: L266V, L270I, Y271F, L274A, C317F
  Mb PCKRS: engineered synthetase for the incorporation of PCK
  Parental protein/backbone: *M. barkeri* PylS
  Mutations: M241F, A267S, Y271C, L274M Synthetases with the same substrate specificities can be obtained by transplanting these mutations into *M. mazei* PylS. The sequence homology of the two synthetases can be seen in FIG. 9. Thus the following synthetases may be generated by transplantation of the mutations from the Mb backbone onto the Mm tRNA backbone:
  Mm AcKRS introducing mutations L301V, L305I, Y306F, L309A, C348F into *M. mazei* PylS, and
  Mm PCKRS introducing mutations M276F, A302S, Y306C, L309M into *M. mazei* PylS.

Full length sequences of these exemplary transplanted mutation synthetases are given below.

```
>Mb_PyIS/1-419
MDKKPLDVLISATGLWMSRTGTLHKIKHHEVSRSKIYIEMACGDHLVVNNSRSCRTARAFRHHKYRKTC

KRCRVSDEDINNFLTRSTESKNSVKVRVVSAPKVKKAMPKSVSRAPKPLENSVSAKASTNTSRSVPSPAK

STPNSSVPASAPAPSLTRSQLDRVEALLSPEDKISLNMAKPFRELEPELVTRRKNDFQRLYTNDREDYLGK
```

-continued

LERDITKFFVDRGFLEIKSPILIPAEYVERMGINNDTELSKQIFRVDKNLCLRPMLAPTLYNYLRKLDRILPGP

IKIFEVGPCYRKESDGKEHLEEFTMVNFCQMGSGCTRENLEALIKEFLDYLEIDFEIVGDSCMVYGDTL

DIMHGDLELSSAVVGPVSLDREWGIDKPWIGAGFGLERLLKVMHGFKNIKRASRSESYYNGISTNL

>Mb_AcKRS/1-419
MDKKPLDVLISATGLWMSRTGTLHKIKHHEVSRSKIYIEMACGDHLVVNNSRSCRTARAFRHHKYRKTC

KRCRVSGEDINNFLTRSTESKNSVKVRVVSAPKVKKAMPKSVSRAPKPLENSVSAKASTNTSRSVPSPAK

STPNSSVPASAPAPSLTRSQLDRVEALLSPEDKISLNMAKPFRELEPELVTRRKNDFQRLYTNDREDYLGK

LERDITKFFVDRGFLEIKSPILIPAEYVERMGINNDTELSKQIFRVDKNLCLRPMVAPTIFNYARKLDRILPG

PIKIFEVGPCYRKESDGKEHLEEFTMVNFFQMGSGCTRENLEALIKEFLDYLEIDFEIVGDSCMVYGDTL

DIMHGDLELSSAVVGPVSLDREWGIDKPWIGAGFGLERLLKVMHGFKNIKRASRSESYYNGISTNL

>Mb_PCKRS/1-419
MDKKPLDVLISATGLWMSRTGTLHKIKHHEVSRSKIYIEMACGDHLVVNNSRSCRTARAFRHHKYRKTC

KRCRVSDEDINNFLTRSTESKNSVKVRVVSAPKVKKAMPKSVSRAPKPLENSVSAKASTNTSRSVPSPAK

STPNSSVPASAPAPSLTRSQLDRVEALLSPEDKISLNMAKPFRELEPELVTRRKNDFQRLYTNDREDYLGK

LERDITKFFVDRGFLEIKSPILIPAEYVERFGINNDTELSKQIFRVDKNLCLRPMLSPTLCNYMRKLDRILPGP

IKIFEVGPCYRKESDGKEHLEEFTMVNFCQMGSGCTRENLEALIKEFLDYLEIDFEIVGDSCMVYGDTL

DIMHGDLELSSAVVGPVSLDREWGIDKPWIGAGFGLERLLKVMHGFKNIKRASRSESYYNGISTNL

>Mm_PylS/1-454
MDKKPLNTLISATGLWMSRTGTIHKIKHHEVSRSKIYIEMACGDHLVVNNSRSSRTARALRHHKYRKTCK

RCRVSDEDLNKFLTKANEDQTSVKVKVVSAPTRTKKAMPKSVARAPKPLENTEAAQAQPSGSKFSPAI

PVSTQESVSVPASVSTSISSISTGATASALVKGNTNPITSMSAPVQASAPALTKSQTDRLEVLLNPKDEISL

NSGKPFRELESELLSRRKKDLQQIYAEERENYLGKLEREITRFFVDRGFLEIKSPILIPLEYIERMGIDNDTELS

KQIFRVDKNFCLRPMLAPNLYNYLRKLDRALPDPIKIFEIGPCYRKESDGKEHLEEFTMLNFCQMGSGC

TRENLESIITDFLNHLGIDFKIVGDSCMVYGDTLDVMHGDLELSSAVVGPIPLDREWGIDKPWIGAGF

GLERLLKVKHDFKNIKRAARSESYYNGISTNL

>Mm_AcKRS/1-454
MDKKPLNTLISATGLWMSRTGTIHKIKHHEVSRSKIYIEMACGDHLVVNNSRSSRTARALRHHKYRKTCK

RCRVSDEDLNKFLTKANEDQTSVKVKVVSAPTRTKKAMPKSVARAPKPLENTEAAQAQPSGSKFSPAI

PVSTQESVSVPASVSTSISSISTGATASALVKGNTNPITSMSAPVQASAPALTKSQTDRLEVLLNPKDEISL

NSGKPFRELESELLSRRKKDLQQIYAEERENYLGKLEREITRFFVDRGFLEIKSPILIPLEYIERMGIDNDTELS

KQIFRVDKNFCLRPMVAPNIFNYARKLDRALPDPIKIFEIGPCYRKESDGKEHLEEFTMLNFFQMGSGC

TRENLESIITDFLNHLGIDFKIVGDSCMVYGDTLDVMHGDLELSSAVVGPIPLDREWGIDKPWIGAGF

GLERLLKVKHDFKNIKRAARSESYYNGISTNL

>Mm_PCKRS/1-454
MDKKPLNTLISATGLWMSRTGTIHKIKHHEVSRSKIYIEMACGDHLVVNNSRSSRTARALRHHKYRKTCK

RCRVSDEDLNKFLTKANEDQTSVKVKVVSAPTRTKKAMPKSVARAPKPLENTEAAQAQPSGSKFSPAI

PVSTQESVSVPASVSTSISSISTGATASALVKGNTNPITSMSAPVQASAPALTKSQTDRLEVLLNPKDEISL

NSGKPFRELESELLSRRKKDLQQIYAEERENYLGKLEREITRFFVDRGFLEIKSPILIPLEYIERFGIDNDTELSK

QIFRVDKNFCLRPMLSPNLCNYMRKLDRALPDPIKIFEIGPCYRKESDGKEHLEEFTMLNFCQMGSGC

TRENLESIITDFLNHLGIDFKIVGDSCMVYGDTLDVMHGDLELSSAVVGPIPLDREWGIDKPWIGAGF

GLERLLKVKHDFKNIKRAARSESYYNGISTNL

The same principle applies equally to other mutations and/or to other backbones.

Transplanted polypeptides produced in this manner should advantageously be tested to ensure that the desired function/substrate specificities have been preserved.

Advantageous Synthetases

The inventors performed selections in order to find an orthogonal tRNA/tRNA synthetase pair that would direct incorporation of norbornene lysine with higher yields. One preferred synthetase consisted of a MbtRNA synthetase (MbPylRS) with the following mutations in the catalytic active site: L275A, C314S, M316I. This synthetase is suitably used with the MbtRNACUA tRNA. Usage of this tRNA/tRNA synthetase pair lead to better yields for protein expression. The same mutations may be made on other synthetase backbones as explained above.

In addition, examples of other *M. mazei* based tRNA synthetase sequences for incorporation of norbornene lysine include:

MmPylRS with mutations Y306A, Y384F
described in

Amino acids for diels-alder reactions in living cells. Plass, T., Milles, S., Koehler, C., Szymanski, J., Mueller, R., Wiessler, M., Schultz, C. & Lemke, E. A. Angew Chem Int Ed Engl. 2012 Apr. 23; 51(17):4166-70. doi: 10.1002/anie.201108231.Epub 2012 Mar. 30.

The same mutations may be made on other synthetase backbones as explained above.

MmPylRS with mutations Y384F, Y3066, and I405R.
described in

A genetically encoded norbornene amino acid for the mild and selective modification of proteins in a copper-free click reaction. Kaya E, Vrabel M, Deiml C, Prill S, Fluxa V S, Caret T., Angew Chem Int Ed Engl. 2012 Apr. 27; 51(18):4466-9. doi: 10.1002/anie.201109252. Epub 2012 Mar. 21.

The same mutations may be made on other synthetase backbones as explained above.

Polynucleotides encoding the polypeptide of interest for the method described above can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Vectors of the invention may be transformed or transfected into a suitable host cell as described to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Another aspect of the invention is a method, such as an in vitro method, of incorporating the norbornene containing amino acid(s) genetically and site-specifically into the protein of choice, suitably in a eukaryotic cell. One advantage of incorporating genetically by said method is that it obviates the need to deliver the proteins comprising the norbornene amino acid into a cell once formed, since in this embodiment they may be synthesised directly in the target cell. The method comprises the following steps:

i) introducing, or replacing a specific codon with, an orthogonal codon such as an amber codon at the desired site in the nucleotide sequence encoding the protein ii) introducing an expression system of orthogonal tRNA synthetase/tRNA pair in the cell, such as a pyrollysyl-tRNA synthetase/tRNA pair iii) growing the cells in a medium with the norbornene containing amino acid according to the invention.

Step (i) entails or replacing a specific codon with an orthogonal codon such as an amber codon at the desired site in the genetic sequence of the protein. This can be achieved by simply introducing a construct, such as a plasmid, with the nucleotide sequence encoding the protein, wherein the site where the norbornene containing amino acid is desired to be introduced/replaced is altered to comprise an orthogonal codon such as an amber codon. This is well within the person skilled in the art's ability and examples of such are given here below.

Step (ii) requires an orthogonal expression system to specifically incorporate the norbornene containing amino acid at the desired location (e.g. the amber codon). Thus a specific orthogonal tRNA synthetase such as an orthogonal pyrollysyl-tRNA synthetase and a specific corresponding orthogonal tRNA pair which are together capable of charging said tRNA with the norbornene containing amino acid are required. Examples of these are provided herein.

Protein Expression and Purification

Host cells comprising polynucleotides of the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins of the invention can be extracted from host cells by a variety of techniques known in the art, including enzymatic, chemical and/or osmotic lysis and physical disruption.

Proteins of the invention can be purified by standard techniques known in the art such as preparative chromatography, affinity purification or any other suitable technique.

Tetrazine Compounds

Suitably the norbornene group incorporated into the polypeptide of interest is reacted with a tetrazine compound. The tetrazine acts to conveniently attach a molecule of interest to the polypeptide via the norbornene. Thus suitably the tetrazine compound bears the molecule of interest.

Suitably said tetrazine group may be further joined to any suitable molecule of interest for attaching same to the polypeptide via the norbornene-tetrazine reaction.

Tetrazines are designed and synthesized in a way that they have a readily accessible primary amino group. This amino group can be reacted with a variety of compounds using standard amine coupling reactions. As tetrazines are stable in a wide variety of reaction conditions almost any compound can be coupled to the tetrazine of interest. Exemplary compounds joined to tetrazines (for attachment to polypeptide via the norbornene) include various fluorophores as mentioned herein (such as in the examples section). Tetrazines may also be coupled to more sophisticated fluorophores, e.g. those suitable for Super Resolution Microscopy, such as STORM, PALM or STED, (for example Alexa dyes or special dyes from Abberior, developed for STED microscopy). Lipids may be coupled to tetrazines via standard techniques. PEGs may be coupled to tetrazines (see examples), which are beneficial for PEGylation of polypeptides via the norbornene according to the invention.

In all cases the key benefits of our approach include the fact that the incorporation of norbornene according to the invention is site specific and most importantly can be done in vivo (and/or in vitro in an organism such as *E. coli*). By contrast, in prior art approaches the purified antibody or protein can only be reacted in vitro with norbornene in a non-selective and not site-specific manner which has numerous problems as set out above. Thus the invention delivers significant benefits compared to prior art methods as demonstrated herein.

The norbornene containing polypeptide of the invention may be conveniently conjugated to other biophysical labels than fluorophores, for example, NMR probes, Spin label probes, IR labels, EM-probes as well as small molecules, oligonucleotides, lipids, nanoparticles, quantum dots, biophysical probes (EPR labels, NMR labels, IR labels), small molecules (biotin, drugs, lipids), oligonucleotides (DNA, RNA, LNA, PNA), particles (nanoparticles, viruses), polymers (PEG, PVC), proteins, peptides, surfaces and the like.

Definitions

The term 'comprises' (comprise, comprising) should be understood to have its normal meaning in the art, i.e. that the stated feature or group of features is included, but that the term does not exclude any other stated feature or group of features from also being present.

Further Advantages

Blackmann et al JACS 2008 inverse electron demand Diels Alder reactions between a tetrazine and a strained alkene (transcyclooctene) in water, cell media or cell lysates. A small protein (thioredoxin) was functionalised with a trans-cyclooctene derivative. Thioredoxin is a small protein (11 kDa) that contains a single disulfide. Upon reduction of this disulfide, the thiol group was reacted selectively with a maleimide that was linked to a trans-cyclooctene derivative. The so modified thioredoxin was then reacted with a tetrazine and the tetrazine ligation was confirmed by mass spectrometry. This prior art method is a standard biochemical ligation. This cannot be performed selectively. All cysteines present will be labelled by this method. If no cysteines are present, no reaction will be possible. By contrast the present invention allows the labelling of any predetermined site on a polypeptide. By contrast the invention allows selective labelling. By contrast the present invention avoids the complicated post-translational chemistry of this prior art technique. By contrast the present invention allows the labelling to take place without the need to produce purified protein (eg. see FIG. 3 and the examples). By contrast the present invention allows labelling in live cells with high selectivity over other proteins.

Weissleder has also coupled norbornene to different antibodies and labelled them afterwards with tetrazine fluorophores. Also in these cases the antibodies were labelled with standard amine coupling techniques, i.e. the antibodies were incubated with an activated form (mostly a succinimidyl ester) of the corresponding strained alkene (e.g. norbornene) so that all lysines as well as the N-terminal end of the antibody polypeptide are reacted with it. Therefore this known method is not a site selective method of labelling. In addition this known method is confined to a biochemical reaction. This reaction must be done on purified antibody polypeptide. By contrast the present invention allows the labelling of any predetermined site on a polypeptide. By contrast the invention allows selective labelling. By contrast the present invention avoids the complicated post-translational chemistry of this prior art technique. By contrast the present invention avoids labelling the N-terminus of the polypeptide. By contrast the present invention allows the labelling to take place without the need to produce purified protein (eg. see FIG. 3 and the examples). By contrast the present invention allows labelling in live cells with high selectivity over other proteins.

It is an advantage of the invention that norbornene is incorporated selectively into the polypeptide.

It is an advantage of the invention that norbornene is incorporated into the polypeptide with excellent yields.

It is an advantage of the invention that norbornene is incorporated into the polypeptide with improved (faster) kinetics compared to known approaches.

It is an advantage of the invention that norbornene is incorporated at a predetermined position of the polypeptide.

BRIEF DESCRIPTION OF THE FIGURES

FIG. 2A shows the amino acid dependent expression of sfGFP bearing an amber codon at position 150 and myoglobin bearing an amber codon at position 4. FIG. 2B shows the MS characterization of amino acid incorporation, left: sfGFP-2-His$_6$, found: 27975.5±1.5 Da, calculated: 27977.5 Da; right: Myo-2-His$_6$, found: 18532.5±1.5 Da, calculated: 18532.2 Da).

FIG. 3A shows "turn-on" fluorescence of tetrazine-fluorophores upon reaction with 5-norbornene-2-ol (Nor). FIG. 3B shows specific and quantitative labeling of sfGFP bearing 2 as demonstrated by SDS PAGE (Coomassie staining and in gel fluorescence) and mass spectrometry. Red mass spectrum: before bioconjugation, found 27975.5±1.5 Da, expected 27977.5 Da. Blue mass spectrum: after bioconjugation, found 28783.0±1.5 Da, expected 28784.4 Da. FIG. 3C shows labeling of myoglobin bearing 2 at position 4 with 12. Top fluorescence imaging, bottom Coomassie stained loading control. FIG. 3D shows specificity of labeling 2 in sfGFP versus the *E. coli* proteome. Lanes 1-5: Coomassie stained gel showing proteins from *E. coli* producing sfGFP in the presence of the indicated concentration of unnatural amino acids 2 or 3. Lanes 6-10: The expressed protein was detected in lysates using an anti $His_6$ antibody. Lanes 11-20: Fluorescence images of protein labeled with the indicated fluorophore 12 or 13.

FIGS. 4A-C: Site-specific incorporation of 2 into proteins in mammalian cells and the specific labeling of EGFR-GFP on the cell surface with tetrazine-fluorophore 9. FIG. 4A shows cells containing the $PylRS/tRNA_{CUA}$ pair and the mCherry(TAG)eGFP-HA reporter produce GFP only in the presence of 2. FIG. 4B shows Western blots confirming that the expression of full length mCherry(TAG)eGFP-HA is dependent on the presence of 2. FIG. 4C shows specific and rapid labeling of a cell surface protein in live mammalian cells. EGFR-GFP bearing 2 or 3 at position 128 is visible as green fluorescence at the membrane of transfected cells (left panels). Treatment of cells with 9 (200 nM) leads to selective labeling of EGFR containing 2 (middle panels). Cells were imaged 4 hours after addition of 9.

FIG. 5 shows alignment of PylS sequences.

FIG. 8 shows sequence identity of the catalytic domains of PylS sequences.

Figure 9:
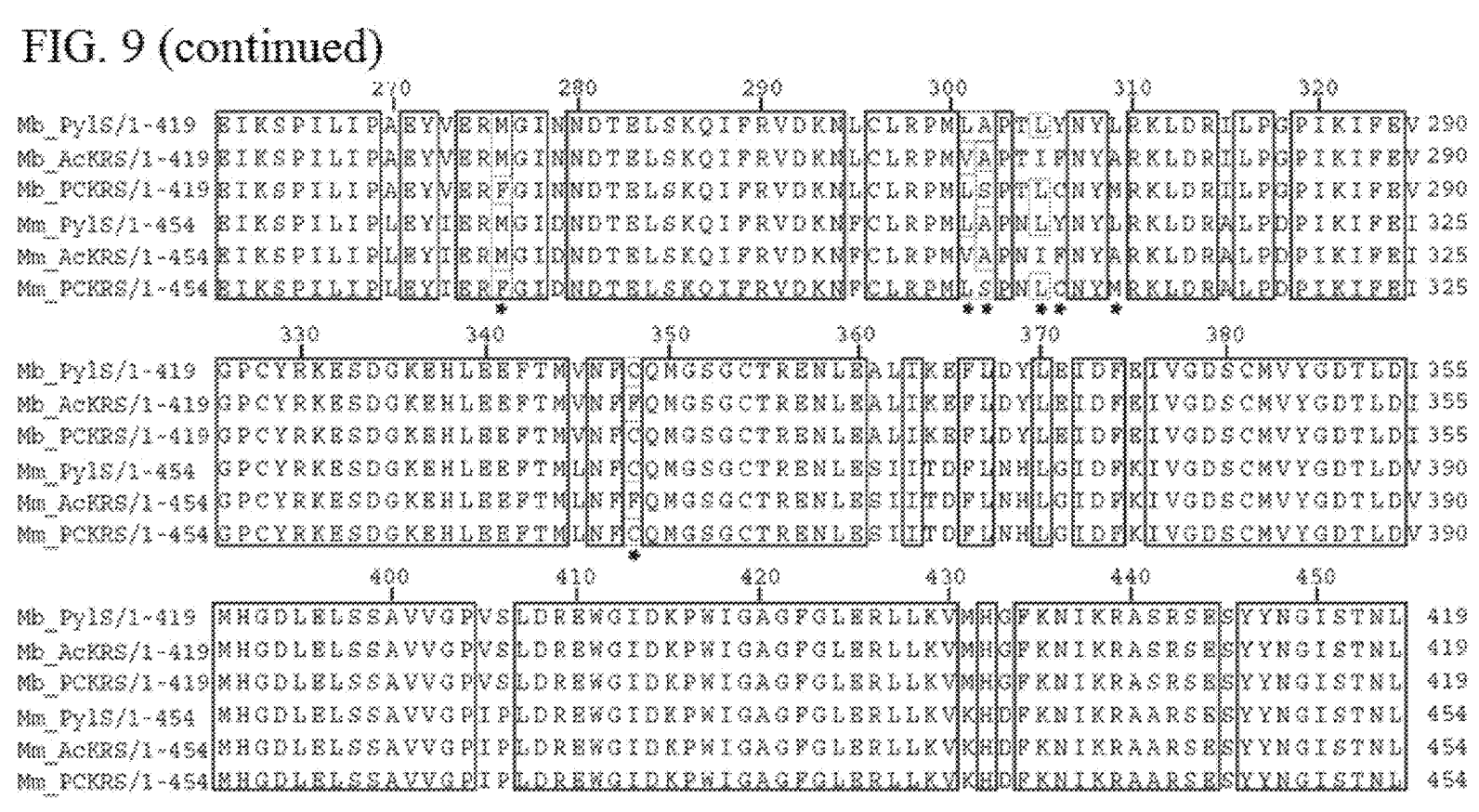

FIG. 9 shows alignment of synthetases with transplanted mutations based on *M. barkeri* PylS or *M. mazei* PylS. The red asterisks indicate the mutated positions.

FIG. 10A shows a schematic of the protein PEGylation reaction of a norbornene-protein and a tetrazine-PEG reagent. FIG. 10B shows PAGE gel showing purified superfolder-green fluorescent protein (sfGFP) containing the nor-bornene-lysine (NorK) incorporated at position 00 in a *E. coli* expression system. FIG. 10C shows PAGE gel (imaging GFP fluorescence) of the PEGylation reaction showing a distinct change in molecular weight of sfGFP through addition of a single PEG group.

FIG. 12 shows bioconjugation reactions applied in bioorthogonal labeling. The reaction between a tetrazine and a norbornene (A) has important advantages over all other bioconjugation reactions developed in the art to date. Embodiment of the invention is outlined in bold.

FIGS. 15A-C show rate constants k for different tetrazines were measured under pseudo first order conditions with a 10- to 100-fold excess of 5-norbornene-2-ol in methanol/water mixtures by following the exponential decay in UV absorbance of the tetrazine at 320 or 300 nm over time.

FIG. 16A shows rate constants for the reaction of 5-nor-bornene-2-ol with various tetrazines.

FIG. 16B shows mass spectrometry data for tetrazine-fluorophores 9-14.

FIG. 22 shows the gel fluorescence imaging of the labeling reaction of sfGFP-2 with tetrazine fluorophores 9 and 12.

FIG. 25 shows specific and rapid labeling of EGFR-2-GFP in mammalian cells with a tetrazine-based fluorophore 9 (4 h).

FIG. 26 shows specific and rapid labeling of EGFR-2-GFP in mammalian cells with a tetrazine-based fluorophore 9 (8 h).

FIG. 27 shows specific and rapid labeling of EGFR-2-GFP in mammalian cells with a tetrazine-based fluorophore 9 (16 h).

The invention is now described by way of example. These examples are intended to be illustrative, and are not intended to limit the appended claims.

EXAMPLES

Example 1: Comparison to Prior Art Techniques

Background

Conventional methods for protein modification have involved selective reactions of the functionalities found in the side-chains of natural amino acids.[1] Cysteine and lysine are by far the most commonly used residues because of their relatively low abundance in proteins and the broad range of available methods to modify their nucleophilic side chains.[2] This method is widely used for the conjugation of several small-molecule probes such as biotin and fluorophores.

However, this residue-specific method for protein modification is generally inadequate due to the presence of multiple identical residues found within biological systems and within the proteins themselves.

To date, the mainstay tagging strategy for cellular imaging of proteins in cells involves genetic fusions of fluorescent proteins (FPs). The availability of the green fluorescent protein (GFP) and its related variants have provided means of studying binding interactions, trafficking, stability, function and spatiotemporal distribution of proteins in living cells or model organisms.[3-5] However, the large size of FPs often interferes with the folding and activity of target proteins.[6, 7] Alternatives to the FPs have exploited covalent a tag-mediated labeling method such as self-labeling proteins and enzyme-mediated labeling. The most widely employed self-labeling proteins are the HaloTag,[8,9] SNAP-tag[10] and CLIP-tag.[11] An advantage to this method is the flexibility in the choice of a tag. Although these modifications are smaller relative to GFP, the target protein is still perturbed in contrast to its native counterpart, thus the main limitation of fluorescent protein fusions still persists. Enzyme-mediated labeling however provides a convenient combination of a small tag size and high specificity but unfortunately also has a very limited set of probe molecules and in most cases is restricted to labeling cell surface proteins.[12, 13]

A highly targeted strategy to label proteins is to introduce a single-residue modification. However, in order to study proteins in their native surroundings, chemoselectivity needs to apply not only to a complex mixture but also to the functionalities found on a single protein and its labeling partner. Therefore, at a specific location, an inconspicuous bioorthogonal modification should be introduced into a protein under physiological conditions.

Invention

According to the invention, this can be achieved by altering the protein translation machinery to introduce unnatural amino acids with a bioorthogonal handle, e.g., a norbornene.

Figure 11:
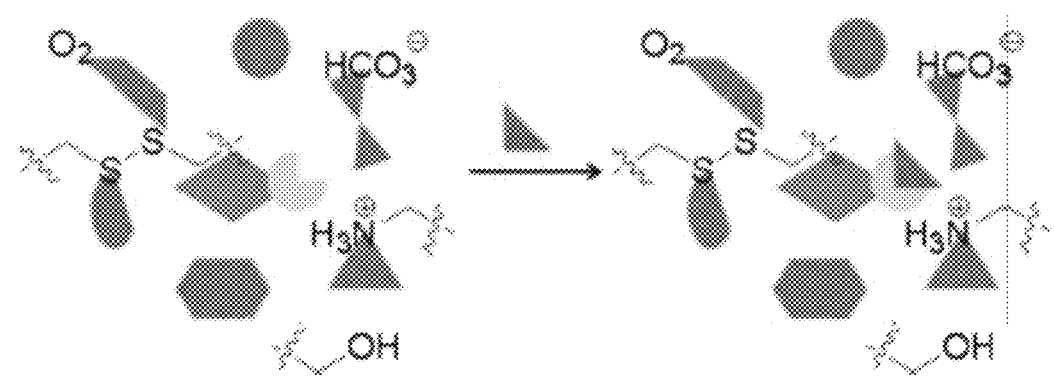
FIG. 11 shows a representation of a selective, bioorthogonal conjugation reaction. The reaction between a chemical handle (yellow—pie shape) linked to a biomolecule (orange—diamond shape), e.g., an unnatural amino acid introduced into a protein, and a reactive probe (green—oblique triangle shape) bearing bioorthogonal functional groups proceeds in the presence of all the functionality found within living systems (blue—remaining shapes around periphery) under physiological conditions.

FIG. 11 shows a representation of a selective, bioorthogonal conjugation reaction. The reaction between a chemical handle (yellow—pie shape) linked to a biomolecule (orange—diamond shape), e.g., an unnatural amino acid introduced into a protein, and a reactive probe (green—oblique triangle shape) bearing bioorthogonal functional groups proceeds in the presence of all the functionality found within living systems (blue—remaining shapes around periphery) under physiological conditions.

The bioconjugation reaction then involves the site-specific pre-modified protein carrying a unique chemical handle (functionalized unnatural amino acid, e.g., norbornene lysine) that will specifically and covalently bind to a labeling molecule without perturbation of structure and function. Furthermore, the majority of the methods available for protein labeling (some described above) have been primarily developed to provide fluorescent tags, whereas unnatural amino acids allow the introduction of virtually any type of physical and chemical label, even polymers like polyethylene glycol (PEG). Thus, a protein that carries a specific reactive handle within a complex environment can be conjugated with an otherwise inert molecule capable of being traced and detected. Bioconjugation reactions to proteins using unnatural amino acids are the key to developing new technologies to study and understand life's cellular processes.

Many bioconjugation reactions have been developed and established for the use of bioorthogonal chemical probes in proteins and other biomolecules by different means.[2, 14] A selection of bioconjugation reactions are listed and briefly described in the Table below.

Advantages and Applications of the Invention

The inverse electron demand Diels-Alder (IED-DA) cycloaddition reaction between a tetrazine and a strained olefin is a superior bioorthogonal reaction with important advantages o ver the other bioconjugation reactions shown in Table 1, such as high selectivity, excellent yields, and extremely fast kinetics in aqueous media. Recently, the IED-DA reaction has been successfully applied in bioconjugation reactions to a tetrazine-modified thioredoxin (Trx) in an acetate buffer[15] and to a norbornene-bearing antibody in both serum and live cells.[16]

We have greatly extended the applicability of the IED-DA reaction for protein bioconjugation purposes by synthesizing and genetically incorporating a novel norbornene-lysine amino acid. The genetic encoding of this amino acid allows for the recombinant expression of proteins that bear the norbornene moiety at defined locations in both pro- and eukaryotic cells. Specifically, protein can be easily produced on an industrial scale and bioconjugation reactions can be performed with complete amino acid specificity.

This enables the precise modification of proteins with a wide range of probes, since the IED-DA reaction exhibits a wide tolerance of functional groups and proceeds with high yield. Further applications of this method are:
- labeling of proteins with biophysical and cellular probes (e.g., fluorescent labels, spin labels, NMR labels, IR labels, etc.)
- bioconjugation of therapeutic proteins with biologically active small molecules (e.g., cytotoxic compounds or cell targeting compounds)
- bioconjugation of therapeutic proteins with polymers (e.g., polyethylene glycol to enhance stability and circulation time or polyamines for cellular uptake)
- immobilization of proteins on surfaces (e.g., for the creation of biosensors)

REFERENCES TO EXAMPLE 1

1. Basle, E., Joubert, N. & Pucheault, M. Protein chemical modification on endogenous amino acids. *Chem Biol* 17, 213-227 (2010).
2. Sletten, E. M. & Bertozzi, C. R. Bioorthogonal chemistry: fishing for selectivity in a sea of functionality. *Angew Chem Int Ed Engl* 48, 6974-6998 (2009).
3. Tsien, R. Y. The green fluorescent protein. *Annu Rev Biochem* 67, 509-544 (1998).
4. Lippincott-Schwartz, J. & Patterson, G. H. Development and use of fluorescent protein markers in living cells. *Science* 300, 87-91 (2003).
5. Hadjantonakis, A. K., Dickinson, M. E., Fraser, S. E. & Papaioannou, V. E. Technicolour transgenics: imaging tools for functional genomics in the mouse. *Nat Rev Genet* 4, 613-625 (2003).
6. Strack, R. L. et al. A noncytotoxic DsRed variant for whole-cell labeling. *Nat Methods* 5, 955-957 (2008).
7. Tour, O. et al. Calcium Green FlAsH as a genetically targeted small-molecule calcium indicator. *Nat Chem Biol* 3, 423-431 (2007).
8. Los, G. V. & Wood, K. The HaloTag: a novel technology for cell imaging and protein analysis. *Methods Mol Biol* 356, 195-208 (2007).

9. Los, G. V. et al. HaloTag: a novel protein labeling technology for cell imaging and protein analysis. *ACS Chem Biol* 3, 373-382 (2008).
10. Keppler, A. et al. A general method for the covalent labeling of fusion proteins with small molecules in vivo. *Nat Biotechnol* 21, 86-89 (2003).
11. Gautier, A. et al. An engineered protein tag for multi-protein labeling in living cells. *Chem Biol* 15, 128-136 (2008).
12. Cronan, J. E. Biotination of proteins in vivo. A post-translational modification to label, purify, and study proteins. *J Biol Chem* 265, 10327-10333 (1990).
13. Walsh, C. T., Garneau-Tsodikova, S. & Gatto, G. J. Protein posttranslational modifications: the chemistry of proteome diversifications. *Angew Chem Int Ed Engl* 44, 7342-7372 (2005).
14. Lim, R. K. & Lin, Q. Bioorthogonal chemistry: recent progress and future directions. *Chem Commun (Comb)* 46, 1589-1600 (2010).
15. Blackman, M. L., Royzen, M. & Fox, J. M. Tetrazine ligation: fast bioconjugation based on inverse-electron-demand Diels-Alder reactivity. *J Am Chem Soc* 130, 13518-13519 (2008).
16. Devaraj, N. K., Weissleder, R. & Hilderbrand, S. A. Tetrazine-based cycloadditions: application to pretargeted live cell imaging. *Bioconjug Chem* 19, 2297-2299 (2008).
17. Devaraj, N. K. & Weissleder, R. Biomedical Applications of Tetrazine Cycloadditions. *Acc Chem Res* (2011).
18. Geoghegan, K. F. & Stroh, J. G. Site-directed conjugation of nonpeptide groups to peptides and proteins via periodate oxidation of a 2-amino alcohol. Application to modification at N-terminal serine. *Bioconjug Chem* 3, 138-146 (1992).
19. Gaertner, H. F. & Offord, R. E. Site-specific attachment of functionalized poly(ethylene glycol) to the amino terminus of proteins. *Bioconjug Chem* 7, 3844 (1996).
20. Breinbauer, R. & Köhn, M. Azide-alkyne coupling: a powerful reaction for bioconjugate chemistry. *Chembiochem* 4, 1147-1149 (2003).
21. Hein, C. D., Liu, X. M. & Wang, D. Click chemistry, a powerful tool for pharmaceutical sciences. *Pharm Res* 25, 2216-2230 (2008).
22. de Graaf, A. J., Kooijman, M., Hennink, W. E. & Mastrobattista, E. Nonnatural amino acids for site-specific protein conjugation. *Bioconjug Chem* 20, 12811295 (2009).
23. Agard, N. J., Prescher, J. A. & Bertozzi, C. R. A strain-promoted [3+2] azide-alkyne cycloaddition for covalent modification of biomolecules in living systems. *J Am Chem Soc* 126, 15046-15047 (2004).
24. Shelbourne, M., Chen, X., Brown, T. & El-Sagheer, A. H. Fast copper-free click DNA ligation by the ring-strain promoted alkyne-azide cycloaddition reaction. *Chem Commun (Camb)* 47, 6257-6259 (2011).
25. Köhn, M. & Breinbauer, R. The Staudinger ligation—a gift to chemical biology. *Angew Chem Int Ed Engl* 43, 3106-3116 (2004).
26. Debets, M. F., van der Doelen, C. W., Rutjes, F. P. & van Delft, F. L. Azide: a unique dipole for metal-free bioorthogonal ligations. *Chembiochem* 11, 1168-1184 (2010).
27. Tona, R. & Häner, R. Synthesis and bioconjugation of diene-modified oligonucleotides. *Bioconjug Chem* 16, 837-842 (2005).
28. Hill, K. W. et al. Diels-Alder bioconjugation of diene-modified oligonucleotides. *J Org Chem* 66, 5352-5358 (2001).
29. de Araújo, A. D. et al. Diels-Alder ligation of peptides and proteins. *Chemistry* 12, 6095-6109 (2006).
30. Palomo, J. M. Diels-Alder Cycloaddition in Protein Chemistry. *Eur. J. Org. Chem* 33, 6303-6314 (2010).
31. Filice, M., Romero, O., Guisan, J. M. & Palomo, J. M. trans,trans-2,4-Hexadiene incorporation on enzymes for site-specific immobilization and fluorescent labeling. *Org Biomol Chem* 9, 5535-5540 (2011).
32. Wang, Y., Vera, C. I. & Lin, Q. Convenient synthesis of highly functionalized pyrazolines via mild, photoactivated 1,3-dipolar cycloaddition. *Org Lett* 9, 4155-4158 (2007).
33. Song, W., Wang, Y., Qu, J. & Lin, Q. Selective functionalization of a genetically encoded alkene-containing protein via "photoclick chemistry" in bacterial cells. *J Am Chem Soc* 130, 9654-9655 (2008).
34. Lin, Y. A., Chalker, J. M., Floyd, N., Bernardes, G. J. & Davis, B. G. Allyl sulfides are privileged substrates in aqueous cross-metathesis: application to site-selective protein modification. *J Am Chem Soc* 130, 9642-9643 (2008).
35. Chalker, J. M., Lin, Y. A., Boutureira, O. & Davis, B. G. Enabling olefin metathesis on proteins: chemical methods for installation of S-allyl cysteine. *Chem Commun (Camb)*, 3714-3716 (2009).
36. Lin, V. A. & Davis, B. G. The allylic chalcogen effect in olefin metathesis. *Beilstein J Org Chem* 6, 1219-1228 (2010).
37. Hoyle, C. E. & Bowman, C. N. Thiol-ene click chemistry. *Angew Chem Int Ed Engl* 49, 1540-1573 (2010).
38. Weinrich, D. et al. Oriented immobilization of farnesylated proteins by the thiol-ene reaction. *Angew Chem Int Ed Engl* 49, 1252-1257 (2010).
39. Kodama, K. et al. Regioselective carbon-carbon bond formation in proteins with palladium catalysis; new protein chemistry by organometallic chemistry. *Chembiochem* 7, 134-139 (2006).
40. Kodama, K. et al. Site-specific functionalization of proteins by organopalladium reactions. *Chembiochem* 8, 232-238 (2007).
41. Brustad, E. et al. A genetically encoded boronate-containing amino acid. *Angew Chem Int Ed Engl* 47, 8220-8223 (2008).

Example 1A: Targeting Varied Residues

The target residue need not be a lysine in the polypeptide of interest.

The following proteins have been expressed with norbornene lysine (NorK) incorporated at (i.e. substituted into) the following positions:

T4 lysozyme (position 83, in wildtype position 83 is a lysine)

Myoglobin (position 4, which in the wildtype sequence is a serine)

sfGFP (position 150, which in the wildtype is an asparagine)

Thus targeting of residues other than lysine is demonstrated.

Example 1B: Selectivity of the Norbornene-Tetrazine Reaction Against the *E. coli* Proteome To probe the specificity of the reaction between the genetically encoded norbornene and the tetrazine-based fluorophores we performed the labelling reaction in the proteome of *E. coli* expressing either c-terminally His-tagged sfGFP or His-tagged myoglobin. We controlled the level of recombinant protein expression so that it was equal to or less than that of many endogenous proteins by modulating the concentration of norbornene-lysine added to cells. This ensures that any specific labelling of the target protein versus native proteins is not an artefact of the abundance of the target protein.

Figure 3A:
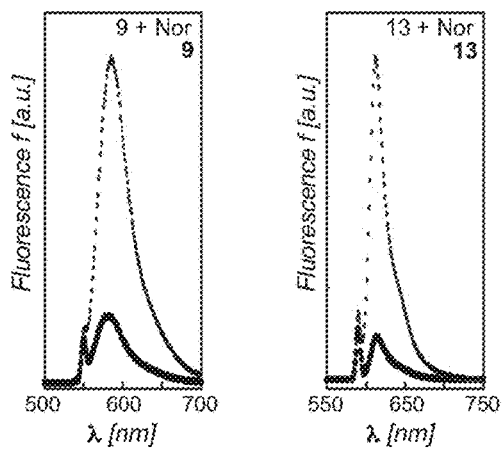
FIGS. 3A-D show the characterization of tetrazine norbornene reactions.
Figures 3B, 3C:
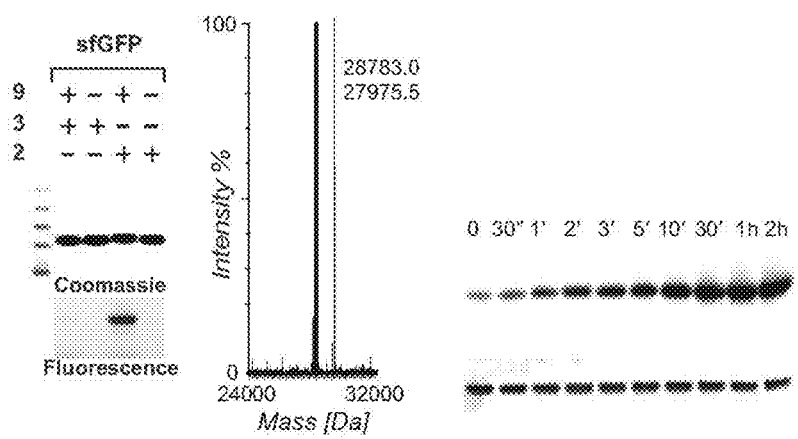
Figure 3D:
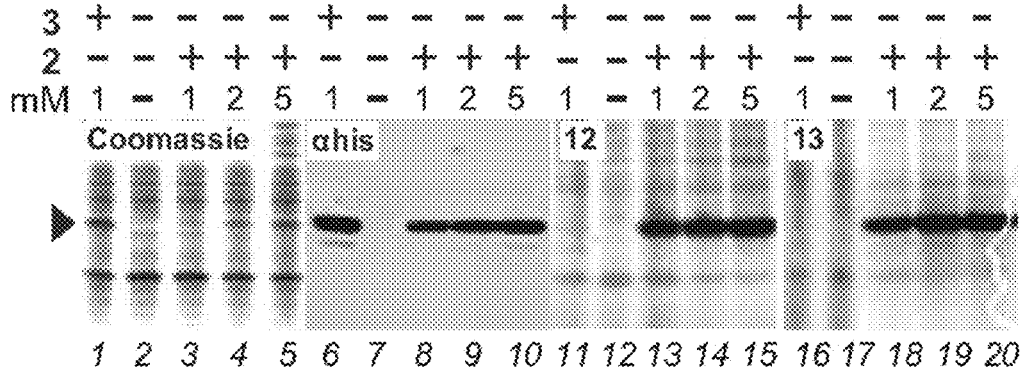
Figure 6:
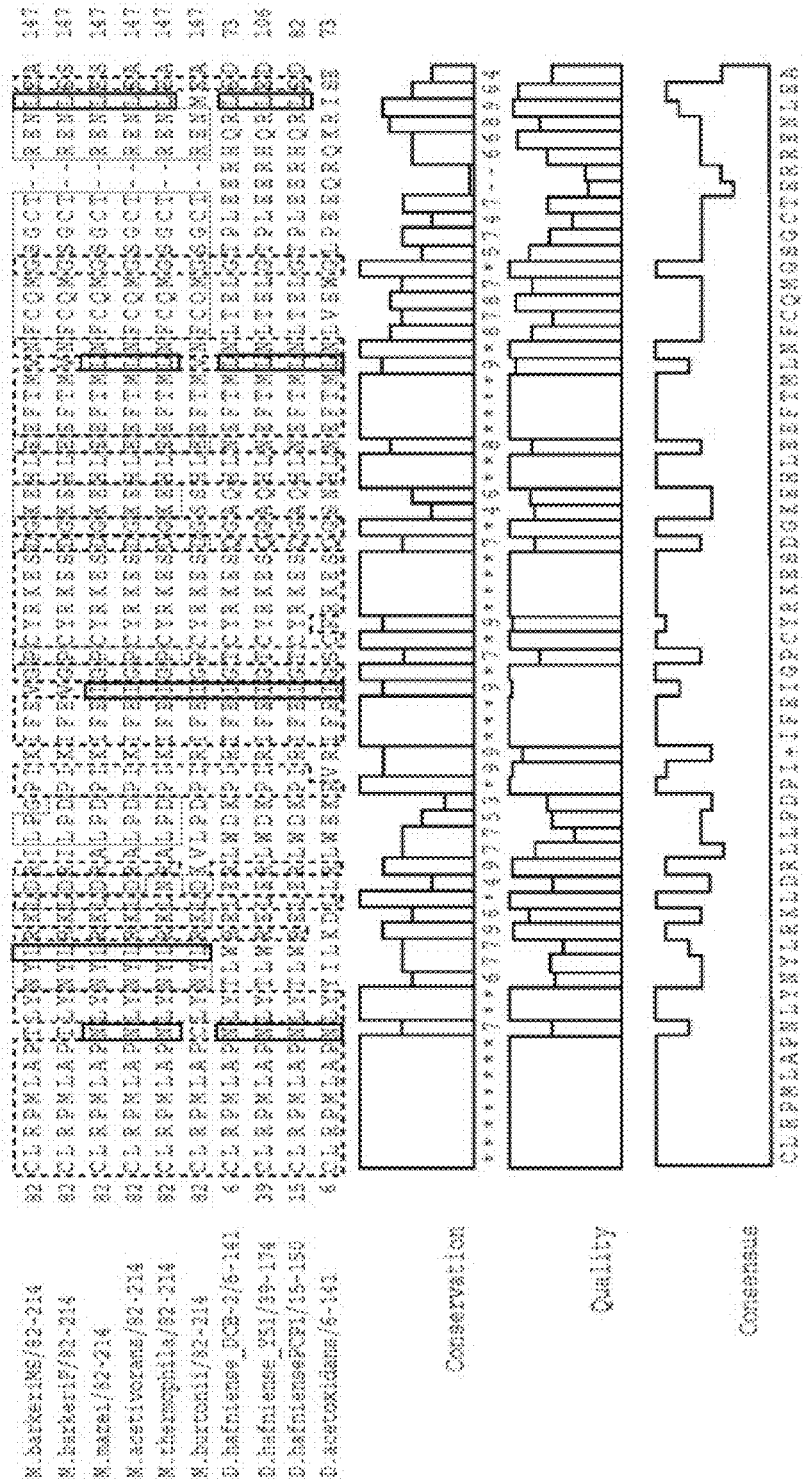
FIG. 6 shows sequence identity of PylS sequences.
Figure 7:
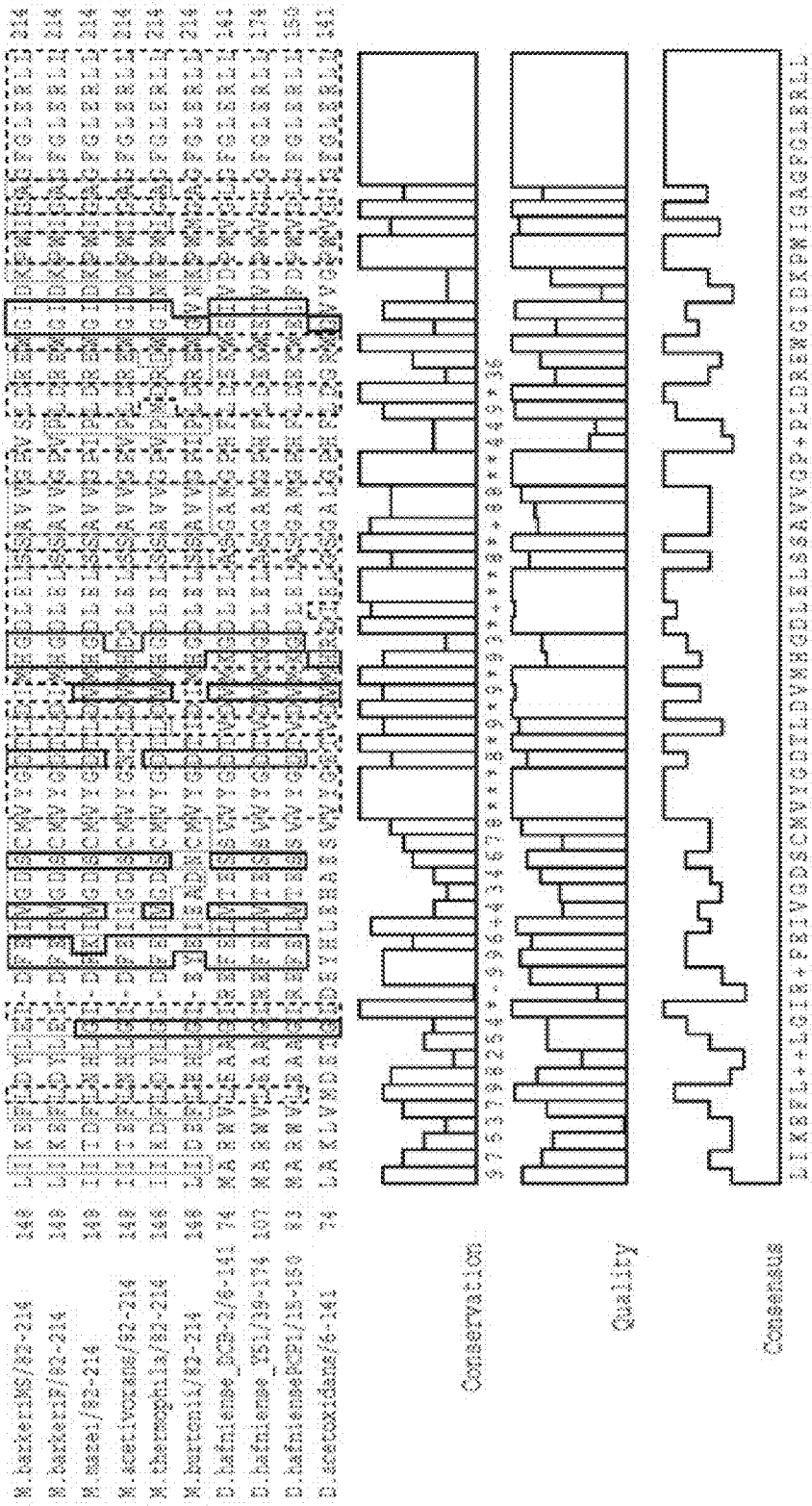
FIG. 7 shows alignment of the catalytic domain of PylS sequences (from 350 to 480; numbering from alignment of FIG. 5).

Cells were harvested 3 to 4 hours after induction of protein expression, washed with PBS and incubated with fluorophore probes at room temperature. After washing the cell pellets, the cells were lysed and the reaction mixtures were analyzed by SDS PAGE to assess proteome levels. Fluorescence scanning of SDS-PAGE gels revealed that the tetrazine-norbornene cycloaddition is highly specific for norbornene with respect to other *E. coli* proteins. Results are shown in FIG. 3D.

Example 1C: Application of Norbornene-Lysine Incorporation in the Site-Specific Modification of Proteins with Polyethylene Glycol Synthesis of a Norbornene-PEG Reagent:

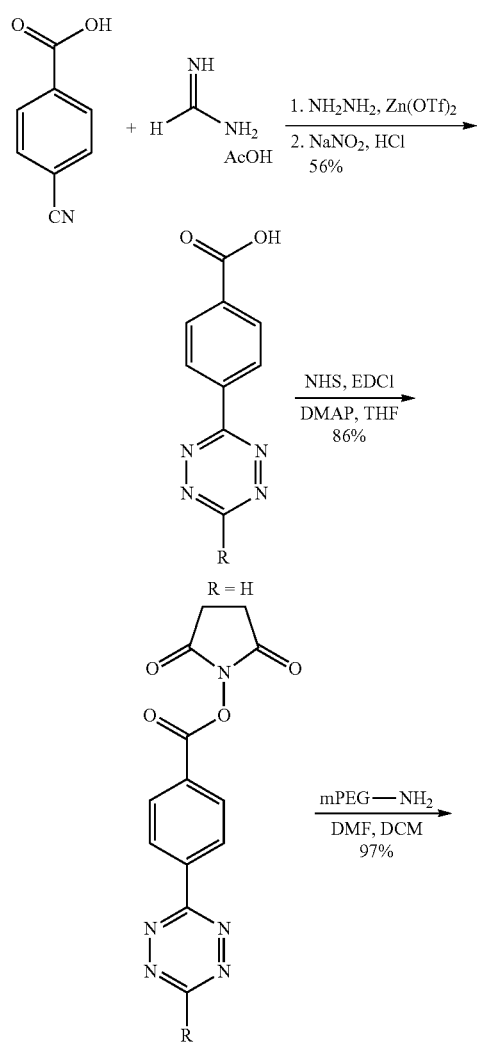

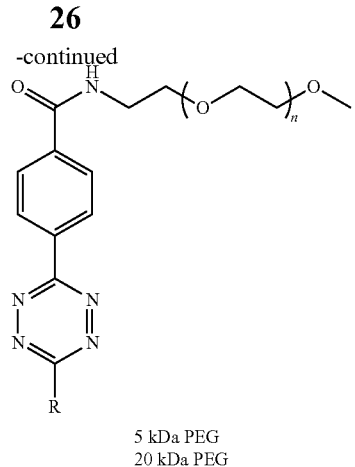

5 kDa PEG
20 kDa PEG

Two exemplary PEG-tetrazine reagents, a 5 kDa and a 20 kDa one (R=H), were synthesized in 3 steps from commercially available reagents following a published procedure for tetrazine assembly (Angew. Chem. Int. Ed. 2012, 51, 5222-5225).

Other R groups may be used in order to tune the reactivity of the tetrazine reagent, e.g., halides, alkanes, haloalkanes, arenes, heteroarenes, haloarenes, and others.

Other linear and branched PEG groups of different molecular weight (e.g., 1 kDa, 2 kDa, 40 kDa, 100 kDa) may also be used.

Alternative polymers (e.g., peptides, oligonucleotides, polyethylene, polyvinylchloride, polysaccharides, or others) could also be modified with one or multiple tetrazines and used in bioconjugations with proteins.

Figure 10A:
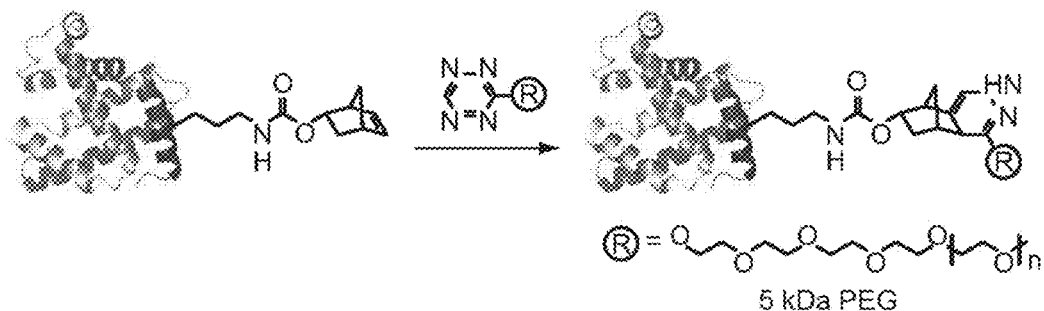
FIGS. 10A-C show diagrams and photographs of PEGylation.

Protein PEGylation Reaction:

FIG. 10A shows a schematic of the protein PEGylation reaction of a norbornene-protein and a tetrazine-PEG reagent.

Figure 10B:
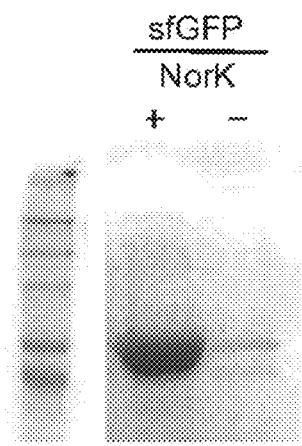

FIG. 10B shows PAGE gel showing purified superfolder-green fluorescent protein (sfGFP) containing the norbornene-lysine (NorK) incorporated at position 00 in a *E. coli* expression system.

Figure 10C:
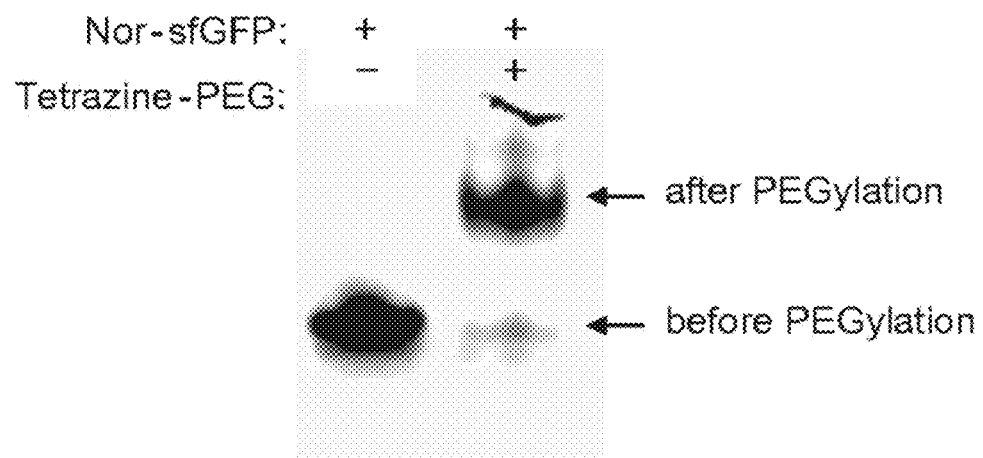

FIG. 10C shows PAGE gel (imaging GFP fluorescence) of the PEGylation reaction showing a distinct change in molecular weight of sfGFP through addition of a single PEG group.

Thus PEGylation according to the present invention is demonstrated.

Example 2

RESULTS and DISCUSSION

Synthesis and Genetic Encoding of a Norbornene Containing Amino Acid

Figure 1A:
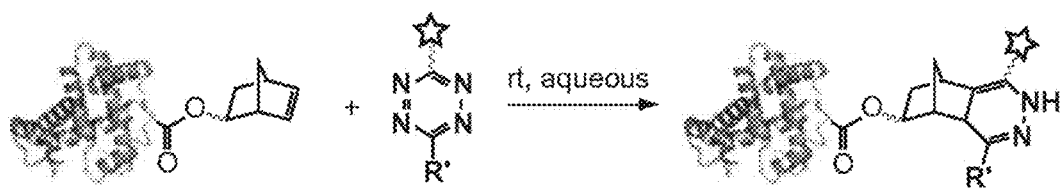
FIG. 1A shows genetically encoded norbornenes rapidly react with tetrazines in aqueous solution at ambient temperatures and pressures to site-specifically label proteins.
Figure 1B:
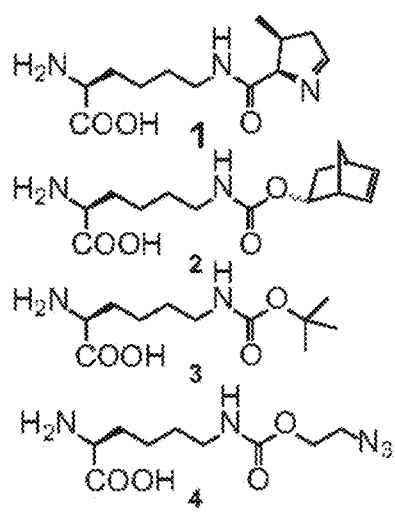
FIG. 1B shows the amino acid structures of pyrrolysine (1), Nε-5-norbornene-2-yloxy-carbonyl-L-lysine (2), Nε-tert-butyloxycarbonyl-L-lysine (3), and Nε-(2-azidoethyloxy-carbonyl-L-lysine (4).

The pyrrolysyl-tRNA synthetase/tRNACUA pair (PylRS/tRNACUA) from *Methanosarcina* species, which naturally incorporates pyrrolysine (1, FIG. 1B), is orthogonal to endogenous tRNAs and aminoacyl-tRNA synthetases in *E. coli* and eukaryotic cells.[39-42] Using this pair, and its synthetically evolved derivatives, we and others have directed the efficient incorporation of unnatural amino acids, including post-translationally modified amino acids, chemical handles, and photocaged amino acids, at specific sites in desired proteins in *E. coli*, yeast, and mammalian cells.[27,28,39,40,43-46] Moreover, we have recently demonstrated the incorporation of unnatural amino acids, using this pair, in a whole animal.[42] We envisioned that this synthetase/tRNA pair might be used to site-specifically and quantitatively incorporate a norbornene containing amino acid into proteins produced in diverse organisms, and that the norbornene containing protein could be rapidly and selectively labeled with tetrazine-based probes.

Figure 2A:
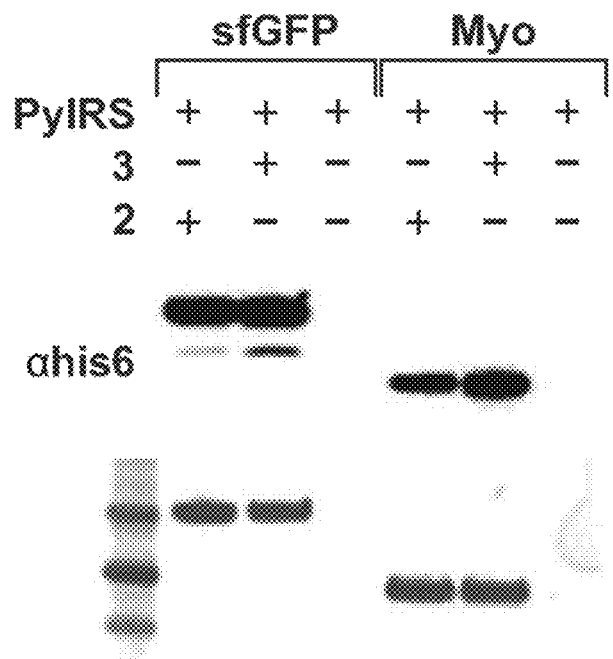
FIGS. 2A-B show the efficient, genetically-directed incorporation of 2 using the PylRS/tRNA$_{CUA}$ pair in *E. coli*.
Figure 2B:
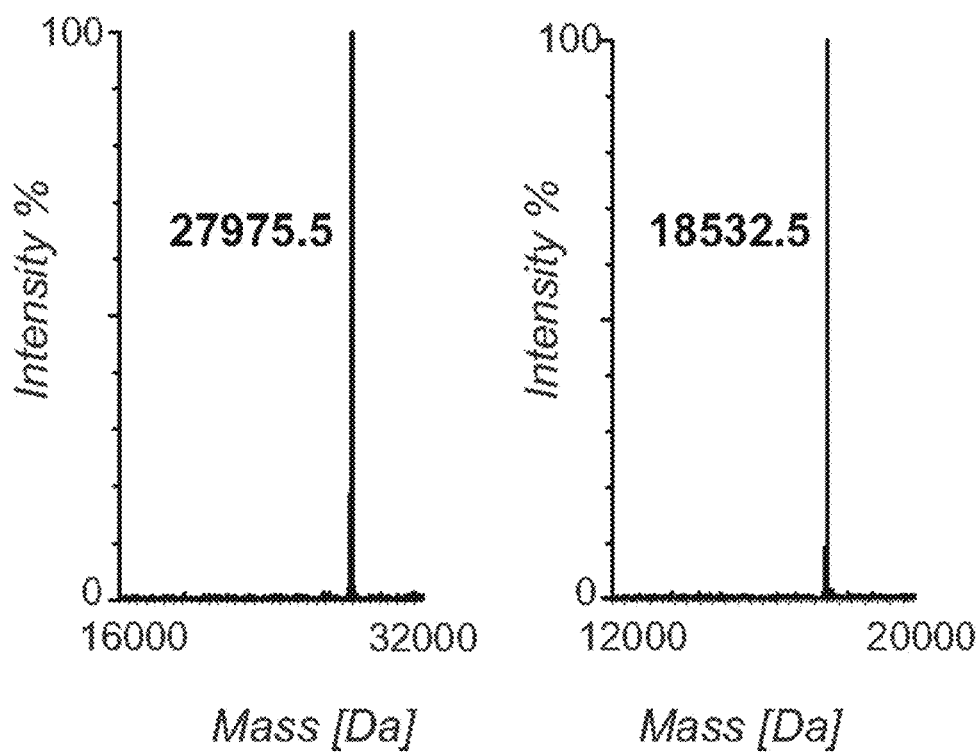
Figure 13:
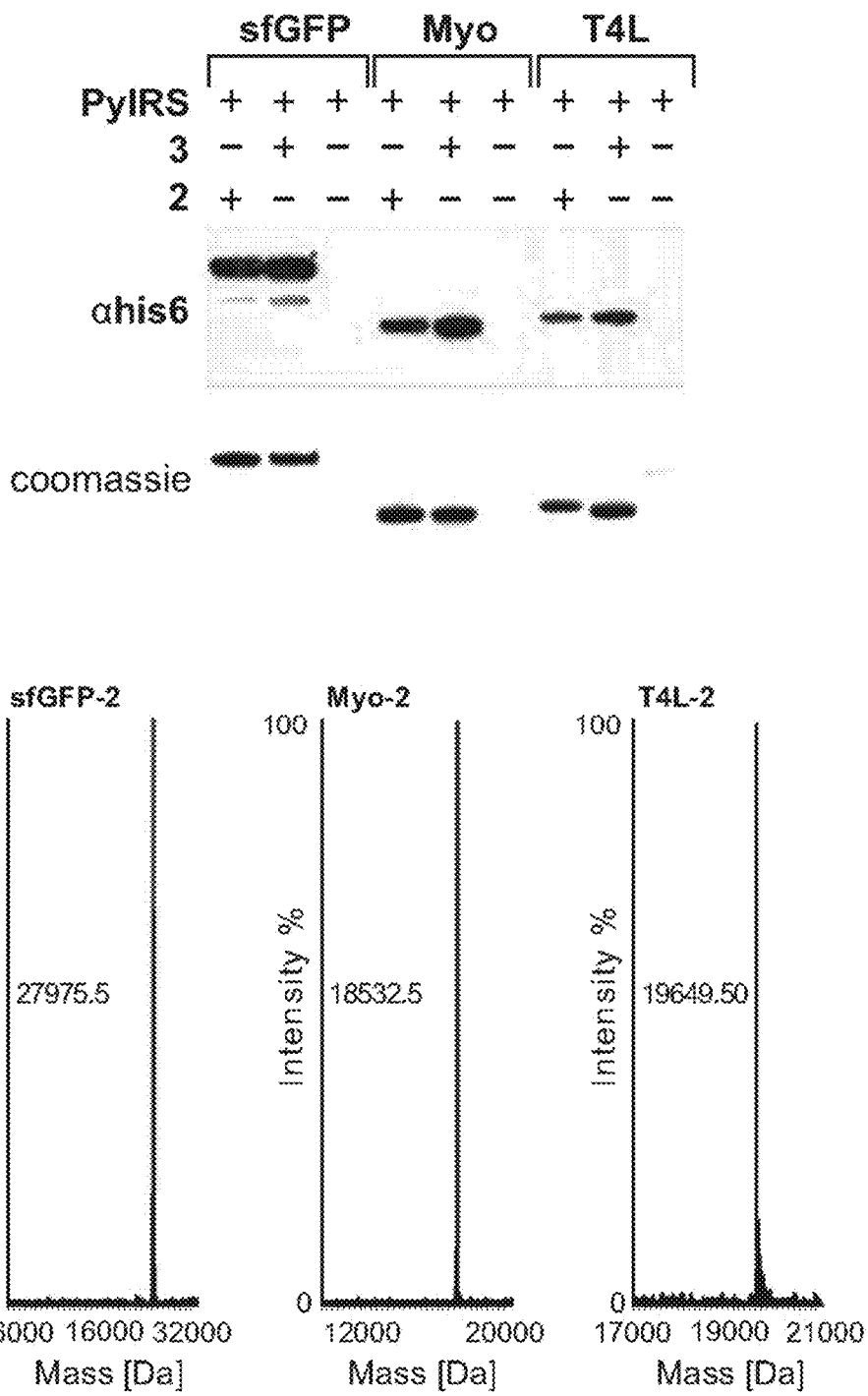
FIG. 13 shows myoglobin bearing an amber codon at position 4 and T4 lysozyme bearing an amber codon at position 83 produced good yields of protein in the presence, but not absence; the incorporation of 2 was further confirmed by electrospray ionization mass spectrometry of purified proteins.

We designed the norbornene containing amino acid N-ε-5-norbornene-2-yloxy-carbonyl-L-lysine (2, FIG. 1B) and synthesized it in three steps and 77% overall yield (Supplementary Information and Supplementary Scheme 1). To investigate whether 2 is a substrate for the MbPylRS/tRNACUA pair we transformed E. coli with pBKPylS (which endcodes MbPylRS) and psfGFP150TAGPylT-His6 (which encodes MbtRNACUA and a C-terminally hexahistidine tagged sfGFP gene with an amber codon at position 150). In the presence of 2 (1 mM), full-length sfGFP was isolated in good yield (FIG. 2, 4 mg L$^{-1}$ of culture), which is comparable to the yields for other well-incorporated unnatural amino acids.[28,32,45] GFP expression was clearly amino acid dependent. Similarly, myoglobin bearing an amber codon at position 4 and T4 lysozyme bearing an amber codon at position 83 produced good yields of protein in the presence, but not absence, of 2 (FIG. 2 and FIG. 13). The incorporation of 2 was further confirmed by electrospray ionization mass spectrometry of purified proteins (FIG. 2 and FIG. 13)

Synthesis of Biocompatible Tetrazines

Figure 1C:
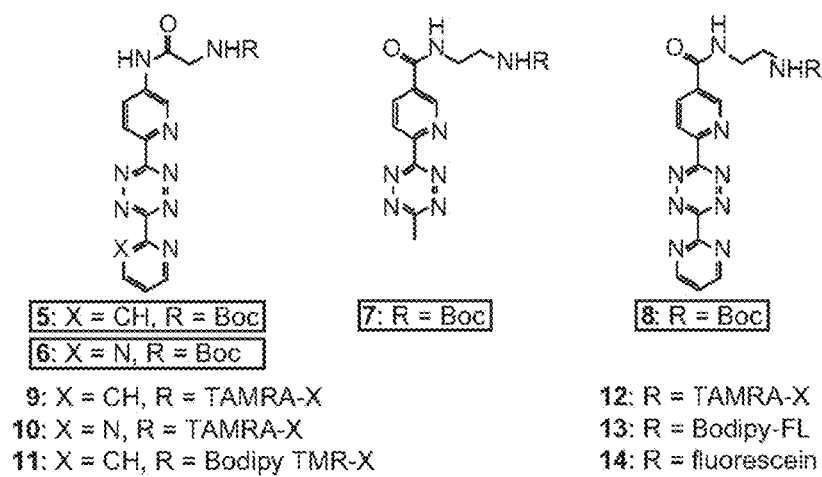
FIG. 1C shows structures (5-14) of tetrazines and tetrazine-fluorophores used in this study.

To create unsymmetrical tetrazines that contain a unique reactive group for functionalization with biophysical probes (FIG. 1C, Supplementary Scheme 2 and Supplementary Information) we reacted equimolar quantities of 5-amino-2-cyanopyridine and 2-cyanopyridine (or 2-cyanopyrimidine) with an excess of aqueous hydrazine to obtain s-dihydrotetrazines S5a and S6a.[36] Treatment of these dihydrotetrazines with a mixed anhydride formed in situ from isobutylchloroformate and N-tert-butyloxycarbonyl-glycine afforded compounds S5b and S6b, respectively, which were readily oxidized to their corresponding tetrazines 5 and 6 with sodium nitrate in acetic acid. Acidic deprotection of the tert-butyloxycarbonyl groups afforded tetrazines S5c and S6c.[47] The primary amino group in these tetrazine derivatives provides a handle for further functionalization with biophysical probes.

We envisioned that analogs of 5 and 6 bearing a carboxy group in place of the amine would be more electrodeficient, and potentially more reactive in inverse electron demand cycloadditions with norbornenes. To create tetrazines 7 and 8, we reacted N-tert-butyloxycarbonylethylenediamine with 6-cyanopyridine-3-carboxylic acid under standard amide-coupling conditions. The resulting nitrile S7a was reacted with acetonitrile or 2-cyanopyrimidine in aqueous hydrazine to give dihydrotetrazines S7b and S8b, respectively, which after sodium nitrate oxidation afforded tetrazines 7 and 8. Deprotection of 8 under acidic conditions gave tetrazine S8c. The primary amino group in this tetrazine derivative provides a handle for further functionalization with biophysical probes. All the tetrazines synthesized are stable in MeOH/H$_2$O and DMSO/H$_2$O at room temperature for several days as judged by LCMS (data not shown).

Kinetic Analysis of the Rapid Tetrazine Diels Alder Cycloaddition

Figure 14:
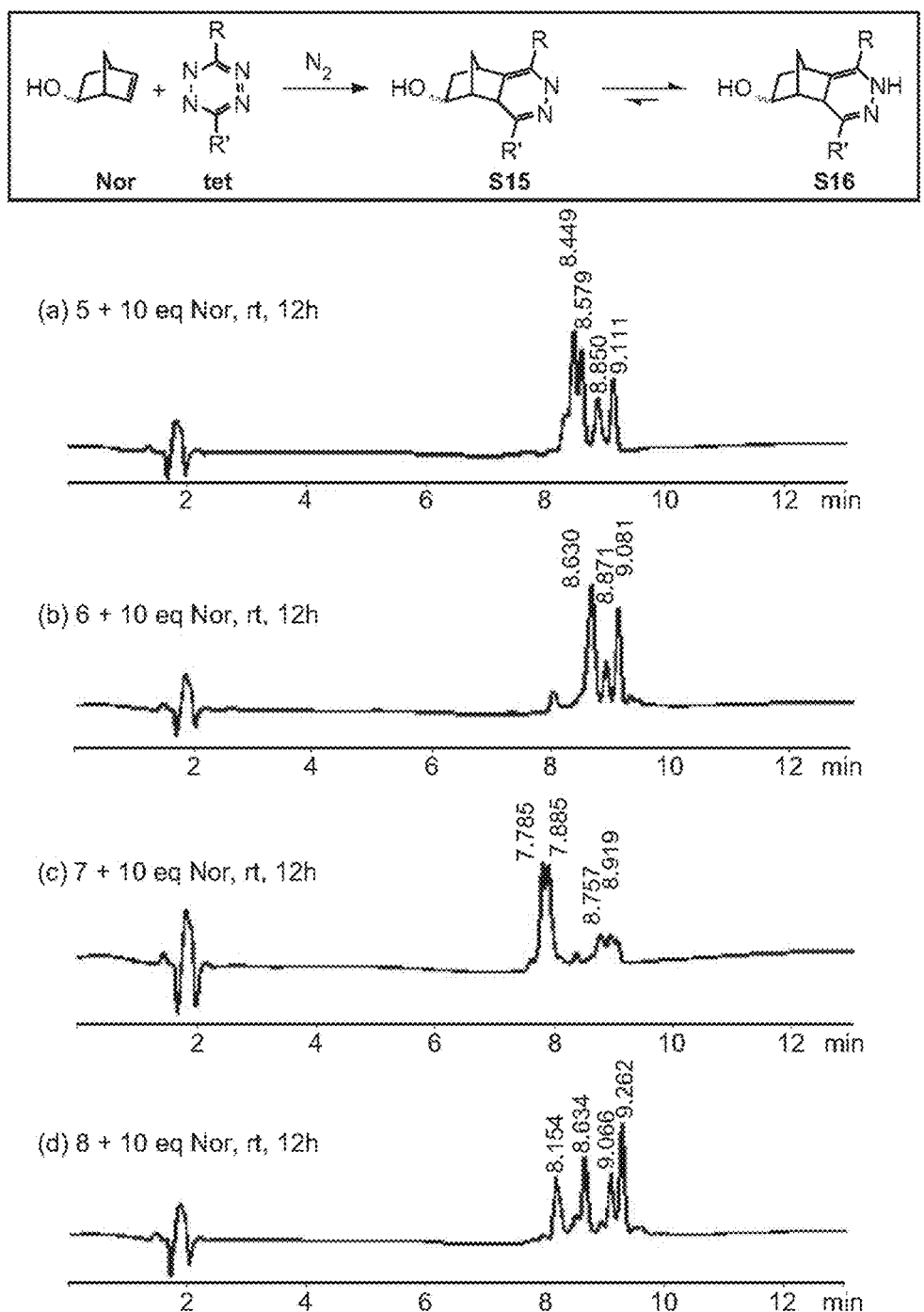
FIG. 14 shows that the tetrazines (5-8) readily react with 5-norbornene-2-ol to form the corresponding dihydropyridazines S15 and its isomeric forms S16 in protic solvents in >96% conversion.
Figure 15C:
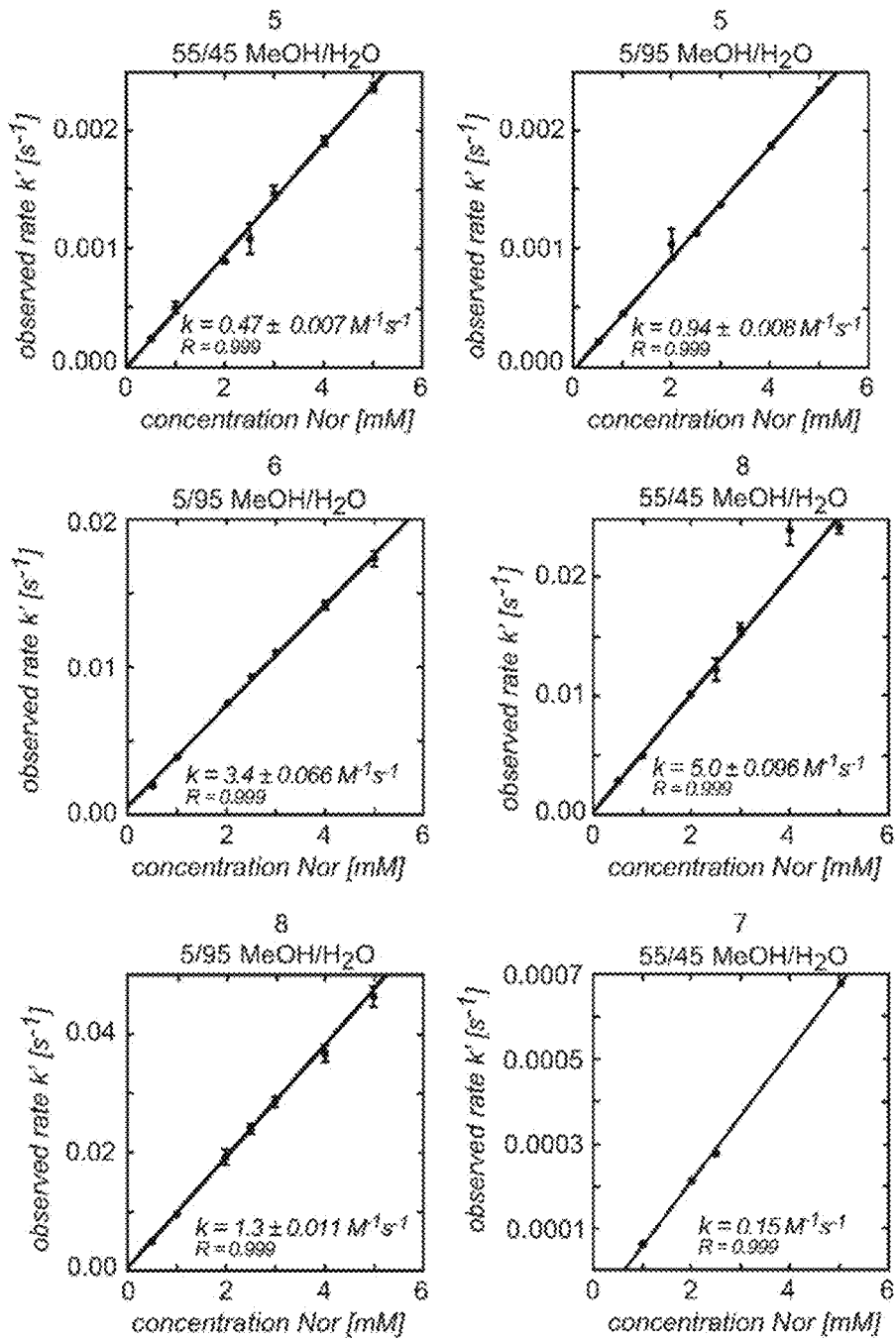

The tetrazines (5-8) readily react with 5-norbornene-2-ol to form the corresponding dihydropyridazines S15 and its isomeric forms S16 in protic solvents in >96% conversion (FIG. 14 and Supplementary Information). The rate constants for these reactions were determined under pseudo-first order conditions by following the exponential decay in the UV absorbance of the tetrazine at 320 or 300 nm over time (FIGS. 15A-C). The reactions were faster in more polar solvent systems, i.e., solvent mixtures with higher water content, as expected.[36,48]

Tetrazine 8 displays the highest activity towards 5-norbornene-2-ol with second order rate constants of approximately 9 M$^{-1}$ s$^{-1}$ in H$^2$O/MeOH (95:5) at 21° C., while 5 reacts with a rate constant of approximately 1 M$^{-1}$ s$^{-1}$ under the same conditions (FIG. 16A and Supplementary Information). This confirms that the tetrazine norbornene reaction is orders of magnitude faster than established bioorthogonal reactions.[30]

Tetrazine-Based Fluorophores—'Turn-On' Fluorogenic Probes

Figure 17:
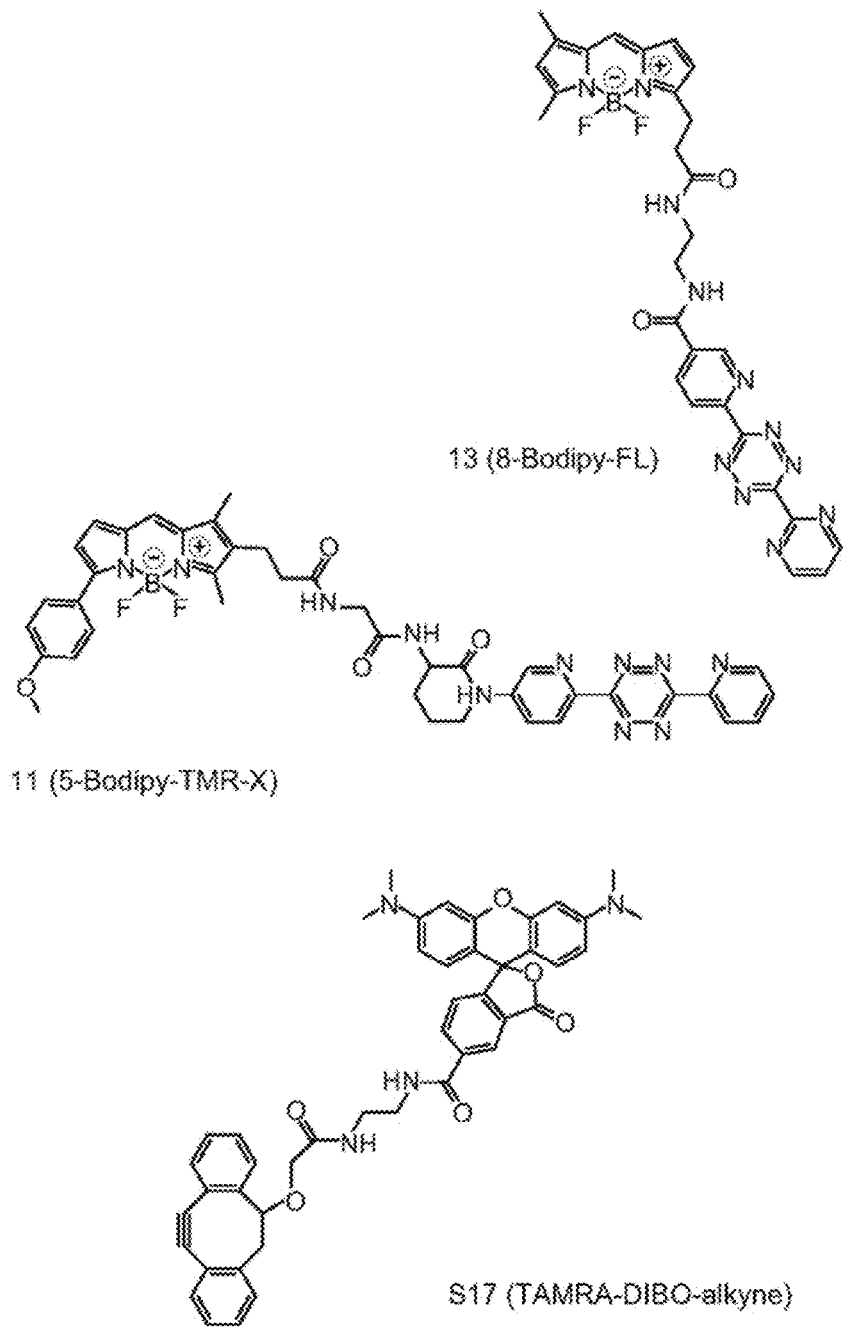
FIG. 17 shows the chemical structures of 9-14 and S17.
Figure 18:
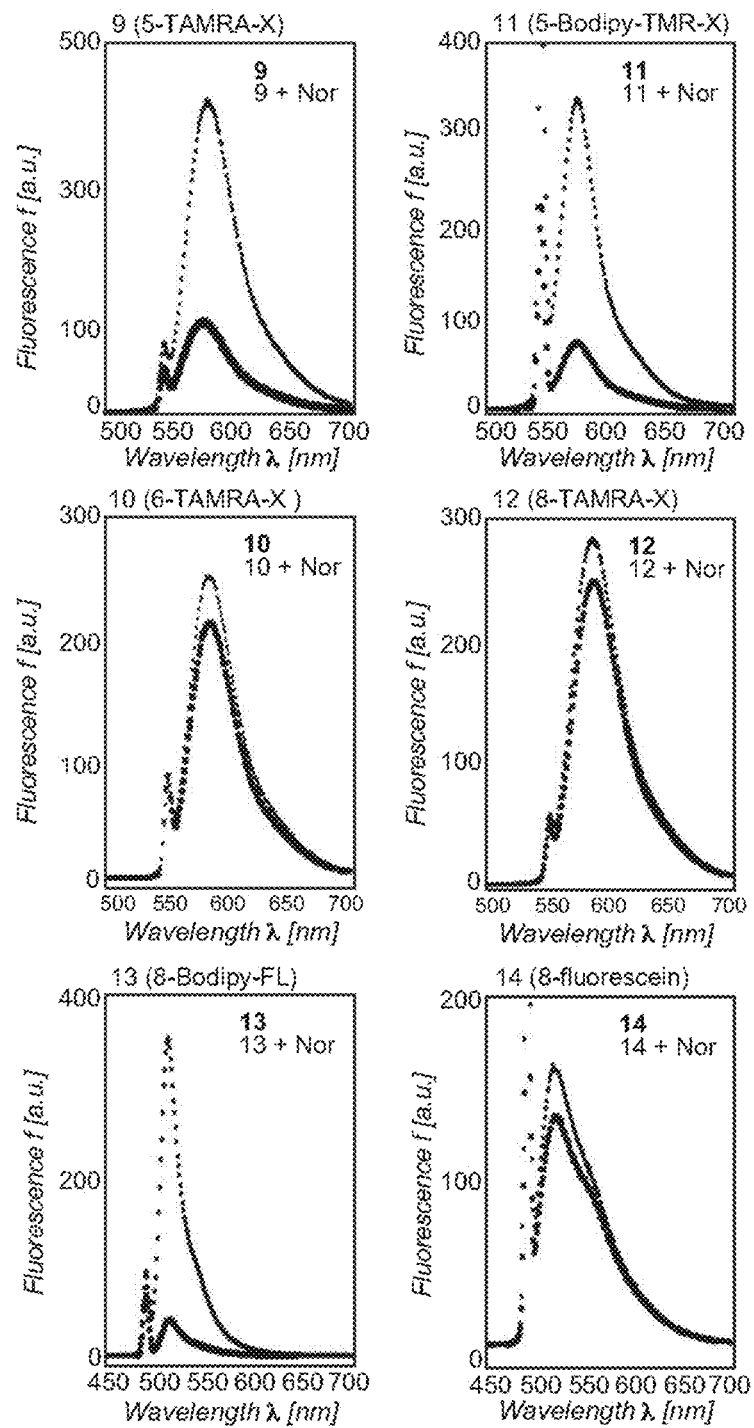
FIG. 18 shows fluorescence spectra of compounds 9-14.

To create fluorescent probes based on 5, 6, and 8, the primary amino groups of S5c, S6c, and S8c were conjugated to succinimidylesters or isothiocyanates of fluorescein, tetramethylrhodamine (TAMRA), and boron-dipyrromethene (BODIPY) dyes (Supplementary Information, FIGS. 17-18, FIG. 16B).

The fluorescence of the visible light-emitting TAMRA tetrazine conjugate 9 and BODIPY tetrazine conjugate 10 were substantially reduced with respect to the fluorescence of the succinimidyl or isothiocyanate derivatives of the parental fluorophores. This is in agreement with recent work showing that fluorophores can be quenched by energy transfer to a proximal tetrazine chromophore which absorbs between 510 and 530 nm.[49] However, despite 5, 6, and 8 having very similar absorption spectra, the fluorescence reduction of the dye-conjugates was dependent on the specific combination of tetrazine and fluorophore. For example, 9 (5-TAMRA-X) showed a much greater fluorescence reduction with respect to the parent TAMRA-X than 10 (6-TAMRA-X) and 12 (8-TAMRA-X). Fluorescein (emission maximum at 518 nm) was minimally quenched by conjugation to 8. The fluorescence of 9, 11, and 13 was turned on upon cycloaddition with 5-norbornene-2-ol, leading to a 5-10 fold gain in fluorescence intensity (FIG. 3A, FIG. 18).

Figure 19:
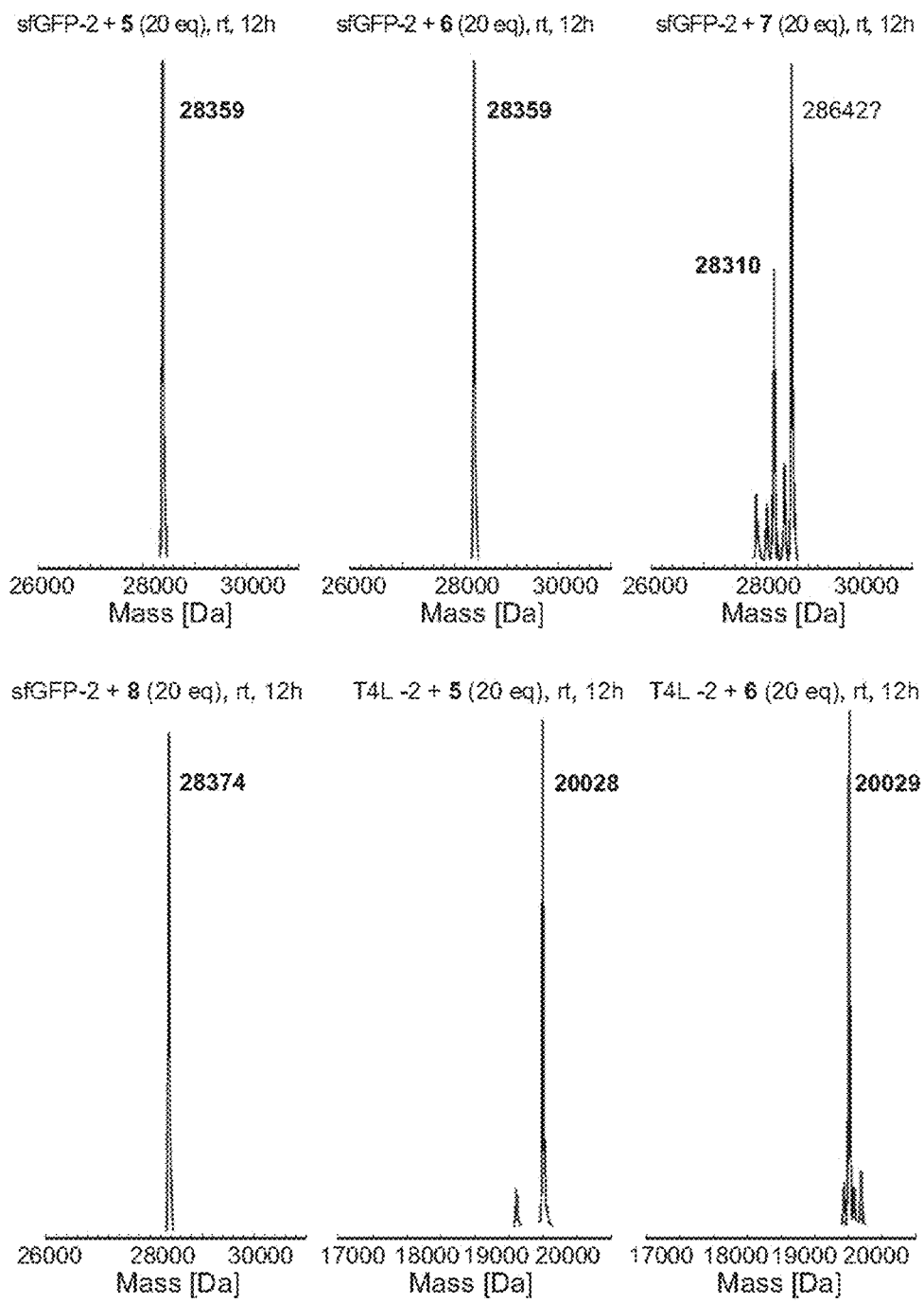
FIG. 19 shows the mass spectra of aliquots taken from the in vitro labeling of purified proteins with different tetrazines.
Figure 19:
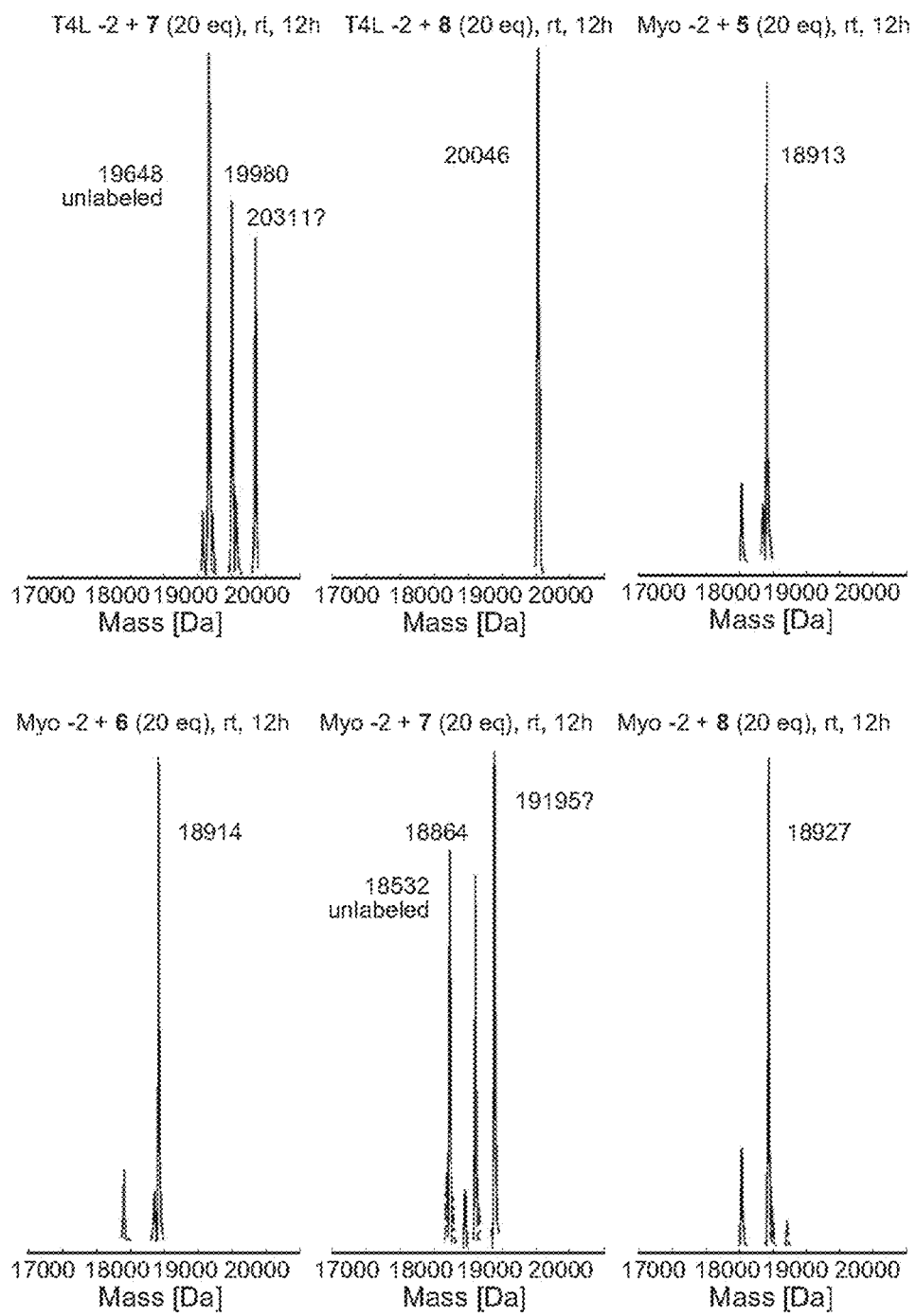
Figure 20A:
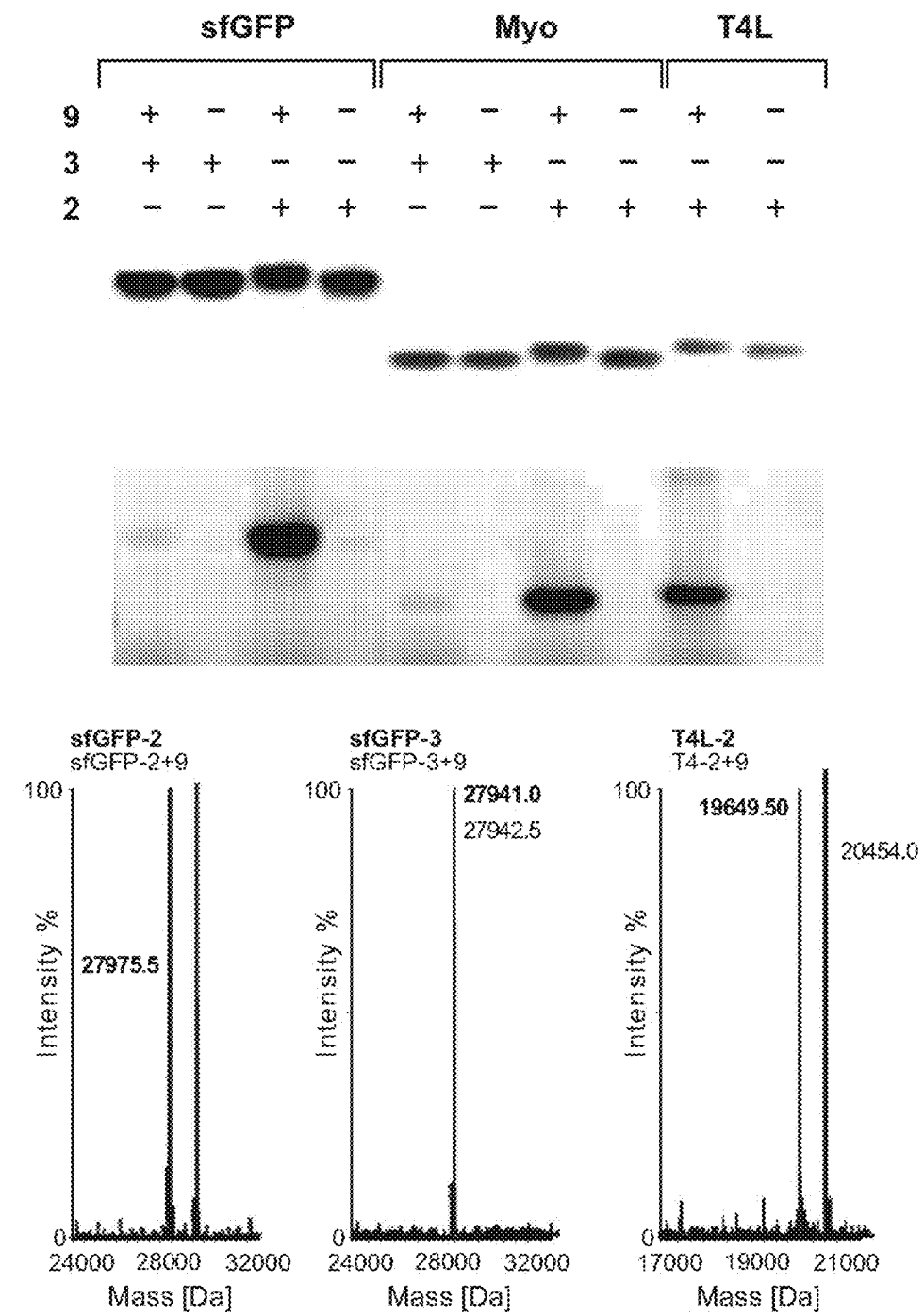
FIGS. 20A-B show SDS-PAGE based fluorescence imaging (FIG. 20A) and ESI-MS analysis (FIG. 20B) of purified sfGFP-2, Myo-2 and T4L-2 incubated overnight with fluorophore 9.
Figure 20B:
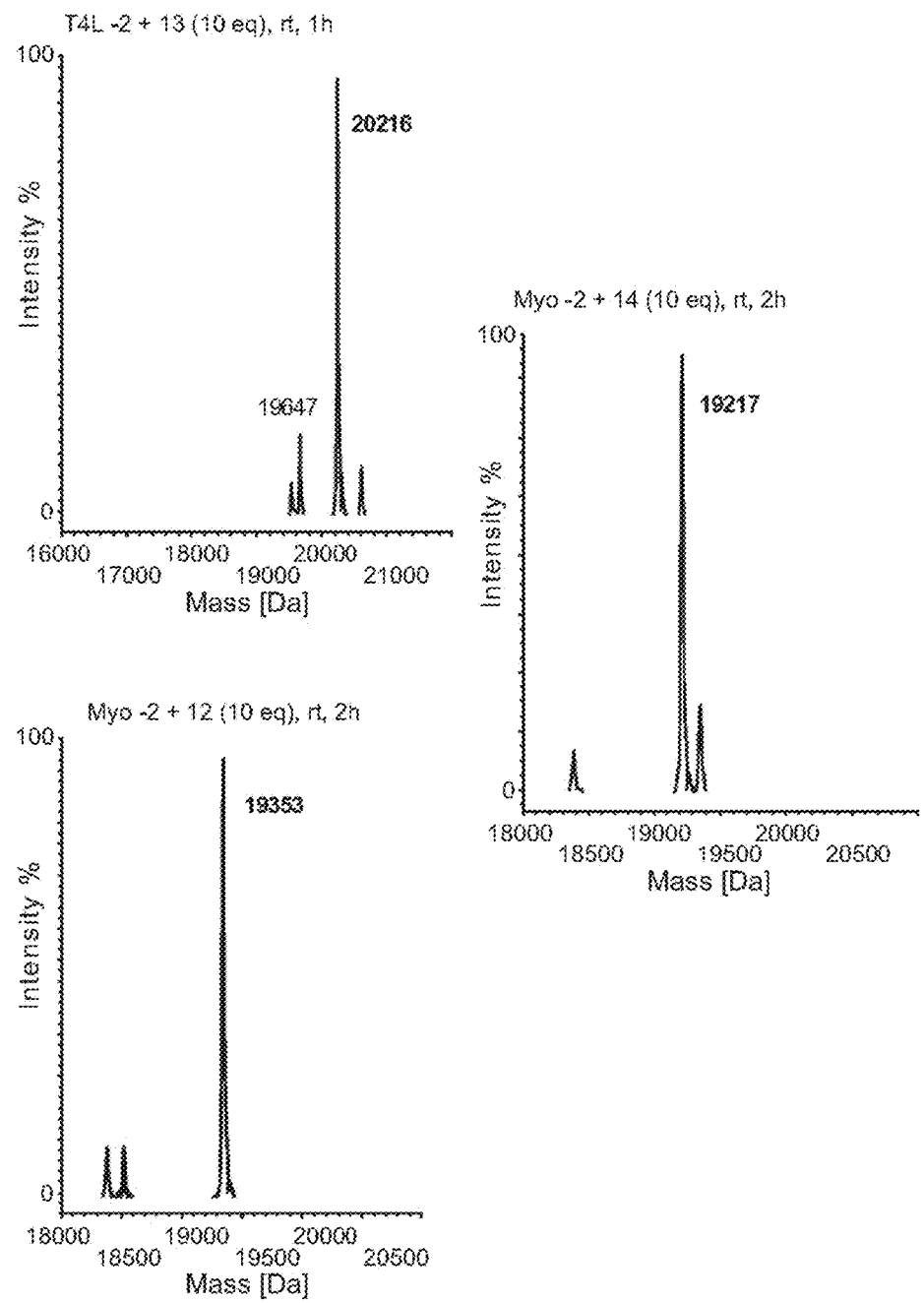

Rapid In Vitro Labeling of Norbornene Containing Proteins with Tetrazine-Based Probes To demonstrate that our tetrazine-dye probes react efficiently and specifically with recombinant proteins bearing site-specifically incorporated 2, purified sfGFP-2, Myo-2 and T4L-2 were incubated overnight with fluorophore 9 (10 equiv.) at room temperature. SDS-PAGE based fluorescence imaging and ESI-MS analysis (FIG. 3A and FIGS. 20A-B) confirmed quantitative labeling of the proteins containing 2 whereas no nonspecific labeling was detected with the control proteins containing NE-tert-butyloxycarbonyl-L-lysine (3) in place of 2 at the same site. In additional experiments we showed the specific and quantitative labeling of proteins containing 2 with tetrazine derivatives 5, 6, and 8, as well as with tetrazine fluorophores 12, 13 and 14 by mass spectrometry (FIGS. 19, 20A-B). Previous labeling experiments of proteins containing unnatural amino acids with specific fluorophores required washing steps to remove free dye that is non-covalently associated with the protein. Here, we found that we can image the specific labeling of proteins containing 2 without washing the sample or the gel; this improvement may—at least in part—result from the "turn on" fluorescence of the tetrazine fluorophores.

Figure 21:
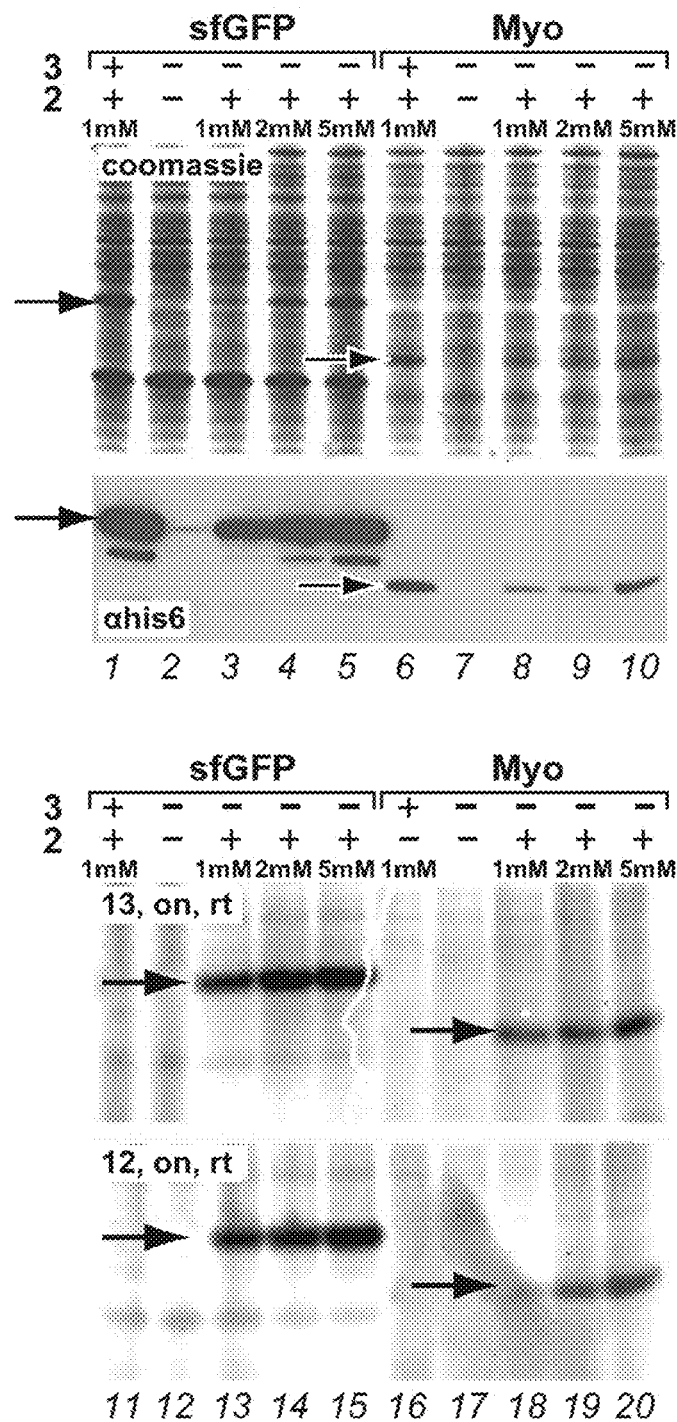
FIG. 21 shows the specificity of labeling 2 in sfGFP-2 and Myo-2 versus the *E. coli* proteome.

To further probe the specificity of the reaction between the genetically encoded norbornene and the tetrazine-based fluorophores we performed the labeling reaction on the proteome of E. coli expressing either sfGFP-2-His6 or Myo-2-His6 (FIG. 3D and FIG. 21). We controlled the level of recombinant protein expression so that it was equal to or less than that of many endogenous proteins by modulating the concentration of 2 added to cells; this ensures that any specific labeling of the target protein versus native proteins is not an artifact of the abundance of the target protein. Cells were harvested 3.5 hours after induction of protein expression, washed with PBS and incubated with fluorophore probes (12 or 13) at room temperature. After washing the cell pellets, the cells were lysed and the reaction mixtures were analyzed by SDS PAGE to assess protein levels. Fluorescence scanning of SDS-PAGE gels revealed that the tetrazine-norbornene cycloaddition is highly specific for 2 with respect to other *E. coli* proteins.[50]

To demonstrate that the high rate constants measured on small molecules translate into rapid protein labeling, we labeled myoglobin bearing 2 at position 4 with 12 (10 equivalents). In gel fluorescence imaging of the labeling reaction as a function of time (FIG. 3C) demonstrates that the reaction is complete in approximately 30 minutes. Rapid labeling of proteins incorporating 2 is also observed with probes 9 and 12 (FIG. 22). In contrast, the labeling of an alkyne containing amino acid at the same site in myoglobin requires 50 equivalents of azide fluorophore and 18 hours to reach completion in a copper catalyzed click reaction.[28] This demonstrates that the labeling method we report has a clear advantage for the labeling of recombinant proteins.

Site-Specific Protein Labeling on the Mammalian Cell Surface

While it has been possible to label abundant molecules at multiple chemical handles on cell surfaces via metabolic incorporation of bio-orthogonal functional groups[33-35] there are no reports of labeling single, genetically defined sites on proteins on the mammalian cell surface using any of the unnatural amino acids that can currently be genetically encoded.

Figures 23A, 23B:
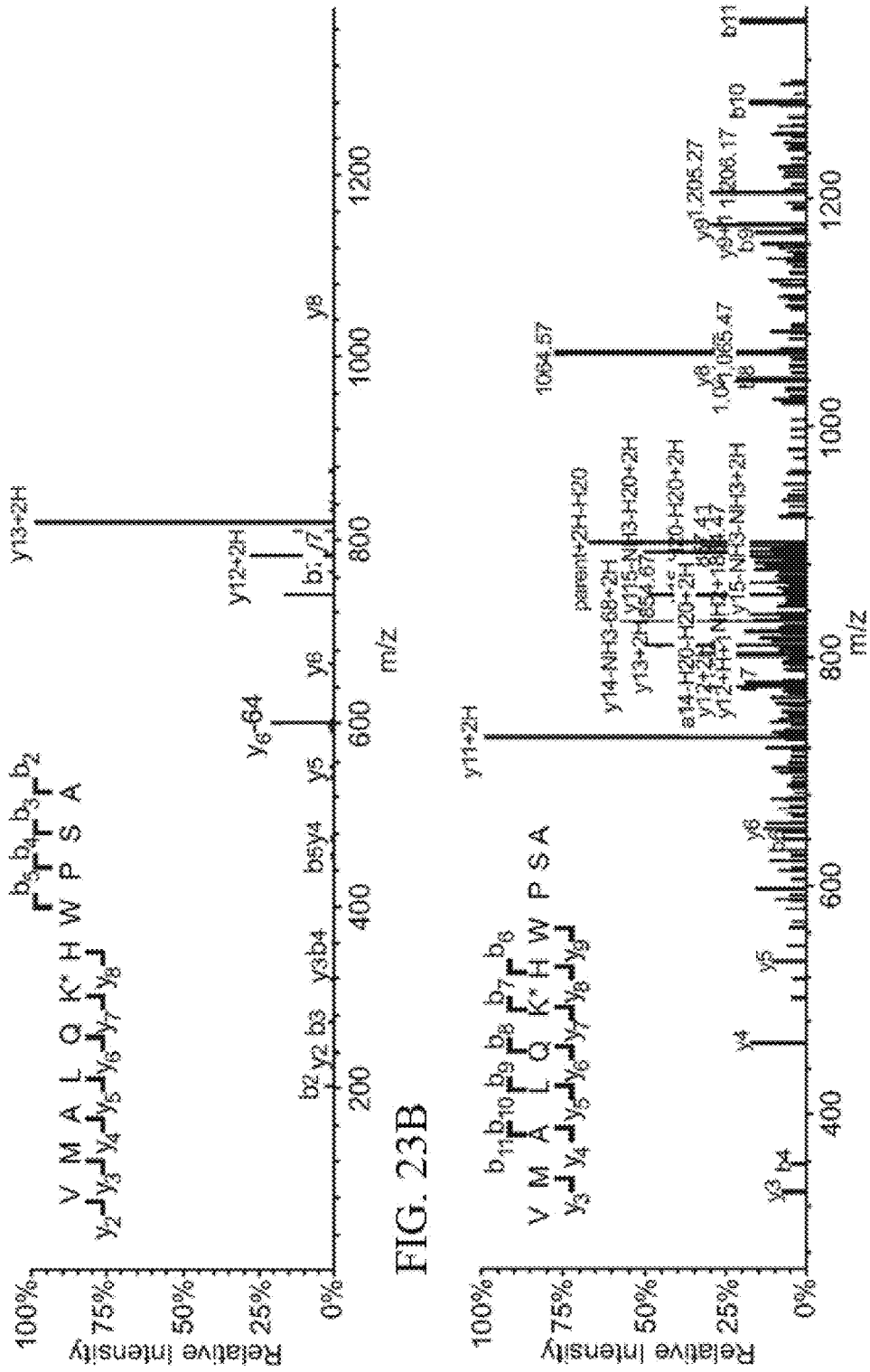
FIGS. 23A-B show MS/MS data from the incorporation of 2 into proteins in mammalian cells.
Figure 24:
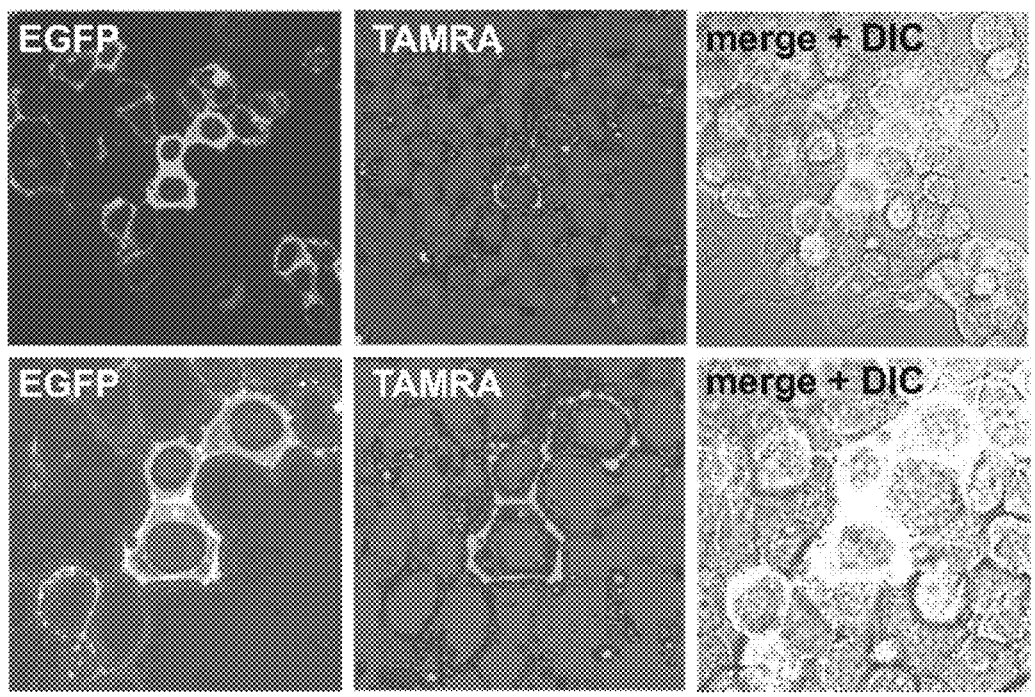
FIG. 24 shows specific and rapid labeling of EGFR-2-GFP in mammalian cells with a tetrazine-based fluorophore 9 (2 h).

We demonstrated that 2 can be genetically encoded with high efficiency into proteins in mammalian cells using the MmPylRS/tRNACUA pair by western blot, fluorescence imaging and mass spectrometry[46] (FIG. 4 and FIGS. 23A-B). To show the site-specific labeling of a mammalian protein, we introduced an amber codon into an EGFR (epidermal growth factor receptor)-GFP fusion gene at position 128, in the extracellular portion of the receptor in a vector containing MmPylRS, creating pMmPylRS-EGFR (128TAG)-GFP-HA. We transfected HEK293 cells with pMmPylRS-EGFR(128TAG)-GFP-HA and p4CMVE-U6-PylT that encodes four copies of the MmPyltRNACUA. In the presence of 2 or 3 cells produced full length EGFR-GFP that can be visualized at the cell membrane by fluorescence microscopy. To demonstrate the specific labeling of EGFR-GFP containing 2 with tetrazine-fluorophores we treated cells with 9 (200 nM), washed the cells and imaged the red fluorescence arising from TAMRA-labeling as well as green fluorescence arising from expression of full-length EGFR-GFP, in which the C-terminal GFP is intracellular. Clear labeling of cells bearing EGFR-2-GFP was observed within 2 hours and TAMRA fluorescence clearly co-localized with cell surface EGFR-GFP fluorescence. No labeling was observed for cells in the same sample that did not express EGFR-GFP, and cells bearing EGFR-3-GFP were not labeled with 9. These observations confirm that 2 at position 128 of EGFR is specifically labeled with the tetrazine-TAMRA conjugate 9 (FIG. 4 and FIGS. 24-27).

Figure 28:
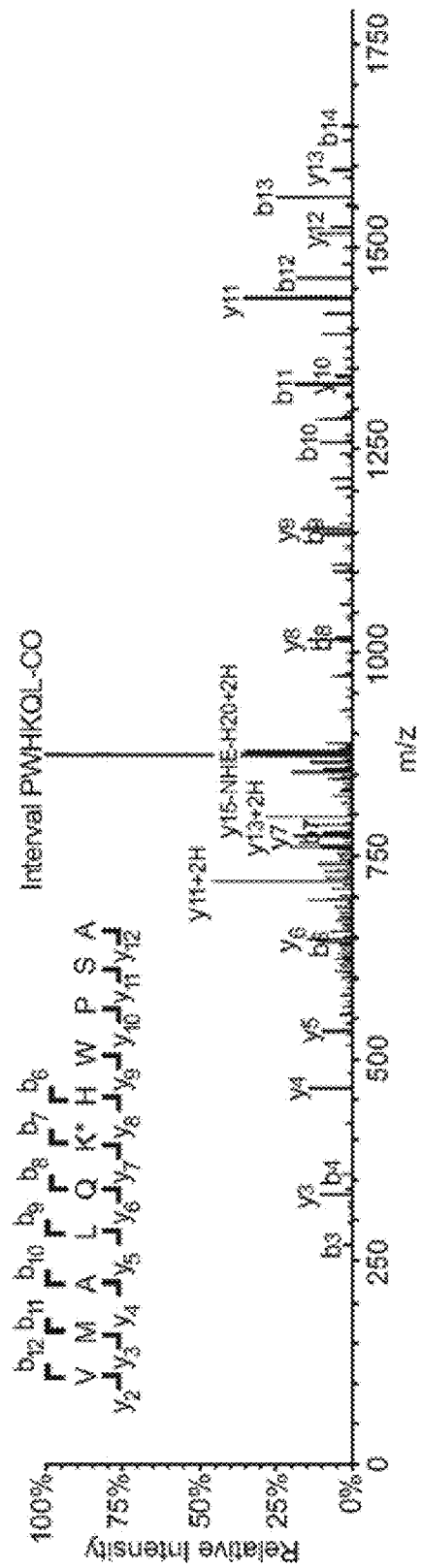
FIG. 28 shows MS/MS data showing the incorporation of 4 into proteins in mammalian cells.
Figure 29:
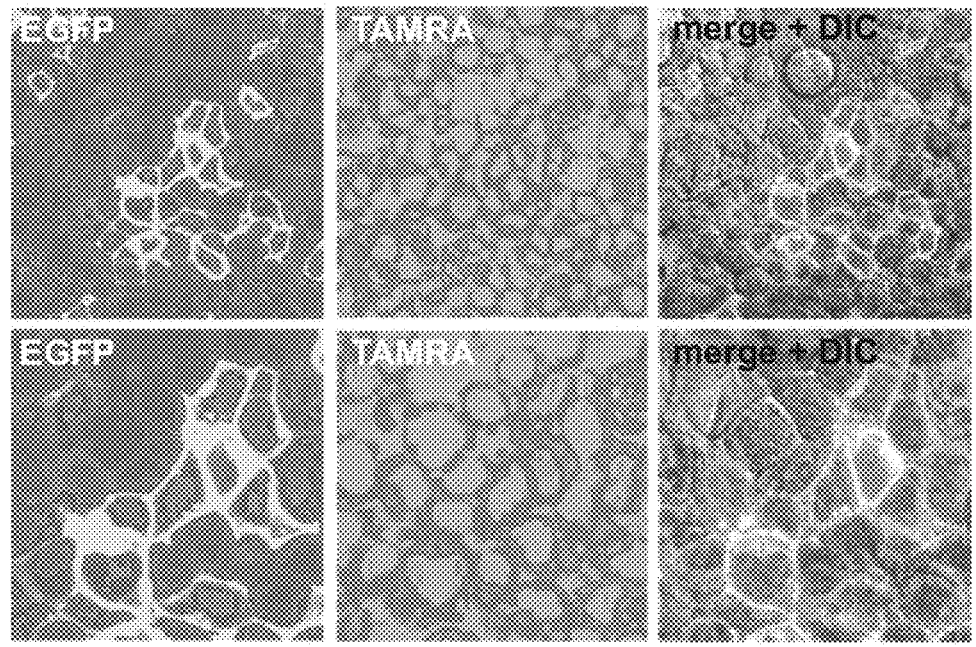
FIG. 29 shows labeling attempt (S17, TAMRA-DiBO-alkyne commercially available from Invitrogen) of EGFR-4-GFP in mammalian cells with a cyclooctyne-based fluorophore.
Figure 30:
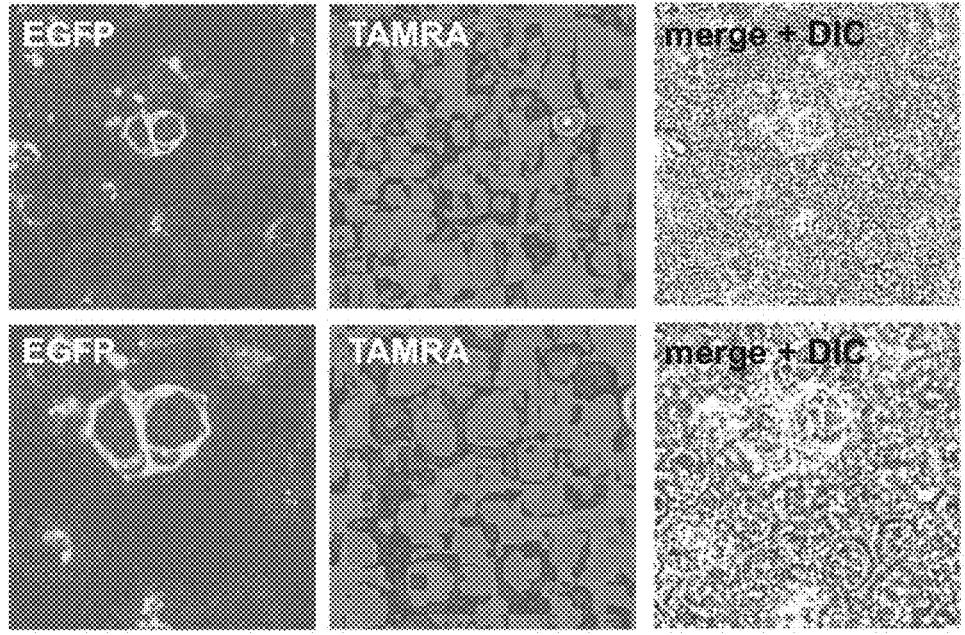
FIG. 30 shows labeling attempt of EGFR-4-GFP in mammalian cells with a cyclooctyne-based fluorophore using conditions provided by the supplier.

Next we aimed to compare the site specific tetrazine labeling of 2 on the surface of mammalian cells with the labeling of a site specifically incorporated azide, using a cyclooctyne, a reaction that has previously been used to successfully label azides installed into cell surface glycans and throughout the proteome.[33,34] We first demonstrated that an azide containing amino acid N☐-(2-azidoethyloxy-carbonyl-L-lysine (4, FIG. 1B), can be efficiently incorporated into proteins in mammalian cells using the PylRS/tRNACUA pair (FIG. 28). We then incorporated 4 into EGFR-GFP at position 128. 4 was incorporated with a comparable efficiency to 2, as judged by GFP fluorescence. However when we attempted to label 4 with a cyclooctyne based fluorophore (S17, TAMRA-DiBO-alkyne commercially available from Invitrogen, FIG. 17), under identical conditions used to label 2 with tetrazine-fluorophores we did not observe specific labeling (FIG. 29). Similarly, when we attempted to label 4 under conditions provided by the supplier we did not observe specific labeling of cell surface EGFR (FIG. 30). These results suggest that the faster rates of norbornene-tetrazine reactions translate into a clear advantage in protein labeling on the mammalian cell surface.

CONCLUSIONS AND OUTLOOK

In conclusion, we report the efficient synthesis and site-specific, genetically encoded incorporation of the norbornene containing amino acid 2 into proteins in *E. coli* and mammalian cells. We describe the development of a series of tetrazine-based probes that exhibit ""turn-on"" fluorescence upon their rapid reaction with norbornenes. We demonstrate that proteins bearing 2 can be specifically labeled in vitro, in complex mixtures and on the surface of mammalian cells and explicitly demonstrate the advantage of this approach for site specific protein labeling.

Methods

Protocols for chemical synthesis of norbornene lysine 2 and various tetrazine probes can be found in the Supplementary Information.

Protein Expression and Purification

To express sfGFP with an incorporated unnatural amino acid, we transformed *E. coli* DH10B cells with pBKPylS (which endcodes MbPylRS) and psfGFP150TAGPylT-His$_6$ (which encodes MbtRNA$_{CUA}$ and a C-terminally hexahistidine tagged sfGFP gene with an amber codon at position 150). Cells were recovered in 1 ml of S.O.B media (supplemented with 0.2% glucose) for 1 h at 37° C., before incubation (16 h, 37° C., 230 r.p.m) in 100 ml of LB containing kanamycin (50 μg/mL) and tetracycline (25 μg/mL). 20 ml of this overnight culture was used to inoculate 1 L of LB supplemented with kanamycin (25 μg/mL) and tetracycline (12 μg/mL) and incubated at 37° C. At OD$_{600}$=0.4 to 0.5, a solution of 2 in H$_2$O was added to a final concentration of 2 mM. After 30 min, protein expression was induced by the addition of arabinose to a final concentration of 0.2%. After 3 h of induction, cells were harvested by centrifugation and frozen at −80° C. until required. Cells were thawed on ice and suspended in 30 ml of lysis buffer (10 mM Tris-HCl, 20 mM imidazole, 200 mM NaCl, pH 8, 1 mM phenylmethanesulfonylfluoride, 1 mg/mL lysozyme, 100 μg/mL DNaseA, Roche protease inhibitor). Proteins were extracted by sonication at 4° C. The extract was clarified by centrifugation (20 min, 21.000 g, 4° C.), 600 μL of Ni$^{2+}$-NTA beads (Qiagen) were added to the extract and the mixture was incubated with agitation for 1 h at 4° C. Beads were collected by centrifugation (10 min, 1000 g). The beads were three times resuspended in 30 mL wash buffer (10 mM Tris-HCl, 20 mM imidazole, 200 mM NaCl, pH 8) and spun down at 1000 g. Subsequently, the beads were resuspended in 10 mL of wash buffer and transferred to a column. The protein was eluted with 3 ml of wash buffer supplemented with 200 mM imidazole and further purified by size-exclusion chromatography employing a HiLoad 16/60 Superdex 75 Prep Grade column (GE Life Sciences) at a flow rate of 1 mL/min (buffer: 20 mM Tris-HCl, 100 mM NaCl, pH 7.4). Fractions containing the protein were pooled and concentrated with an Amicon Ultra-15 3 kDa MWCO centrifugal filter device (Millipore). Purified proteins were analyzed by 4-12% SDS-PAGE. Sperm whale myoglobin and T4 Lysozyme with incorporated 2 were prepared in the same way, except that cells were transformed with pMyo4TAGPylT-His6 (which encodes MbtRNACUA and a C-terminally hexahistidine tagged sperm whale myoglobin gene with an amber codon at position 4) and pBKPylS or pT4L83TAGPylT-His$_6$ (which encodes MbtRNA$_{CUA}$ and a C-terminally hexahistidine tagged T4 lysozyme gene with an amber codon at position 83) and pBKPylS. Yields of purified proteins were up to 4 mg/L.

Protein Mass Spectrometry

Using an Agilent 1200 LC-MS system, ESI-MS was carried out with a 6130 Quadrupole spectrometer. The solvent system consisted of 0.2% formic acid in H$_2$O as buffer A, and 0.2% formic acid in acetonitrile (MeCN) as buffer B. LC-ESI-MS on proteins was carried out using a Phenomenex Jupiter C4 column (150×2 mm, 5 µm) and samples were analyzed in the positive mode, following protein UV absorbance at 214 and 280 nm. Total protein masses were calculated by deconvolution within the MS Chemstation software (Agilent Technologies). Protein mass spectrometry was additionally carried out with an LCT TOF mass spectrometer (Micromass, see below). Additionally, protein total mass was determined on an LCT time-of-flight mass spectrometer with electrospray ionization (ESI, Micromass). Proteins were rebuffered in 20 mM of ammonium bicarbonate and mixed 1:1 acetonitrile, containing 1% formic acid. Alternatively samples were prepared with a C4 Ziptip (Millipore) and infused directly in 50% aqueous acetonitrile containing 1% formic acid. Samples were injected at 10 µL min$^{-1}$ and calibration was performed in positive ion mode using horse heart myoglobin. 30 scans were averaged and molecular masses obtained by maximum entropy deconvolution with MassLynx version 4.1 (Micromass). Theoretical masses of wild-type proteins were calculated using Protparam (http://us.expasy.org/tools/protparam.html), and theoretical masses for unnatural amino acid containing proteins were adjusted manually.

Protein Labeling Via Tetrazine-Norbornene Cycloaddition

In Vitro Labeling of Purified Proteins with Different Tetrazines

To 40 iL of purified recombinant protein (~10 µM in 20 mM Tris-HCl, 100 mM NaCl, pH 7.4) 4 µL or 8 µL of a 1 mM solution of tetrazine compounds 5, 6, 7, or 8 in MeOH were added (~10 or 20 equivalents). The solution was then incubated at RT and at different time points analyzed by LC-ESI-MS. (FIG. 19)

In Vitro Labeling of Purified Proteins with Tetrazines-Dye Conjugates

Purified recombinant proteins with site-specifically incorporated 2, sfGFP-2, Myo-2, T4L-2 (all ~10 µM in 20 mM Tris-HCl, 100 mM NaCl, pH 7.4), were incubated with 10 equivalents of the tetrazine-dye conjugate 9 (2 mM in dmso). The solution was incubated at RT and aliquots were taken after 12 h and analyzed by SDS PAGE and—after desalting with a C4-ZIPTIP—by ESI-MS. The SDS PAGE gels were either stained with coomassie or scanned with a Typhoon imager to visualize in gel fluorescence.

In Vitro Labeling of Purified Proteins with Tetrazines-Dye Conjugates as a Function of Time 2 nmol of purified Myo-2 (10 µM in 20 mM Tris-HCl, 100 mM NaCl, pH 7.4) was incubated with 20 nmol of tetrazine-dye conjugate 12 (10 µl of a 2 mM solution in dmso). At different time points (0, 30 s, 1 min, 2 min, 3 min, 5 min, 10 min, 30 min, 1 h, 2 h) 8 µL aliquots were taken from the solution and quenched with a 200-fold excess of 5-norbornene-2-ol and plunged into liquid nitrogen. Samples were mixed with NuPAGE LDS sample buffer supplemented with 5% β-mercaptoethanol, heated for 10 min to 90° C. and analyzed by 4-12% SDS page. The amounts of labeled proteins were quantified by scanning the fluorescent bands with a Typhoon Trio phosphoimager (GE Life Sciences). Bands were quantified with the ImageQuant™ TL software (GE Life Sciences) using rubber band background subtraction. In gel fluorescence shows that labeling is complete within thirty minutes using 10 equivalents tetrazine-fluorophore 12 (FIG. 3C). In a similar experiment sfGFP-2 was incubated with tetrazine fluorophore 12 or 9 and samples analyzed at different time points (FIG. 22).

Labeling of the Whole E. coli Proteome with Tetrazine-Dye Conjugates

E. coli DH10B cells containing either psfGFP150TAGPylT-His$_6$ and pBKPylS or pMyo4TAGPylT-His$_6$ and pBKPylS were inoculated into LB containing kanamycin (50 µg/mL) and tetracycline (25 µg/mL). The cells were incubated with shaking overnight at 37° C., 250 rpm. 2 mL of overnight culture was used to inoculate into 100 mL of LB supplemented with kanamycin (25 µg/mL) and tetracycline (12 µg/mL) and incubated at 37° C. At OD$_{600}$=0.5, 3 ml culture aliquots were removed and supplemented with different concentrations (1 mM, 2 mM and 5 mM) of 2 and 1 mM of 3. After 30 min of incubation with shaking at 37° C., protein expression was induced by the addition of 30 µL of 20% arabinose. After 3.5 h of expression, cells were collected by centrifugation (16000 g, 5 min) of 1 mL of cell suspension. The cells were resuspended in PBS buffer, spun down again and the supernatant was discarded. This process was repeated twice more. Finally, the washed cell pellet was suspended in 100 µL PBS and incubated with 3 µL of tetrazine-dye conjugate 12 or 13 (2 mM in dmso) at RT overnight. The cells were collected again by centrifugation and washed two times with 1 ml PBS by suspending and centrifugation. Finally, the cells were resuspended in 100 µL of NuPAGE LDS sample buffer supplemented with 5% β-mercaptoethanol, heated at 90° C. for 10 min and centrifuged at 16000 g for 10 min. The crude cell lysate was analyzed by 4-12% SDS-PAGE to assess protein levels. Gels were either Coomassie stained or scanned with a Typhoon imager to make fluorescent bands visible. Western blots were performed with antibodies against the hexahistidine tag (Cell Signaling Technology, His tag 27E8 mouse mAb #2366).

Determination of Kinetic Rate Constants (Small Molecules)

Rate constants k for different tetrazines were measured under pseudo first order conditions with a 10- to 100-fold excess of 5-norbornene-2-ol in methanol/water mixtures by following the exponential decay in UV absorbance of the tetrazine at 320 or 300 nm over time (FIGS. 15A-C and FIG. 16A).

Stock solutions were prepared for each tetrazine (0.1 mM in 9/1 water/methanol) and for 5-norbornene-2-ol (1 to 10 mM in either methanol or water). Mixing equal volumes of the prepared stock solutions resulted in a final concentration of 0.05 mM tetrazine and of 0.5 to 5 mM 5-norbornene-2-ol, corresponding to 10 to 100 equivalents. Spectra were recorded using the following instrumental parameters: wavelength, 320 nm for 6 and 8; 300 nm for 5 and 3,6-dipyridyl-1,2,4,5-tetrazine, 280 nm for 7; spectral band width (SBW), 1.0 nm; increment of data point collection, 0.5 s or 2.0 s. All data were recorded at 21° C. Data were fit to a single-exponential equation. Each measurement was carried out three times and the mean of the observed rates k' was plotted against the concentration of 5-norbornene-2-ol to obtain the rate constant k from the slope of the plot. All data processing was performed using Kaleidagraph software (Synergy Software, Reading, UK).

Cloning for Mammalian Cells

An amber codon was introduced at position 128 of the EGFR-EGFP fusion protein with the following primers:

```
forward:
ACCAGggtctcGATGCAtagAAAACCGGACTGAAGGAGCTGCCCATG, reverse:
TTGCAggtctcTGCATCATAGTTAGATAAGACTGCTAAGGCATAG.
```

After PCR the product was digested with BsaI and then ligated to circularize. The mutagenesis was verified by sequencing through the EGFR. The initial mutagenesis was carried out on an EGFR-EGFP fusion in the pEGFPN1 vector. The EGFR was then digested out of the pEGFPN1 vector using the enzymes NheI and MfeI (NEB). Similarly pMmPylRS-mCherry-TAG-EGFP-HA[46] was digested with the same enzymes to remove the mCherry-TAG-EGFP-HA reporter. The EGFR-EGFP was ligated into the pMmPylRS-mCherry-TAG-EGFP-HA vector in place of the mCherry-EGFP using T4 DNA ligase (NEB) to create pMmPylRS-EGFR(128TAG)-GFP-HA.

Incorporation of 2 in Mammalian Cells

HEK293 cells were seeded onto a corning 96 well plate and grown to approximately 90% confluence in 10% FBS DMEM with Penicillin/Streptomycin. Cells were transfected with 2 plasmids, pMmPylRS-mCherry-TAG-EGFP-HA, and p4CMVE-U6-PylT which contains 4 copies of the wild-type Pyrrollysyl tRNA. Transfection was carried out using the lipofectamine 2000 transfection reagent from Invitrogen according to the manufacturer's protocol. The growth media in which the cells were transfected was 10% FBS DMEM, and contained 1 mM 2, 1 mM 3 or no additional amino acid as indicated. Cells were imaged on a Zeiss 710 laser-scanning microscope to assay eGFP and mCherry expression after 16-24 hours. Cells were then lysed using 1× Repoter Lysis Buffer (Promega) supplemented with CompleteMini protease inhibitor cocktail (Roche). After lysis the cell debris was pelletted and the supernatant containing oluble proteins removed and added to 4× NuPage LDS sample buffer (Invitrogen). Samples were loaded and run out by SDS-PAGE. Western blotting was carried out to detect full-length reporter protein using rabbit anti-HA (Sigma) antibody, detected with an anti-rabbit HRP conjugate (Cell signalling). As a transfection control Western blotting was also carried out to detect the synthetase using a mouse anti-FLAG antibody (AbFrontier) detected by an HRP-conjugated anti-mouse secondary (Cell Signaling).

MS/MS Analysis Cells were grown on 100 mm tissue culture dishes to ~90% confluence. Cells were transfected with pMmPylRS-mCherry-TAG-EGFP-HA and p4CMVE-U6-PylT using lipofectamine 2000 (Invitrogen). After 16-24 hours in the presence of 1 mM 2 cells were lysed in RIPA buffer and mCherry-eGFP fusion protein was purified using the GFP_Trap_A system (Chromotek). MS/MS analysis was either performed by NextGen Sciences or by an in house facility. For the former, the eluate was added to 4× NuPage LDS Sample buffer and run out on an SDS-PAGE gel. The band corresponding to the full length mCherry-eGFP fusion was then excised. The gel plugs were digested overnight in trypsin. The digests were then analyzed by LC/MS/MS with a 30 minute gradient on an LTQ Orbitrap XL mass spectrometer. Product-ion data were searched against a database of 4 protein sequences, with the lysine modification incorporated among the typically used variable modifications. The Mascot search engine was utilised with the Scaffold program used for collation and analysis of the data.

For the in house analysis, the protein solution was reduced and alkylated using standard methods prior to overnight digest with Promega procine Trypsin. The generated peptides were separated on a Dionex Ultimate 3000 HPLC system with a 15 cm, 75 Um, C18 acclaim pep-map column and analysed on a Thermo Scientific LTQ XL Orbitrap mass spectrometer. Protein identification was carried out using an in-house Mascot database.

Labeling in Mammalian Cells

Cells were seeded and grown on 35 mm □-dishes (Ibidi) coated with poly-L-lysine (Sigma). At ~90% confluence cells were transfected using lipofectamine 2000 (Invitrogen) with 2 plasmids, p4CMVE-U6-PylT and pMmPylRS-EGFR (128TAG)-GFP-HA. The transfection was carried out in DMEM with 0.1% FBS and containing 1 mM of either 2, 3 or 4 as indicated. After transfection cells were grown for 16 hours and then incubated in amino acid free DMEM with 0.1% FBS for 2-5 hours. The hEGFR-eGFP fusion was then labeled with 200 nm of tetrazine-dye conjugate 9 (tet1-TAMRA-X) for 2-16 hours as indicated, washed for 10 mins in DMEM with 0.1% FBS and imaged on Zeiss LSM 780 or Zeiss LSM 710 laser scanning microscope with a Plan Apochromat 63× oil immersion objective and using a 1× or 2× scan zoom, averaging 16. EGFP was excited using a 488 nm Argon laser and detected between 493 nm and 554 nm. TMR was excited using DPSS 561 nm laser and detected at 566-685 nm. Cells transfected in the presence of amino acid 4, were grown for 16 to 24 hours after transfection. According to the suppliers protocols, cells were washed in DPBS with 1% FBS, incubated with DiBO-TAMRA dye (Invitrogen) in DPBS with 1% FBS for 16 hours, washed 4 times in DPBS 1% FBS and imaged in DPBS 1% FBS.

REFERENCES

1 Chalfie, M., Tu, Y., Euskirchen, G., Ward, W. W. & Prasher, D. C. Green fluorescent protein as a marker for gene expression. *Science* 263, 802-805 (1994).
2 Heim, R., Prasher, D. C. & Tsien, R. Y. Wavelength mutations and posttranslational autoxidation of green fluorescent protein. *Proc Natl Acad Sci USA* 91, 12501-12504 (1994).

3 Giepmans, B. N., Adams, S. R., Ellisman, M. H. & Tsien, R. Y. The fluorescent toolbox for assessing protein location and function. *Science* 312, 217-224, doi:312/5771/217 [pii] 10.1126/science.1124618 (2006).

4 Shaner, N. C., Steinbach, P. A. & Tsien, R. Y. A guide to choosing fluorescent proteins. *Nat Methods* 2, 905-909, doi:nmeth819 [pii] 10.1038/nmeth819 (2005).

5 Los, G. V. et al. HaloTag: a novel protein labeling technology for cell imaging and protein analysis. *ACS Chem Biol* 3, 373-382, doi:10.1021/cb800025k (2008).

6 Keppler, A. et al. A general method for the covalent labeling of fusion proteins with small molecules in vivo. *Nat Biotechnol* 21, 86-89, doi:10.1038/nbt765 nbt765 [pii] (2003).

7 Kosaka, N. et al. In vivo stable tumor-specific painting in various colors using dehalogenase-based protein-tag fluorescent ligands. *Bioconjug Chem* 20, 1367-1374, doi: 10.1021/bc9001344 (2009).

8 Gautier, A. et al. An engineered protein tag for multiprotein labeling in living cells. *Chem Biol* 15, 128-136, doi:S1074-5521(08)00041-0 [$_p$ii] 10.1016/j.chembiol.2008.01.007 (2008).

9 George, N., Pick, H., Vogel, H., Johnsson, N. & Johnsson, K. Specific labeling of cell surface proteins with chemically diverse compounds. *J Am Chem Soc* 126, 8896-8897, doi:10.1021/ja048396s (2004).

10 Zhou, Z., Koglin, A., Wang, Y., McMahon, A. P. & Walsh, C. T. An eight residue fragment of an acyl carrier protein suffices for post-translational introduction of fluorescent pantetheinyl arms in protein modification in vitro and in vivo. *J Am Chem Soc* 130, 9925-9930, doi:10.1021/ja802657n (2008).

11 Yin, J. et al. Genetically encoded short peptide tag for versatile protein labeling by Sfp phosphopantetheinyl transferase. *Proc Natl Acad Sci USA* 102, 15815-15820, doi:0507705102 [pii] 10.1073/pnas.0507705102 (2005).

12 Fernandez-Suarez, M. et al. Redirecting lipoic acid ligase for cell surface protein labeling with small-molecule probes. *Nat Biotechnol* 25, 1483-1487, doi:nbt1355 [pii] 10.1038/nbt1355 (2007).

13 Uttamapinant, C. et al. A fluorophore ligase for site-specific protein labeling inside living cells. *Proc Natl Acad Sci USA* 107, 10914-10919, doi:0914067107 [pii] 10.1073/pnas.0914067107 (2010).

14 Popp, M. W., Antos, J. M., Grotenbreg, G. M., Spooner, E. & Ploegh, H. L. Sortagging: a versatile method for protein labeling. *Nat Chem Biol* 3, 707-708, doi:nchembio.2007.31 [pii] 10.1038/nchembio.2007.31 (2007).

15 Antos, J. M. et al. Site-specific N- and C-terminal labeling of a single polypeptide using sortases of different specificity. *J Am Chem Soc* 131, 10800-10801, doi: 10.1021/ja902681k (2009).

16 Griffin, B. A., Adams, S. R. & Tsien, R. Y. Specific covalent labeling of recombinant protein molecules inside live cells. *Science* 281, 269-272 (1998).

17 Halo, T. L., Appelbaum, J., Hobert, E. M., Balkin, D. M. & Schepartz, A. Selective recognition of protein tetraserine motifs with a cell-permeable, pro-fluorescent bis-boronic acid. *J Am Chem Soc* 131, 438-439, doi:10.1021/ja807872s 10.1021/ja807872s [pii] (2009).

18 Hinner, M. J., Johnsson, K. How to obtain labeled proteins and what to do with them. *Curr Opin Biotechnol* 21, 766-776 (2010).

19 Chin, J. W. et al. Addition of p-azido-L-phenylalanine to the genetic code of *Escherichia coli*. *J Am Chem Soc* 124, 9026-9027, doi:ja027007w [pii] (2002).

20 Zhang, Z., Wang, L., Brock, A. & Schultz, P. G. The selective incorporation of alkenes into proteins in *Escherichia coli*. *Angew Chem Int Ed Engl* 41, 2840-2842, doi:10.1002/1521-3773(20020802)41:15<2840::AID-ANIE2840>3.0.CO;2-# (2002).

21 Chin, J. W. et al. An expanded eukaryotic genetic code. *Science* 301, 964-967, doi:10.1126/science.1084772 301/5635/964 [pii] (2003).

22 Deiters, A. et al. Adding amino acids with novel reactivity to the genetic code of *Saccharomyces cerevisiae*. *J Am Chem Soc* 125, 11782-11783, doi:10.1021/ja0370037 (2003).

23 Deiters, A., Cropp, T. A., Summerer, D., Mukherji, M. & Schultz, P. G. Site-specific PEGylation of proteins containing unnatural amino acids. *Bioorg Med Chem Lett* 14, 5743-5745, doi:S0960-894X(04)01181-3 [pii] 10.1016/j.bmcl.2004.09.059 (2004).

24 Mehl, R. A. et al. Generation of a bacterium with a 21 amino acid genetic code. *J Am Chem Soc* 125, 935-939, doi:10.1021/ja0284153 (2003).

25 Wang, L., Zhang, Z., Brock, A. & Schultz, P. G. Addition of the keto functional group to the genetic code of *Escherichia coli*. *Proc Natl Acad Sci USA* 100, 56-61, doi:10.1073/pnas.0234824100 0234824100 [pii] (2003).

26 Carrico, Z. M., Romanini, D. W., Mehl, R. A. & Francis, M. B. Oxidative coupling of peptides to a virus capsid containing unnatural amino acids. *Chem Commun (Comb)*, 1205-1207, doi:10.1039/b717826c (2008).

27 Fekner, T., Li, X., Lee, M. M. & Chan, M. K. A pyrrolysine analogue for protein click chemistry. *Angew Chem Int Ed Engl* 48, 1633-1635, doi:10.1002/anie.200805420 (2009).

28 Nguyen, D. P. et al. Genetic encoding and labeling of aliphatic azides and alkynes in recombinant proteins via a pyrrolysyl-tRNA Synthetase/tRNA(CUA) pair and click chemistry. *J Am Chem Soc* 131, 8720-8721, doi:10.1021/ja900553w (2009).

29 Wang, Y., Song, W., Hu, W. J. & Lin, Q. Fast alkene functionalization in vivo by Photoclick chemistry: HOMO lifting of nitrile imine dipoles. *Angew Chem Int Ed Engl* 48, 5330-5333, doi:10.1002/anie.200901220 (2009).

30 Agard, N. J., Baskin, J. M., Prescher, J. A., Lo, A. & Bertozzi, C. R. A comparative study of bioorthogonal reactions with azides. *ACS Chem Biol* 1, 644-648 (2006).

31 Wang, J. et al. A biosynthetic route to photoclick chemistry on proteins. *J Am Chem Soc* 132, 14812-14818, doi:10.1021/ja104350y (2010).

32 Nguyen, D. P., Elliott, T., Holt, M., Muir, T. W. & Chin, J. W. Genetically Encoded 1,2-Aminothiols Facilitate Rapid and Site-Specific Protein Labeling via a Bioorthogonal Cyanobenzothiazole Condensation. *J Am Chem Soc* 133, 11418-11421, doi:10.1021/ja203111c (2011).

33 Laughlin, S. T. & Bertozzi, C. R. Imaging the glycome. *Proc Natl Acad Sci USA* 106, 12-17, doi:0811481106 [pii] 10.1073/pnas.0811481106 (2009).

34 Prescher, J. A. & Bertozzi, C. R. Chemical technologies for probing glycans. *Cell* 126, 851-854, doi:S0092-8674(06)01084-1 [pii] 10.1016/j.cell.2006.08.017 (2006).

35 Johnson, J. A., Lu, Y. Y., Van Deventer, J. A., Tirrell, D. A. Residue-specific incorporation of non-canonical amino acids into proteins: recent developments and applications. *Curr Opin Biotechnol* 14, 774-780 (2010).

36 Blackman, M. L., Royzen, M. & Fox, J. M. Tetrazine ligation: fast bioconjugation based on inverse-electron-demand Diels-Alder reactivity. *J Am Chem Soc* 130, 13518-13519, doi:10.1021/ja8053805 (2008).

37 Devaraj, N. K., Weissleder, R. & Hilderbrand, S. A. Tetrazine-based cycloadditions: application to pretargeted live cell imaging. *Bioconjug Chem* 19, 2297-2299, doi: 10.1021/bc8004446 10.1021/bc8004446 [pii] (2008).

38 Devaraj, N. K. & Weissleder, R. Biomedical Applications of Tetrazine Cycloadditions. *Acc Chem Res*, doi:10.1021/ar200037t (2011).

39 Mukai, T. et al. Adding l-lysine derivatives to the genetic code of mammalian cells with engineered pyrrolysyl-tRNA synthetases. *Biochem Biophys Res Commun* 371, 818-822, doi:S0006-291X(08)00860-7 [pii] 10.1016/j.bbrc.2008.04.164 (2008).

40 Neumann, H., Peak-Chew, S. Y. & Chin, J. W. Genetically encoding N(epsilon)-acetyllysine in recombinant proteins. *Nat Chem Biol* 4, 232-234, doi:nchembio.73 [pii] 10.1038/nchembio.73 (2008).

41 Hancock, S. M., Uprety, R., Deiters, A. & Chin, J. W. Expanding the genetic code of yeast for incorporation of diverse unnatural amino acids via a pyrrolysyl-tRNA synthetase/tRNA pair. *J Am Chem Soc* 132, 14819-14824, doi:10.1021/ja104609m (2010).

42 Greiss, S. & Chin, J. W. Expanding the Genetic Code of an Animal. *J Am Chem Soc,* doi:10.1021/ja2054034 (2011).

43 Polycarpo, C. R. et al. Pyrrolysine analogues as substrates for pyrrolysyl-tRNA synthetase. *FEBS Lett* 580, 6695-6700, doi:S0014-5793(06)01347-0 [pii] 10.1016/j.febslet.2006.11.028 (2006).

44 Li, X., Fekner, T., Ottesen, J. J. & Chan, M. K. A pyrrolysine analogue for site-specific protein ubiquitination. *Angew Chem Int Ed Engl* 48, 9184-9187, doi: 10.1002/anie.200904472 (2009).

45 Nguyen, D. P., Garcia Alai, M. M., Kapadnis, P. B., Neumann, H. & Chin, J. W. Genetically encoding N(epsilon)-methyl-L-lysine in recombinant histones. *J Am Chem Soc* 131, 14194-14195, doi:10.1021/ja906603s (2009).

46 Gautier, A. et al. Genetically encoded photocontrol of protein localization in mammalian cells. *J Am Chem Soc* 132, 4086-4088, doi:10.1021/ja910688s (2010).

47 Direct oxidation of dihydrotetrazines 5a and 6a to the corresponding tetrazines lead to compounds, whose amino groups were not susceptible to any further transformation, probably because the amino group looses its nucleophilicity through π-conjugation with the aromatic rings.

48 Wijinen, J. W., Zavarise, S., Engberts, J. B. F. N; Cahrton, M I. J. Substituent Effects on an Inverse Electron Demand Hetero DielsiAlder Reaction in Aqueous Solution and Organic Solvents: Cycloaddition of Substituted Styrenes to Di(2-pyridyl)-1,2,4,5-tetrazine. *J Org Chem* 61, 2001 (1996).

49 Devaraj, N. K., Hilderbrand, S., Upadhyay, R., Mazitschek, R. & Weissleder, R. Bioorthogonal Turn-On Probes for Imaging Small Molecules inside Living Cells. *Angew Chem Int Ed Engl* 49, 2869-2872, doi:10.1002/anie.200906120 (2010).

50 Since we add label to the cell population, and subsequently lyse the cells, we cannot rule out that labeling may take place in the lysate.

Example 3

Chemical Syntheses:

General Methods $^1$H and $^{13}$C NMR spectra were recorded on a Bruker 400 MHz instrument. Chemical shifts (δ) are reported relative to TMS and referenced to the residual proton signal in the deuterated solvents: CDCl$_3$ (7.26 ppm), d$_6$-DMSO (2.49 ppm) for $^1$H-NMR spectra, CDCl$_3$ (77.0 ppm) of d$_6$-DMSO (39.5 ppm) for $^{13}$C-NMR spectra. J values are given in Hertz, and the splitting patterns are designed as follows: s, singlet; s, br, broad singlet; d, doublet; t, triplet; m, multiplet. Analytical thin-layer chromatography (TLC) was carried out on silica 60F-254 plates. The spots were visualized by UV light (254 nm) and/or by potassium permanganate staining. Flash column chromatography was carried out on silica gel 60 (230-400 mesh or 70-230 mesh). Using an Agilent 1200 LC-MS system, ESI-MS was carried out with a 6130 Quadrupole spectrometer. The solvent system consisted of 0.2% formic acid in H$_2$O as buffer A, and 0.2% formic acid in acetonitrile (MeCN) as buffer B. Small molecule LC-MS was carried out using a Phenomenex Jupiter C18 column (150×2 mm, 5 μm). Variable wavelengths were used and MS acquisitions were carried out in positive and negative ion modes.

Synthesis of Nobornene Lysine 2

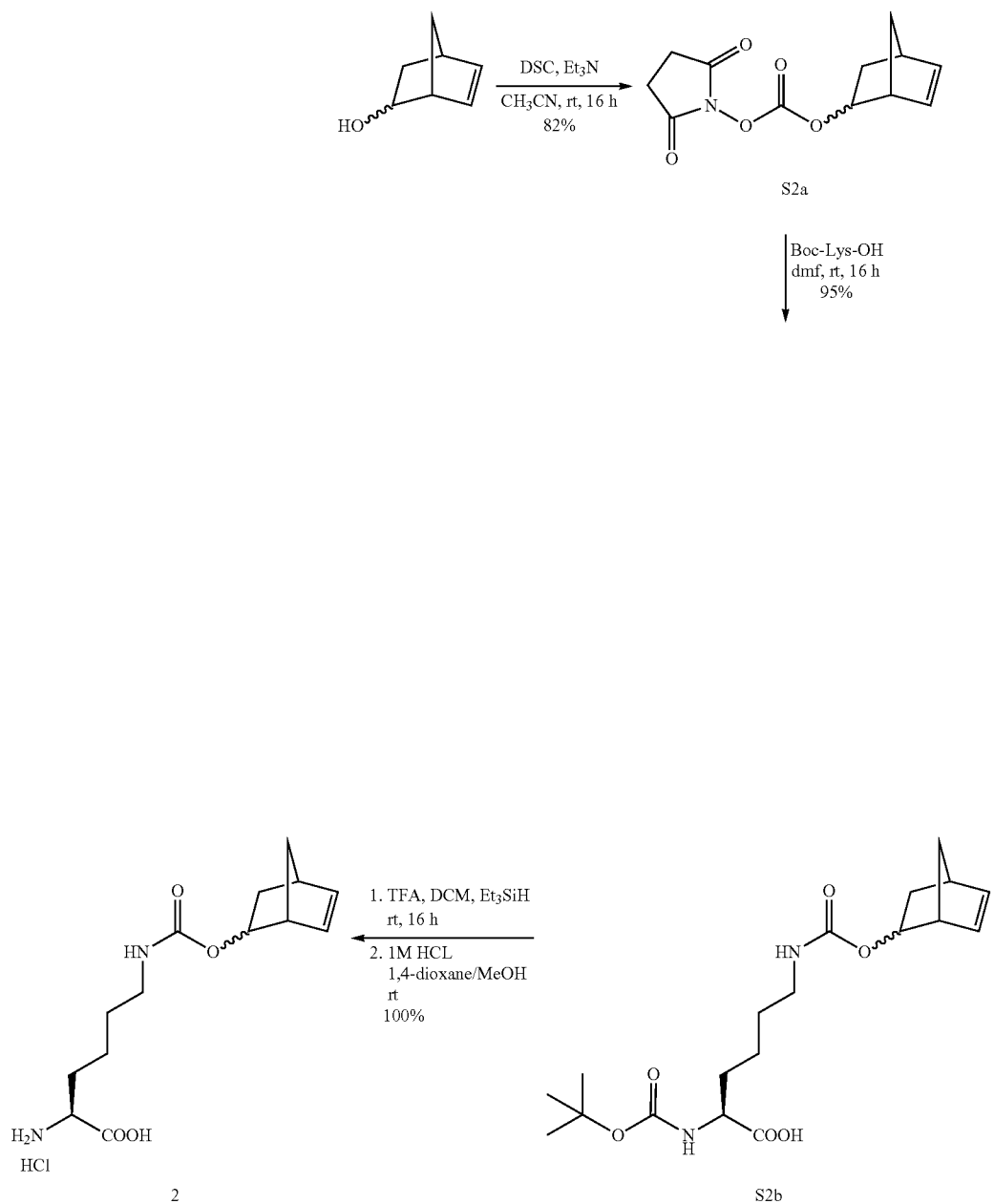

Supplementary Scheme 1. Synthetic route for Nε-5-norbornene-2-yloxy-carbonyl-L-lysine (2)

Disuccinimide carbonate (6.3 g, 0.024 mol) was added to a solution of (1R,4R)-5-norbornene-2-ol (endo/exo mixture, 1.5 g, 0.014 mol) and triethylamine (5.7 mL, 0.041 mol) in dry acetonitrile (50 mL) at room temperature. The resulting mixture was stirred overnight and then concentrated under vacuum. The product was purified by column chromatography on SiO2 (1-5% diethyl ether in dichloromethane) to deliver S2a as a white solid in 82%, 7:3 endo/exo (2.8 g, 0.011 mol). Rf (Et$_2$O/DCM, 1/99): 0.4; $^1$H-NMR (300 MHz, CDCl$_3$): δ 6.32 and 6.23 (m$_{endo}$, dd$_{exo}$, J=2.7 Hz, 1H), 5.94 and 5.89 (m$_{endo}$, t$_{exo}$, J=3.6 Hz, 1H), 5.28 and 4.66 (m$_{endo}$, d$_{exo}$, J=5.7 Hz, 1H), 3.19 and 3.00 (s$_{endo}$, s$_{exo}$, 1H), 2.84 (s, 1H), 2.80 (s, 4H), 2.21-2.13 and 1.81-1.57 (m$_{endo}$, m$_{exo}$, 1H), 1.52-1.49 (m, 1H), 1.32 (d, J=9.0 Hz, 1H), 1.14-1.08 (dt, J$_1$=12.9 Hz, J$_2$=2.4 Hz, 1H) ppm; $^{13}$C-NMR (300 MHz, CDCl$_3$): δ 169.02, 168.95, 151.25, 142.10, 139.16, 131.69, 130.90, 83.20, 82.76, 47.58, 47.23, 46.23, 45.72, 42.16, 40.52, 34.43, 25.44 ppm; ESI-MS (m/z): [M+Na]$^+$ calcd for C$_{12}$H$_{13}$NO$_5$ 274.0686, found 274.0683.

Boc-Lys-OH (3.2 g, 0.013 mol) was added to a stirred solution of S2a (2.5 g, 0.010 mol) in dry dimethylformamide (35 mL). The reaction was allowed to proceed overnight at room temperature. The mixture was diluted in water (150 mL) and extracted with ethyl acetate (150 mL×3). The combined organic layers were washed with water (100 mL×3) and brine (75 mL). The resulting organic layer was dried over $Na_2SO_4$, filtered and concentrated under vacuum to dryness. Compound S2b was obtained in 95% yield (3.6 g, 9.40 mmol) as an off-white foam. Rf ($Et_2O$/DCM, 5/95): 0.1; $^1$H-NMR (300 MHz, $CDCl_3$): δ 9.11 (s, br, 1H), 8.03 (s, br, 1H), 6.30-6.21 (m, 1H), 5.95-5.93 (m, 1H), 5.30 and 4.59 (d, br$_{endo}$, J=7.2 Hz; d, br$_{exo}$, J=6.9 Hz, 1H), 5.24 (s, br, 1H), 4.86 (m, br, 1H), 4.77 (m, br, 1H), 4.28 (s, br, 1H), 4.09 (m, br, 1H), 3.12 (m, br, 2H), 2.80 (m, br, 1H), 2.09 (m, 1H), 1.81-1.28 (m, br, 15H), 0.90 (d, br, J=12.9 Hz, 1H) ppm; $^{13}$C-NMR (300 MHz, $CDCl_3$): δ 175.95, 156.76, 155.58, 140.74, 138.19, 132.49, 131.43, 79.76, 75.35, 75.14, 52.90, 47.39, 47.20, 45.91, 45.74, 41.95, 40.30, 40.14, 34.28, 31.73, 29.14, 28.09, 22.10, 21.75 ppm; ESI-MS (m/z): [M+Na]$^+$ calcd for $C_{19}H_{30}N_2O_6$ 405.1996, found 405.1983.

To a solution of S2b (3.3 g, 8.60 mmol) and Et3SiH (2.7 ml, 0.017 mol) in dry dichloromethane (120 mL), trifluoroacetic acid (6.4 mL, 0.086 mol) was added dropwise, and the reaction mixture was allowed to stir at room temperature overnight. The solvents were evaporated under reduced pressure. The residue was re-dissolved in a 1M HCl solution (5 mL 4N HCl in 1,4-dioxane, 15 mL dry methanol), allowed to stir for 10 min and then concentrated. The latter process was repeated two more times to ensure complete HCl salt exchange. The concentrated residue was re-dissolved in a minimal amount of methanol and was precipitated into ice-cold diethyl ether, filtered and dried under vacuum, affording the amino acid 2 as a white solid in quantitative yield (2.7 g, 8.50 mmol). $^1$H-NMR (300 MHz, $CD_3OD$): δ 6.30-6.25 (m, 1H), 6.00-5.93 (m, 1H), 5.15 and 4.52 ($m_{endo}$, $m_{exo}$, 1H), 4.85 (m, 1H), 3.55 (t, J=5.4 Hz, 1H), 3.07 (q, J=6.7 Hz, 2H), 2.81 (d, J=6.6 Hz, 1H), 2.13-2.05 (m, 1H), 1.93-1.74 (m, 2H), 1.68-1.63 (m, 1H), 1.53-1.28 (m, 5H), 0.93-0.87 (dt, $J_1$=12.3 Hz, $J_2$=2.7 Hz, 1H) ppm; $^{13}$C-NMR (300 MHz, $CD_3OD$): δ 174.82, 159.52, 142.37, 139.36, 133.84, 132.80, 76.73, 76.73, 56.16, 47.43, 47.13, 43.63, 41.93, 41.42, 35.67, 32.80, 32.07, 30.74, 28.90, 24.22, 23.63 ppm; ESI-MS (m/z): [M+Na]$^+$ calcd for $C_{14}H_{22}N_2O_4$ 305.1472; found: 305.1475.

Synthesis of the Tetrazine Probes

Supplementary Scheme 2.

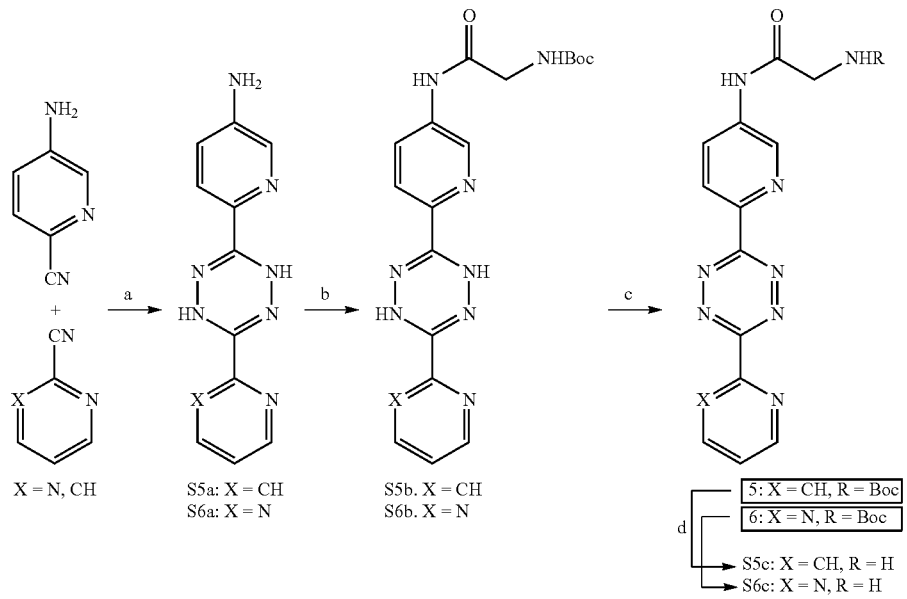

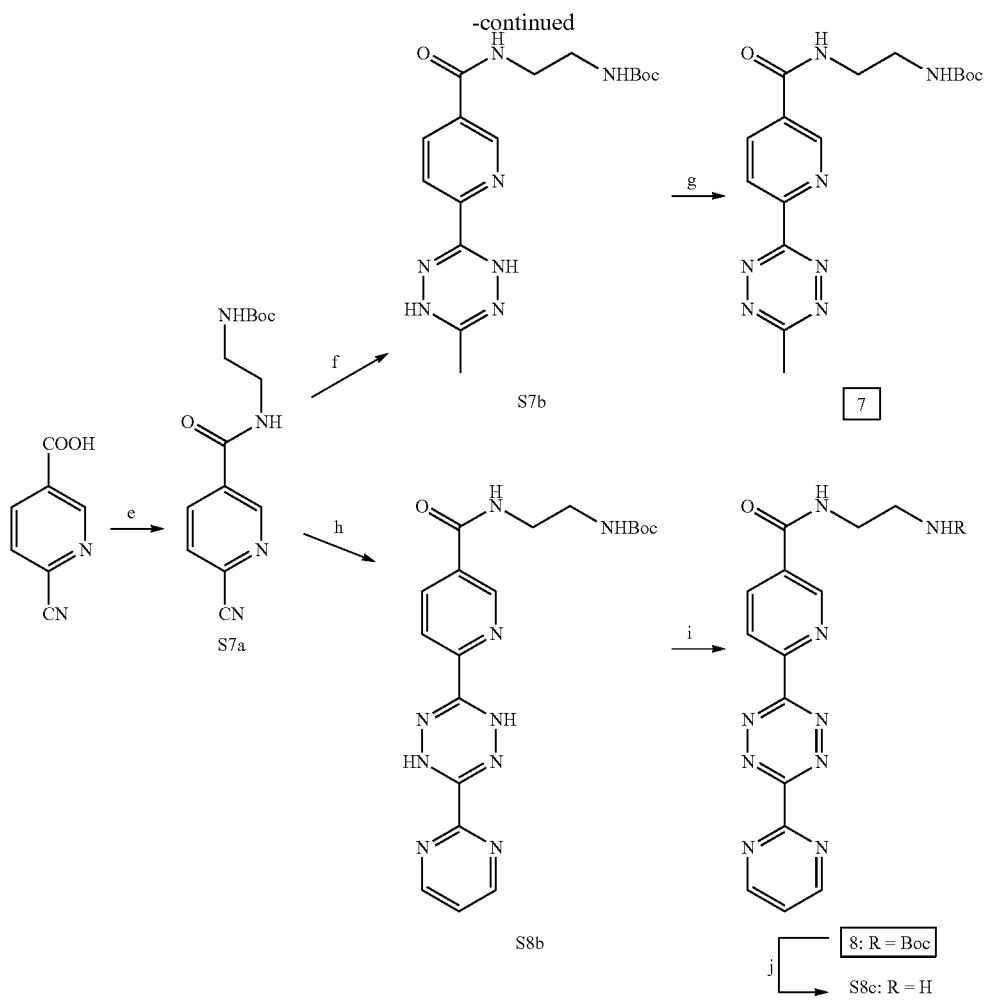

Overview of synthetic route to various tetrazines used in this study. a) 4 eq hydrazine hydrate (64%), 12 h, 90° C., 33%; b) 4 eq N-tert-butoxycaronylglycine, 5 eq N-methylpyrrolidone, 3.3 eq isobutylchloroformate in THF, 0° C.-rt, 3h, 80%; c) 1.5 eq sodiumnitrate in acetic acid, 10 min, rt, 65%; d) 4 N HCl in dioxane/DCM, 30 min, rt, 100%; e) 0.5 eq 4-dimethylaminiopyridine, 1.5 eq N-tert-butyloxycarbonylethylenediamine, 1.5 eq 1-ethyl-3-(3-dimethylaminopropyl)carbodiimide, in DCM, 0° C.-rt, 5 h, 90%; f) 5 eq hydrazine hydrate (64%) in acetonitrile, 90° C., 12 h, 45%; g) 1.5 eq sodiumnitrate in acetic acid, 10 min, rt, 55%; h) 1 eq pyrimidine-2-carbonitrile, 5 eq hydrazine hydrate (64%) in ethanol, 90° C., 12 h, 40%; i) 1.5 eq sodiumnitrate in acetic acid, 10 min, rt, 50%; j) 4N HCl in dioxane/DCM, 30 min, rt, 100%. THF, tetrahydrofurane; DCM, dichloromethane; Boc, tert-butyloxycarbonyl.

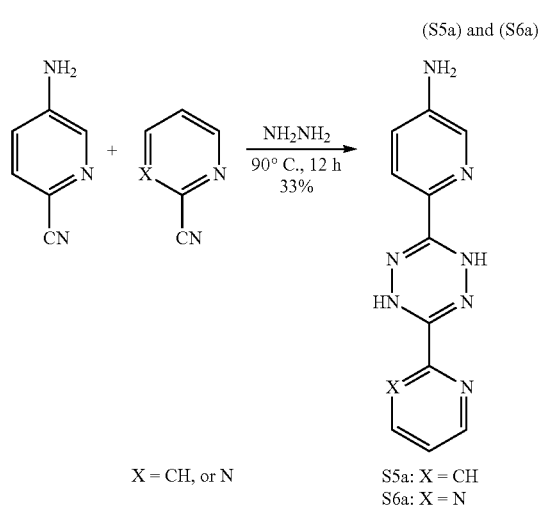

Equimolar amounts of 5-amino-2-cyanopyridine (1.14 g, 9.6 mmol) and 2-cyanopyridine (1.00 g, 9.6 mmol) were mixed with 64% aqueous hydrazine (1.85 ml, 38.4 mmol) and heated for 12 h to 90° C. behind a blast shield. The mixture was allowed to cool to room temperat (rt), the orange precipitate was isolated by filtration, washed with cold water and dried under vacuum. The crude solid was dissolved in methanol, concentrated onto silica gel and S5a was purified by chromatography on SiO2 (0% to 3% methanol in dichloromethane) as an orange solid (802 mg, 33%). $R_f$ (CH$_2$C$_{12}$/MeOH, 92/8): 0.50; $^1$H-NMR (400 MHz, d$_6$-DMSO): δ 8.77 (s, 1H), 8.72 (s, 1H), 8.66-8.68 (m, 1H), 7.93-8.03 (m, 3H), 7.71 (d, J=8.4 Hz, 1H), 7.54-7.57 (m, 1H), 7.04-7.07 (dd, J$_1$=8.8 Hz, J$_2$=2.8 Hz. 1H), 5.93 (s, 2H) ppm; $^{13}$C-NMR (400 MHz, d$_6$-DMSO): δ 148.52 (CH), 147.48 (C), 146.65 (C), 146.62 (C), 146.59 (C), 137.29 (CH), 134.15 (C), 134.06 (CH), 125.12 (CH), 121.81 (CH), 120.76 (CH), 120.27 (CH) ppm; ESI-MS (m/z): [M+H]$^+$ calcd for C$_{12}$H$_{11}$N$_7$ 253.11, found 253.3. In a similar experiment 5-amino-2-cyanopyridine (1.51 g, 9.52 mmol) and pyrimidine-2-carbonitrile (1.00 g, 9.52 mmol) were mixed with 64% hydrazine hydrate (2.3 ml, 47.6 mmol) for 12 h at 90° C. and compound S6a was isolated by column chromatography on SiO$_2$ (750 mg, 31%). R$_f$ (CH$_2$C$_{12}$/MeOH, 92/8): 0.50; $^1$H-NMR (400 MHz, d$_6$-DMSO): δ 8.95 (d, J=4.8 Hz, 2H), 8.88 (s, 1H), 8.71 (s, 1H), 7.99 (d, J=2.4 Hz, 1H), 7.70 (d, J=8.4 Hz, 1H), 7.64 (t, J=4.8, 1H), 7.04-7.07 (dd, J$_1$=8.4, J$_2$=2.4, 1H), 5.94 (s, 2H) ppm; $^{13}$C-NMR (400 MHz, d$_6$-DMSO): δ 157.62 (CH), 156.12 (C), 146.66 (C), 146.11 (C), 146.00 (C), 134.09 (CH), 133.96 (C), 121.96 (CH), 121.92 (CH), 120.28 (CH) ppm; ESI-MS (m/z): [M+H]$^+$ calcd for C$_{11}$H$_{10}$N$_8$ 254.10, found 254.3.

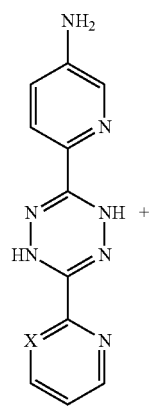

(S5b) and (S6b)

S5a: X = CH
S6a: X = N

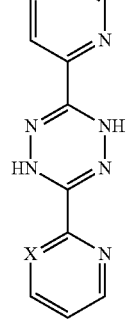 isobutylchololoroformate NMP in THF, 0° C. to rt, 2 h 80%

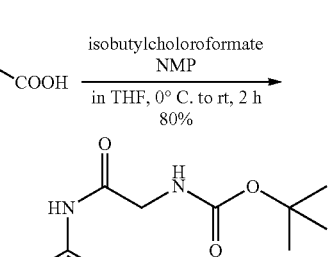

S5b: X = CH
S6b: X = N

To a stirred solution of N-(tert-butoxycarbonyl)glycine (1.66 g, 9.48 mmol) in dry THF N-methylpyrrolidone (1.3 ml, 11.85 mmol) was added. The reaction mixture was chilled to 0° C. before isobutylchloroformate (1.0 ml, 7.82 mmol) was added dropwise. A white precipitate was formed instantaneously and the mixture was stirred at 0° C. before the portion-wise addition of 3-(5-aminopyridin-2-yl)-6-(pyridin-2-yl)-1,4-dihydro-s-tetrazine S5a (600 mg, 2.37 mmol) in dry THF (15 ml). The reaction was allowed to warm to rt with stirring and after 3 h the reaction was adjudged complete by TLC analysis. The solvent was evaporated and the residue dissolved in dichloromethane. The solution was extracted with 5% citric acid, water and saturated sodium bicarbonate solution. The organic layer was dried over Na2SO4 and the product S5b (778 mg, 80%) was isolated by column chromatography on SiO$_2$ (0% to 4% methanol in dichloromethane). R$_f$ (CH$_2$C$_{12}$/MeOH, 95/5): 0.70; $^1$H-NMR (400 MHz, d$_6$-DMSO): δ 10.41 (s 1H), 8.94 (s, 1H), 8.88 (s, 1H), 8.24-8.29 (d, J=2.0 Hz, 1H), 8.63-8.65 (m, 1H), 8.15-8.17, dd, J$_1$=8.8, J$_2$=2.4 Hz, 1H), 7.92-7.99 (m, 3H), 7.52-7.55 (m, 1H), 7.13 (t, J=6.0 Hz, 1H), 3.78 (d, J=6.0 Hz, 2H), 1.39 (s, 9H) ppm; $^{13}$C-NMR (400 MHz, d6-DMSO): δ 169.12 (C), 155.80 (C), 148.56 (CH), 147.27 (C), 146.30 (C), 146.02 (C), 141.57 (C), 138.91 (CH), 137.35 (CH), 136.95 (C), 126.75 (CH), 125,265 (CH), 121.39 (CH), 120.92 (CH), 78.13 (C), 43.81 (CH$_2$), 28.16 (3×CH$_3$) ppm; ESI-MS (m/z): [M+H]$^+$ calcd for C$_{19}$H$_{22}$N$_8$O$_3$ 410.18, found 410.2.

Compound S6b (605 mg, 75%) was synthesized in a similar way by reacting S6a (500 mg, 1.96 mmol) with N-tert-butyloxycarbonylglycine (1.37 g, 7.84 mmol), isobutylchloroformate (883 mg, 840 μl, 6.47 mmol) and N-methylpyrrolidone (991 mg, 1.08 ml, 9.8 mmol) in dry THF. R$_f$ (CH$_2$C$_{12}$/MeOH, 95/5): 0.70; $^1$H-NMR (400 MHz, d$_6$-DMSO): δ 10.42 (s, 1H), 9.05 (s, 1H), 8.93 (d, J=4.8 Hz, 2H), 8.89 (s, 1H), 8.82 (m, 1H), 8.14-8.19 (m, 1H), 7.93-7.96 (m, 1H), 7.62 (t, J=4.8 Hz, 1H), 7.13 (t, J=6.0 Hz, 1H), 3.79 (d, J=6.0 Hz, 2H), 1.41 (s, 9H) ppm; $^{13}$C-NMR (400 MHz, d$_6$-DMSO): δ 169.14 (C), 157.66 (2×CH), 155.98 (C), 155.91 (C), 145.64 (C), 145.55 (C), 141.40 (C), 138.95 (CH), 136.98 (C), 126.77 (CH), 122.08 (CH), 121.49 (CH), 78.14 (C), 43.82 (CH$_2$), 27.34 (3×CH$_3$) ppm; ESI-MS (m/z): [M+H]$^+$ calcd for C$_{18}$H$_{21}$N$_9$O$_3$ 411.18, found 411.3.

(5) and (6)

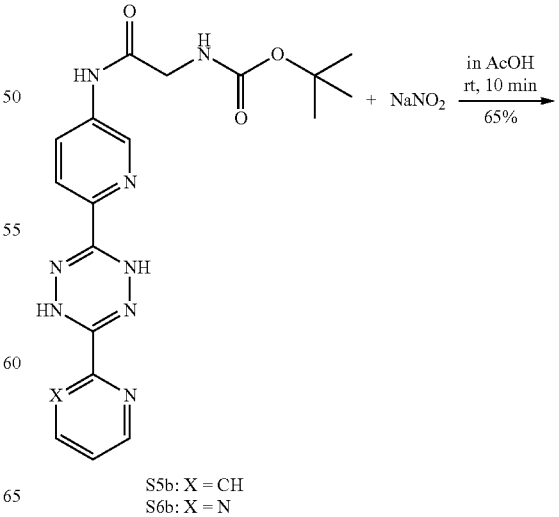

S5b: X = CH
S6b: X = N

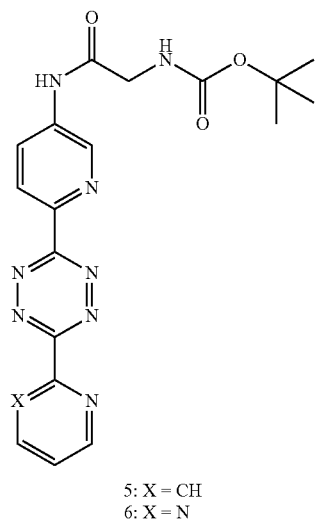

5: X = CH
6: X = N

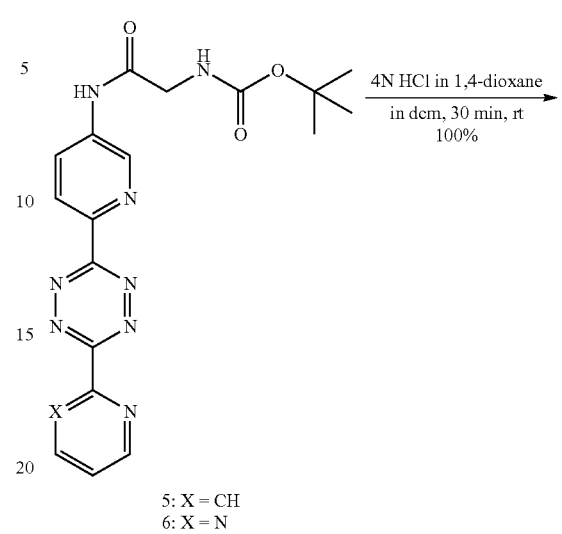

5: X = CH
6: X = N

To a stirred solution of S5b (200 mg, 0.49 mmol) in acetic acid (10 ml) sodium nitrite (50 mg, 0.73 mmol) was added at rt. After 10 min the reaction mixture was diluted with dichloromethane and extracted several times with a half-saturated sodium bicarbonate solution. The organic layer was dried over Na2SO4 and the solvent evaporated. Column chromatography on SiO2 (0% to 8% methanol in dichloromethane) afforded 5 as a pink solid (130 mg, 65%). $R_f$ (CH$_2$C$_{12}$/MeOH, 9/1): 0.50; $^1$H-NMR (400 MHz, d$_6$-DMSO): δ 10.62 (s, 1H), 9.06 (d, J=2.28, 1H), 8.94 (m, 1H), 8.65 (d, J=8.68, 1H), 8.60 (d, J=7.88, 1H), 8.43 (dd, J1=8.68, J2=2.36, 1H), 8.16 (dt, J$_1$=7.76, J$_2$=1.72, 1H), 7.73 (ddd, J$_1$=7.76, J$_2$=1.72, 1H), 7.18 (t, J=6.0 Hz, 1H), 3.85 (d, J=6.0 Hz, 1.42, s 9H) ppm; $^{13}$C-NMR (400 MHz, d$_6$-DMSO): δ 169.5 (C), 163.0 (C), 162.7 (C), 156.0 (C), 150.6 (CH), 150.2 (C), 144.0 (C), 141.3 (CH), 138.2 (C), 137.8 (CH), 126.5 (CH), 126.3 (CH), 124.9 (CH), 124.2 (CH), 78.2 (CH$_2$), 43.9 (C), 28.2 (CH$_3$) ppm; ESI-MS (m/z): [M+H]$^+$ calcd for C$_{19}$H$_{20}$N$_8$O$_3$ 408.17, found 408.2.

Oxidation of S6b (150 mg, 0.36 mmol) with NaNO$_2$ (38 mg, 0.55 mmol) under similar conditions gave 88 mg (60%) of compound 6. $R_f$ (CH$_2$C$_{12}$/MeOH, 9/1): 0.50; $^1$H-NMR (400 MHz, d$_6$-DMSO): δ 10.64 (s, 1H), 9.21 (d, J=4.8 Hz, 2H), 9.07 (d, J=2.4 Hz, 1H), 8.67 (d, J=8.8 Hz, 1H), 8.43-8.46 (dd, J$_1$=8.8 Hz, J$_2$=2.4 Hz, 1H), 7.84 (t, J=4.8, 1H), 7.18 (t, J=6.0, 1H), 3.84 (d, J=6.0 Hz, 2H), 1.42 (s, 9H) ppm; $^{13}$C-NMR (400 MHz, d$_6$-DMSO): δ 169.4 (C), 162.76 (C), 162.68 (C), 159.09 (C), 158.47 (CH), 155.95 (C), 143.78 (C), 141.34 (C), 138.33 (C), 126.22 (CH), 125.30 (CH), 122.95 (CH), 78.18 (C), 43.93 (CH2), 28.18 (3×CH3) ppm; ESI-MS (m/z): [M+H]$^+$ calcd for C$_{18}$H$_{19}$N$_9$O$_3$ 409.16, found 409.4.

(S5c) and (S6c)

4N HCl in 1,4-dioxane
in dcm, 30 min, rt
100%

S5c: X = CH
S6c: X = N

To a stirred solution of compound 5 (100 mg, 0.24 mmol) in dry dichloromethane (4 ml) a 4N HCl solution in dioxane (2 ml) was added and the reaction mixture was allowed to stir for 30 min at rt, after which time complete consumption of the starting material was observed by LC-MS and TLC analysis. The reaction mixture was concentrated to dryness under reduced pressure, to give compound S5c as HCl salt (85 mg, 100%). The crude material was deemed pure enough for subsequent reactions. $^1$H-NMR (400 MHz, d$_6$-DMSO): δ 11.7 (s, 1H), 9.13 (d, J=2.4 Hz, 1H), 8.87-8.89 (m, 1H), 8.61 (d, J=8.8 Hz, 1H), 8.56 (d, J=8.0 Hz, 1H), 8.38-8.41 (dd, J$_1$=8.8 Hz, J$_2$=2.4 Hz, 1H and s, br, 2H), 8.12-8.16 (dt, J$_1$=7.6 Hz, J$_2$=1.8 Hz, 1H), 7.69-7.72 (m, 1H), 3.88 (m, 2H) ppm; $^{13}$C-NMR (400 MHz, d$_6$-DMSO): δ 166.08 (C), 162.81 (C), 162.67 (C), 150.24 (CH), 147.90 (C), 144.40 (C), 141.21 (CH), 138.35 (CH), 137.76 (C), 126.79 (CH), 126.61 (CH), 125.06 (CH), 124.32 (CH), 41.20 (CH$_2$) ppm; ESI-MS (m/z): [M+H]$^+$ calcd for C$_{14}$H$_{12}$N$_8$O 308.11, found 308.3.

Deprotection of compound 6 (150 mg, 0.37 mmol) under similar acidic conditions afforded compound S6c as HCl salt (126 mg, 100%). $^1$H-NMR (400 MHz, d$_6$-DMSO): δ 11.79 (s, 1H), 9.13 (m, 3H), 8.62 (d, J=4.4 Hz, 1H), 8.38-8.41 (m, br, 3H), 7.77 (t, J=4.8 Hz, 1H), 3.88 (m, 2H) ppm; $^{13}$C-NMR (400 MHz, d$_6$-DMSO): δ 166.11 (C), 162.77 (C), 162.58 (C), 159.02 (C), 158.49 (2×CH), 144.19 (C), 141.21 (CH), 137.90 (C), 126.61 (CH), 125.40 (CH), 122.99 (CH), 43.58 (CH2) ppm; ESI-MS (m/z): [M+H]$^+$ calcd for C$_{13}$H$_{11}$N$_9$O 309.11, found 309.5.

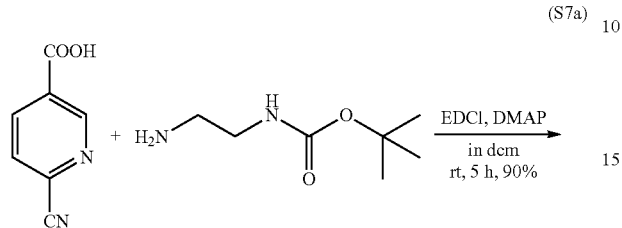
(S7a)

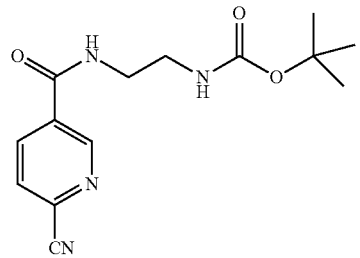
S7a

To a stirred solution of 6-cyanonicotinic acid (500 mg, 3.38 mmol) in dry dichloromethane (30 ml) 4-dimethylaminopyridine (DMAP, 206 mg, 1.69 mmol) was added and the solution was chilled to 0° C. N-Boc-ethylenediamine (811 mg, 800 ul, 5.06 mmol) and 1-ethyl-3-(3-dimethylaminopropyl)carbodiimide (EDCI, 971 mg, 5.06 mmol) were added portion-wise and the reaction mixture was allowed to warm to rt and stirred for 5 h. The reaction mixture was diluted with dichloromethane, extracted with 5% citric acid and saturated sodium bicarbonate solution and the organic layer was dried over Na$_2$SO$_4$. The solvent was evaporated and compound S7a (882 mg, 90%) could be used without further purification for the next step. R$_f$ (CH$_2$C$_{12}$/MeOH, 9/1): 0.50; $^1$H-NMR (400 MHz, d$_6$-DMSO): δ 9.11 (s, 1H), 8.88 (t, J=5.2 Hz, 1H), 8.37-8.40 (m, 1H), 8.14-8.19 (M, 1H), 6.93 (t, J=5.6 Hz, 1H), 3.30-3.33 (m, 2H), 3.11-3.18 (m, 2H), 1.37 (s, 9H) ppm; $^{13}$C-NMR (400 MHz, d$_6$-DMSO): δ 163.50 (C), 155.70 (C), 149.79 (CH), 136.61 (CH), 134.12 (C), 133.01 (C), 128.75 (CH), 117.12 (C), 77.66 (C), 39.92 (CH$_2$), 39.71 (CH$_2$), 28.18 (3×CH$_3$) ppm; ESI-MS (m/z): [M+H]$^+$ calcd for C$_{14}$H$_{18}$N$_4$O$_3$ 290.14, found 290.5.

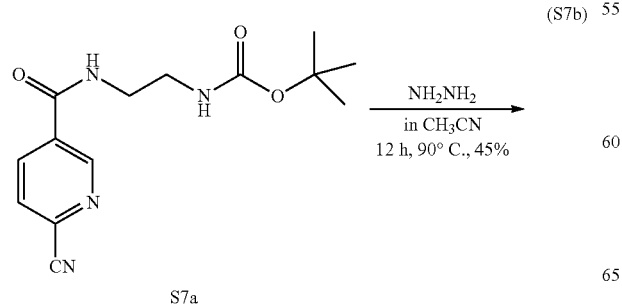
S7a (S7b)

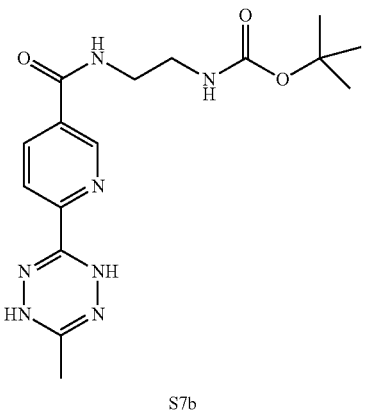
S7b

A dry round-bottom flask was charged with compound S7a (150 mg, 0.52 mmol) and 64% hydrazine hydrate (130 ul, 2.58 mmol) in dry acetonitrile (2 ml). The flask was fitted with a reflux condenser, and the mixture was heated to 90° C. for 12 h behind a blast shield. The reaction mixture was allowed to cool to room temperature, the solvents were evaporated, the residue was dissolved in dichloromethane and extracted with 5% citric acid and saturated sodium bicarbonate solution. The organic layer was dried over sodium sulfate and concentrated under vacuum to dryness to afford compound S7b (84 mg, 45%) in sufficient purity for the next step. R$_f$ (CH$_2$C$_{12}$/MeOH, 94/6): 0.50; $^1$H-NMR (400 MHz, d$_6$-DMSO): δ 9.04 (s, 1H), 8.82 (t, J=5.2 Hz, 1H), 8.31 (d, J=8.0, 1H), 8.04 (d, J=8.0, 1H), 7.00 (m, 1H), 3.36 (m, 2H), 3.18 (m, 2H), 1.87 (s, 3H), 1.42 (s, 9H) ppm; $^{13}$C-NMR (400 MHz, d$_6$-DMSO): δ 164.28 (C), 155.69 (C), 149.43 (C), 147.51 (C), 147.42 (CH), 145.28 (C), 135.99 (CH), 130.61 (C), 120.11 (CH), 77.65 (C), 39.62 (CH$_2$), 39.37 (CH$_2$), 28.19 (3×CH$_3$), 15.60 (CH$_3$) ppm; ESI-MS (m/z): [M+H]$^+$ calcd for C$_{16}$H$_{23}$N$_7$O$_3$ 361.19, found 361.5.

(S8b)

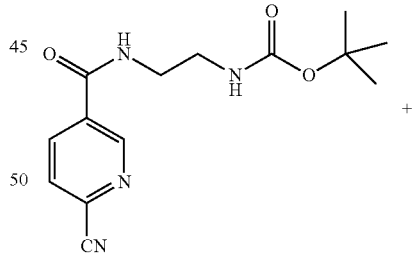
S7a

+

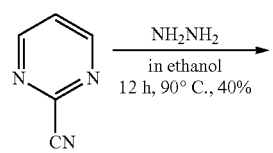

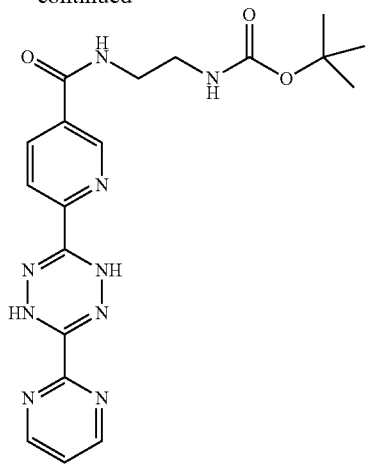

S8b

Equimolar amounts of compound S7a (1.28 g, 4.4 mmol) and pyrimidine-2-carbonitrile (462 mg, 4.4 mmol) were mixed with 64% hydrazine hydrate (1.06 ml, 22.0 mmol) in ethanol (5 ml) and heated for 12 h to 90° C. behind a blast shield. The mixture was allowed to cool to room temperature (rt), the solvents evaporated, the residue dissolved in ethylacetate and extracted with 5% citric acid and saturated sodium bicarbonate solution. The organic layer was dried over $Na_2SO_4$ and evaporated to dryness under vacuum to afford compound S8b (748 mg, 40%) which was deemed pure enough for the subsequent step. $R_f$ ($CH_2C_{12}$/MeOH, 96/4): 0.50; $^1$H-NMR (400 MHz, $d_6$-DMSO): δ 9.24 (s, 1H), 9.12 (s, 1H), 9.09 (m, 1H), 8.99 (d, J=4.8 Hz, 2H), 8.82 (m, 1H), 8.33-8.72 (m, 1H), 8.10 (d, J=8.4 Hz, 1H), 7.68 (t, J=8.4 Hz, 1H), 7.68 (t, J=4.8 Hz, 1H), 6.98 (t, J=5.8 Hz, 1H), 3.25-3.38 (m, 2H), 3.18-3.20 (m, 2H), 1.41 (s, 9H) ppm; $^{13}$C-NMR (400 MHz, $d_6$-DMSO): δ 171.18 (C), 164.25 (C), 157.69 (2×CH), 155.86 (C), 155.70 (C), 148.84 (C), 148.75 (C), 147.52 (CH), 136.19 (CH), 131.15 (C), 122.17 (CH), 120.61 (CH), 77.66 (C), 39.65 ($CH_2$), 39.37 ($CH_2$), 28.19 (3×$CH_3$) ppm; ESI-MS (m/z): [M+H]$^+$ calcd for $C_{19}H_{23}N_9O_3$ 425.19, found 425.5.

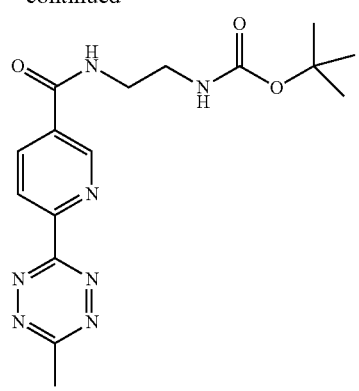

7

To a stirred solution of S7b (75 mg, 0.21 mmol) in acetic acid (3 ml) sodium nitrite (22 mg, 0.31 mmol) was added at rt. After 10 min the reaction mixture was diluted with dichloromethane and extracted several times with a half-saturated sodium bicarbonate solution. The organic layer was dried over $Na_2SO_4$ and the solvent evaporated. Column chromatography on $SiO_2$ (0% to 4% methanol in dichloromethane) afforded 7 as a pink solid (40 mg, 55%). $R_f$ ($CH_2C_{12}$/MeOH, 94/6): 0.40; $^1$H-NMR (400 MHz, $d_6$-DMSO): δ 9.27 (s, 1H), 8.89 (t, J=5.2 Hz, 1H), 8.61 (d, J=8.4 Hz, 1H), 8.46-8.49 (dd, $J_1$=8.4 Hz, $J_2$=2.0 Hz, 1H), 6.97 (t, J=5.8 Hz, 1H) 3.35 (m, 2H), 3.08 (s, 3H), 3.17 (m, 2H), 1.40 (s, 9H) ppm; $^{13}$C-NMR (400 MHz, $d_6$-DMSO): δ 167.61 (C), 164.28 (C), 162.85 (C), 155.73 (C), 152.02 (C), 149.17 (CH), 136.59 (CH), 131.64 (C), 123.28 (CH), 77.67 (C), 39.74 ($CH_2$), 39.37 ($CH_2$), 28.21 (3×$CH_3$), 20.97 ($CH_3$) ppm; ESI-MS (m/z): [M+H]$^+$ calcd for $C_{16}H_{21}N_7O_3$ 359.17, found 359.6.

(7)

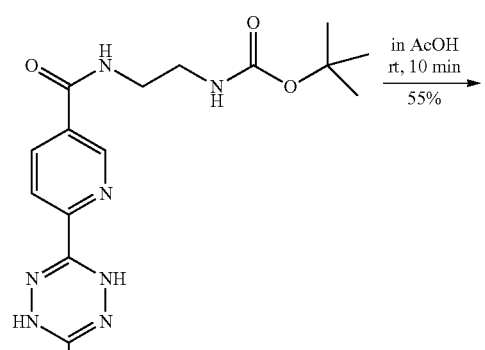

S7b $\xrightarrow{\text{in AcOH} \atop \text{rt, 10 min}}_{55\%}$ (8)

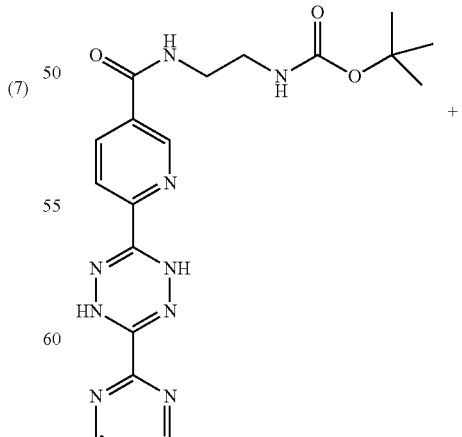

S8b

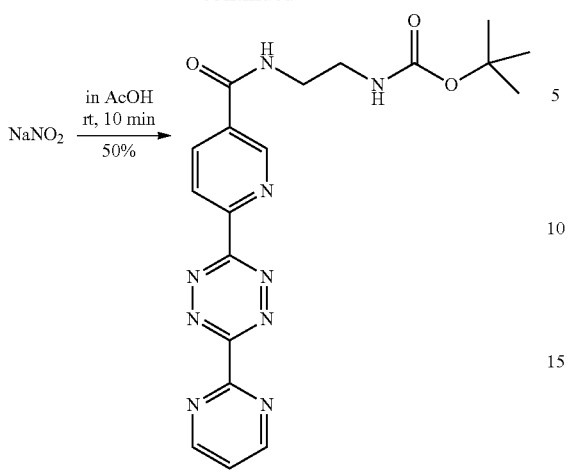

8

To a stirred solution of S8b (200 mg, 0.47 mmol) in acetic acid (10 ml) sodium nitrite (48.6 mg, 0.71 mmol) was added at rt. After 10 min the reaction mixture was diluted with dichloromethane and extracted several times with a half-saturated sodium bicarbonate solution. The organic layer was dried over $Na_2SO_4$ and the solvent evaporated. Column chromatography on $SiO_2$ (0% to 8% methanol in dichloromethane) afforded 8 as a pink solid (100 mg, 50%). $R_f$ ($CH_2C_{12}$/MeOH, 9/1): 0.50; $^1$H-NMR (400 MHz, $d_6$-DMSO): δ 9.38 (d, J=1.2 Hz, 1H), 9.28 (d, J=4.8 Hz, 2H), 8.98-9.01 (t, J=5.4 Hz, 1H), 8.80 (d, J=8.4 Hz, 1H), 8.57-8.59 (dd, $J_1$=8.2 Hz, $J_2$=1.8 Hz, 1H), 7.91-7.93 (t, J=4.8 Hz, 1H), 7.03-7.05 (t, J=5.8 Hz, 1H), 3.43-3.45 (m, 2H), 3.19-3.26 (m, 2H), 1.44 (s, 9H) ppm; $^{13}$C-NMR (400 MHz, $d_6$-DMSO): δ 164.24 (C), 162.94 (2×C), 158.98 (C), 158.54 (2×CH), 155.74 (C), 151.64 (C), 149.34 (CH), 136.67 (CH), 132.16 (C), 124.17 (CH), 123.09 (CH), 77.68 (C), 39.77 ($CH_2$), 39.38 ($CH_2$), 28.22 (3×$CH_3$) ppm; ESI-MS (m/z): [M+H]$^+$ calcd for $C_{19}H_{21}N_9O_3$ 423.18, found 423.5.

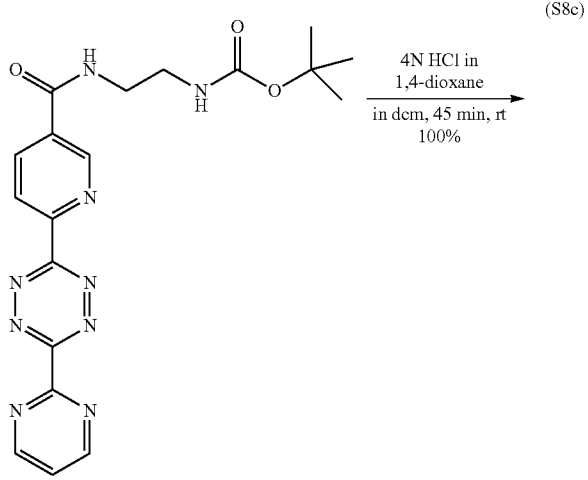

8

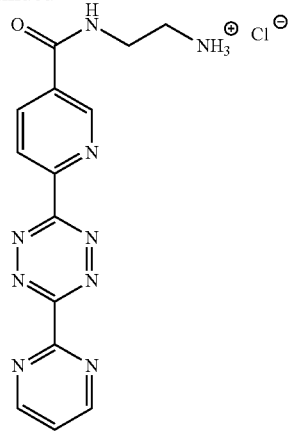

S8c

To a stirred solution of compound 8 (200 mg, 0.47 mmol) in dry dichloromethane (4 ml) a 4N HCl solution in dioxane (2 ml) was added and the reaction mixture was allowed to stir for 45 min at rt, after which time complete consumption of the starting material was observed by LC-MS and TLC analysis. The reaction mixture was concentrated to dryness under reduced pressure, to give compound S8c as HCl salt (170 mg, 100%). The crude material was deemed pure enough for subsequent reactions. $^1$H-NMR (400 MHz, $d_6$-DMSO): δ 9.44 (s, 1H), 9.34-9.37 (t, J=5.2 Hz, 1H), 9.24 (d, J=4.8 Hz, 1H), 8.77 (m, 1H), 8.63-8.67 (m, 1H), 8.24 (s, br, 2H), 7.87-7.89 (t, J=4.8 Hz, 1H), 3.62-3.66 (m, 2H), 3.06-3.09 (m, 2H) ppm; $^{13}$C-NMR (400 MHz, $d_6$-DMSO): δ 164.66 (C), 162.93 (C), 158.95 (C), 158.55 (2×CH), 151.78 (C), 149.59 (CH), 136.90 (CH), 131.68 (C), 124.12 (CH), 124.12 (CH), 123.11 (CH), 66.31 ($CH_2$) ppm; ESI-MS (m/z): [M+H]$^+$ calcd for $C_{14}H_{13}N_9O$ 323.12, found 323.3.

General Procedure for the Synthesis of Tetrazine-Fluorophore Conjugates

To a solution of the succinimidyl ester or the isothiocyanate of the appropriate fluorophore (15 µmol) in anhydrous dmf, the corresponding tetrazine HCl salt S5c, S6c or S8c (30 µmol) and N,N-diisopropylethylamine (45 µmol) were added and the reaction mixture was stirred in the dark. The progress of the reaction was followed by LC-MS and after several hours the reaction was adjudged complete by consumption of the starting material. The solvent was evaporated and the residue dried under vacuum. The product was purified by preparative reverse phase HPLC using a gradient from 20% to 85% of buffer B in buffer A (buffer A: $H_2O$, 0.1% TFA; buffer B: acetonitril, 0.1% TFA). The identity and purity of the conjugates were confirmed by LC-MS (see FIG. 16B and FIG. 17).

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method of producing a polypeptide comprising a Nε-5-norbornene-2-yloxycarbonyl-L-lysine, said method comprising (i) providing a nucleic acid encoding the polypeptide which nucleic acid comprises an orthogonal amber codon (TAG) encoding said Nε-5-norbornene-2-yloxycarbonyl-L-lysine; (ii) translating said nucleic acid in the presence of said Nε-5-norbornene-2-yloxycarbonyl-L-lysine, a MbtRNA$_{CUA}$ and a MbPylRS tRNA synthetase, wherein said MbPylRS tRNA synthetase contains the following amino acid substitutions in SEQ ID NO: 1: L274A, C313S, and M315I, recognizes said MbtRNA$_{CUA}$ and said Nε-5-norbornene-2-yloxycarbonyl-L-lysine and attaches said Nε-5-norbornene-2-yloxycarbonyl-L-lysine acid to said MbtRNA$_{CUA}$ and said MbtRNA$_{CUA}$ recognizes said orthogonal amber codon and incorporates said Nε-5-norbornene-2-yloxycarbonyl-L-lysine into the polypeptide chain at said orthogonal amber codon.

2. A method according to claim 1, wherein said Nε-5-norbornene-2-yloxycarbonyl-L-lysine is incorporated at a position corresponding to a lysine residue in the polypeptide.

3. A method according to claim 1, wherein said Nε-5-norbornene-2-yloxycarbonyl-L-lysine is incorporated at a position corresponding to a serine residue in the polypeptide.

4. A method according to claim 1, wherein said Nε-5-norbornene-2-yloxycarbonyl-L-lysine is incorporated at a position corresponding to an asparagine residue in the polypeptide.

5. A method according to claim 1, wherein said polypeptide contains a single Nε-5-norbornene-2-yloxycarbonyl-L-lysine.

6. A method according to claim 1, wherein said Nε-5-norbornene-2-yloxycarbonyl-L-lysine is joined to a tetrazine group after said Nε-5-norbornene-2-yloxycarbonyl-L-lysine is incorporated into said polypeptide via a reaction between the tetrazine group and norbornene.

7. The method of claim 6, wherein said tetrazine group has a structure selected from the groups consisting of:

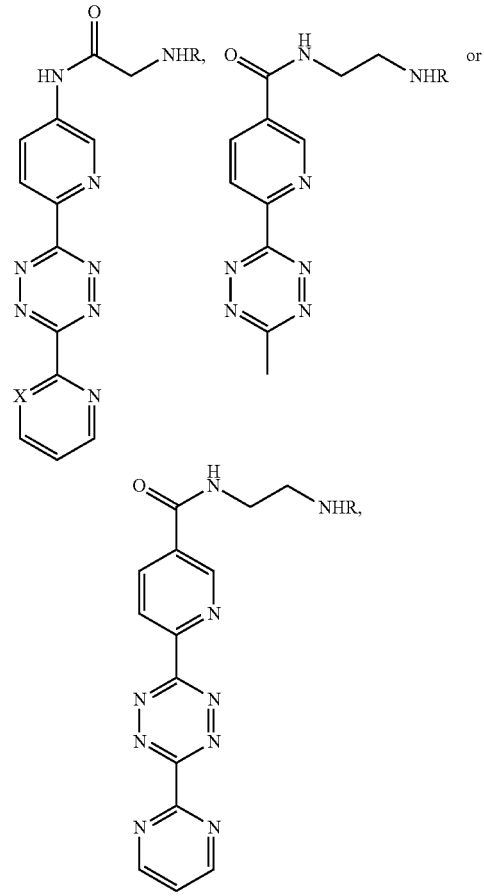

wherein X is CH or N and R is tert-butyloxycarbonyl (Boc).

8. A method according to claim 6, wherein said tetrazine group is further joined to a fluorophore or to a PEG group.

9. A method according to claim 8, wherein said fluorophore comprises fluorescein, tetramethyl rhodamine (TAMRA) or boron-dipyrromethene (BODIPY).

* * * * *

SEQUENCE LISTING

<160> NUMBER OF SEQ ID NOS: 16

<210> SEQ ID NO 1
<211> LENGTH: 419
<212> TYPE: PRT
<213> ORGANISM: Methanosarcina barkeri

<400> SEQUENCE: 1

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Ala Pro Lys Val Lys Ala Met Pro Lys Ser Val Ser
            100                 105                 110

Arg Ala Pro Lys Pro Leu Glu Asn Pro Val Ser Ala Lys Ala Ser Thr
        115                 120                 125

Asp Thr Ser Arg Ser Val Pro Ser Pro Ala Lys Ser Thr Pro Asn Ser
    130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Asp Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Asp Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365
```

```
Pro Val Pro Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 2
<211> LENGTH: 419
<212> TYPE: PRT
<213> ORGANISM: Methanosarcina barkeri

<400> SEQUENCE: 2

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
                100                 105                 110

Arg Ala Pro Lys Pro Leu Glu Asn Ser Val Ser Ala Lys Ala Ser Thr
            115                 120                 125

Asn Thr Ser Arg Ser Val Pro Ser Pro Ala Lys Ser Thr Pro Asn Ser
130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
290                 295                 300

Glu Glu Phe Thr Met Val Asn Phe Cys Gln Met Gly Ser Gly Cys Thr
305                 310                 315                 320
```

-continued

```
Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 3
<211> LENGTH: 454
<212> TYPE: PRT
<213> ORGANISM: Methanosarcina mazeii

<400> SEQUENCE: 3

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270
```

-continued

```
Ile Glu Arg Met Gly Ile Asp Asn Asp Thr Glu Leu Ser Lys Gln Ile
            275                 280                 285

Phe Arg Val Asp Lys Asn Phe Cys Leu Arg Pro Met Leu Ala Pro Asn
        290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 4
<211> LENGTH: 443
<212> TYPE: PRT
<213> ORGANISM: Methanosarcina acetivorans

<400> SEQUENCE: 4

Met Asp Lys Lys Pro Leu Asp Thr Leu Ile Ser Ala Thr Gly Leu Trp
1               5                   10                  15

Met Ser Arg Thr Gly Met Ile His Lys Ile Lys His Glu Val Ser
            20                  25                  30

Arg Ser Lys Ile Tyr Ile Glu Met Ala Cys Gly Glu Arg Leu Val Val
        35                  40                  45

Asn Asn Ser Arg Ser Ser Arg Thr Ala Arg Ala Leu Arg His His Lys
    50                  55                  60

Tyr Arg Lys Thr Cys Arg His Cys Arg Val Ser Asp Glu Asp Ile Asn
65                  70                  75                  80

Asn Phe Leu Thr Lys Thr Ser Glu Glu Lys Thr Thr Val Lys Val Lys
                85                  90                  95

Val Val Ser Ala Pro Arg Val Arg Lys Ala Met Pro Lys Ser Val Ala
            100                 105                 110

Arg Ala Pro Lys Pro Leu Glu Ala Thr Ala Gln Val Pro Leu Ser Gly
        115                 120                 125

Ser Lys Pro Ala Pro Ala Thr Pro Val Ser Ala Pro Ala Gln Ala Pro
    130                 135                 140

Ala Pro Ser Thr Gly Ser Ala Ser Ala Thr Ser Ala Ser Ala Gln Arg
145                 150                 155                 160

Met Ala Asn Ser Ala Ala Ala Pro Ala Pro Val Pro Thr Ser Ala
                165                 170                 175

Pro Ala Leu Thr Lys Gly Gln Leu Asp Arg Leu Glu Gly Leu Leu Ser
            180                 185                 190
```

Pro Lys Asp Glu Ile Ser Leu Asp Ser Glu Lys Pro Phe Arg Glu Leu
        195                 200                 205

Glu Ser Glu Leu Leu Ser Arg Arg Lys Lys Asp Leu Lys Arg Ile Tyr
    210                 215                 220

Ala Glu Glu Arg Glu Asn Tyr Leu Gly Lys Leu Glu Arg Glu Ile Thr
225                 230                 235                 240

Lys Phe Phe Val Asp Arg Gly Phe Leu Glu Ile Lys Ser Pro Ile Leu
                245                 250                 255

Ile Pro Ala Glu Tyr Val Glu Arg Met Gly Ile Asn Ser Asp Thr Glu
            260                 265                 270

Leu Ser Lys Gln Val Phe Arg Ile Asp Lys Asn Phe Cys Leu Arg Pro
    275                 280                 285

Met Leu Ala Pro Asn Leu Tyr Asn Tyr Leu Arg Lys Leu Asp Arg Ala
290                 295                 300

Leu Pro Asp Pro Ile Lys Ile Phe Glu Ile Gly Pro Cys Tyr Arg Lys
305                 310                 315                 320

Glu Ser Asp Gly Lys Glu His Leu Glu Glu Phe Thr Met Leu Asn Phe
                325                 330                 335

Cys Gln Met Gly Ser Gly Cys Thr Arg Glu Asn Leu Glu Ala Ile Ile
            340                 345                 350

Thr Glu Phe Leu Asn His Leu Gly Ile Asp Phe Glu Ile Ile Gly Asp
    355                 360                 365

Ser Cys Met Val Tyr Gly Asn Thr Leu Asp Val Met His Asp Asp Leu
370                 375                 380

Glu Leu Ser Ser Ala Val Val Gly Pro Val Pro Leu Asp Arg Glu Trp
385                 390                 395                 400

Gly Ile Asp Lys Pro Trp Ile Gly Ala Gly Phe Gly Leu Glu Arg Leu
                405                 410                 415

Leu Lys Val Met His Gly Phe Lys Asn Ile Lys Arg Ala Ala Arg Ser
            420                 425                 430

Glu Ser Tyr Tyr Asn Gly Ile Ser Thr Asn Leu
    435                 440

<210> SEQ ID NO 5
<211> LENGTH: 478
<212> TYPE: PRT
<213> ORGANISM: Methanosarcina thermophila

<400> SEQUENCE: 5

Met Asp Lys Lys Pro Leu Asn Thr Leu Ile Ser Ala Thr Gly Leu Trp
1               5                   10                  15

Met Ser Arg Thr Gly Lys Leu His Lys Ile Arg His His Glu Val Ser
            20                  25                  30

Lys Arg Lys Ile Tyr Ile Glu Met Glu Cys Gly Glu Arg Leu Val Val
        35                  40                  45

Asn Asn Ser Arg Ser Cys Arg Ala Ala Arg Ala Leu Arg His His Lys
    50                  55                  60

Tyr Arg Lys Ile Cys Lys His Cys Arg Val Ser Asp Glu Asp Leu Asn
65                  70                  75                  80

Lys Phe Leu Thr Arg Thr Asn Glu Asp Lys Ser Asn Ala Lys Val Thr
                85                  90                  95

Val Val Ser Ala Pro Lys Ile Arg Lys Val Met Pro Lys Ser Val Ala
            100                 105                 110

Arg Thr Pro Lys Pro Leu Glu Asn Thr Ala Pro Val Gln Thr Leu Pro

```
            115                 120                 125
Ser Glu Ser Gln Pro Ala Pro Thr Thr Pro Ile Ser Ala Ser Thr Thr
    130                 135                 140

Ala Pro Ala Ser Thr Ser Thr Thr Ala Pro Ala Pro Ala Ser Thr Thr
145                 150                 155                 160

Ala Pro Ala Pro Ala Ser Thr Thr Ala Pro Ala Ser Ala Ser Thr Thr
                165                 170                 175

Ile Ser Thr Ser Ala Met Pro Ala Ser Thr Ser Ala Gln Gly Thr Thr
            180                 185                 190

Lys Phe Asn Tyr Ile Ser Gly Gly Phe Pro Arg Pro Ile Pro Val Gln
        195                 200                 205

Ala Ser Ala Pro Ala Leu Thr Lys Ser Gln Ile Asp Arg Leu Gln Gly
    210                 215                 220

Leu Leu Ser Pro Lys Asp Glu Ile Ser Leu Asp Ser Gly Thr Pro Phe
225                 230                 235                 240

Arg Lys Leu Glu Ser Glu Leu Leu Ser Arg Arg Lys Asp Leu Lys
                245                 250                 255

Gln Ile Tyr Ala Glu Glu Arg Glu His Tyr Leu Gly Lys Leu Glu Arg
            260                 265                 270

Glu Ile Thr Lys Phe Phe Val Asp Arg Gly Phe Leu Glu Ile Lys Ser
        275                 280                 285

Pro Ile Leu Ile Pro Met Glu Tyr Ile Glu Arg Met Gly Ile Asp Asn
    290                 295                 300

Asp Lys Glu Leu Ser Lys Gln Ile Phe Arg Val Asp Asn Asn Phe Cys
305                 310                 315                 320

Leu Arg Pro Met Leu Ala Pro Asn Leu Tyr Asn Tyr Leu Arg Lys Leu
                325                 330                 335

Asn Arg Ala Leu Pro Asp Pro Ile Lys Ile Phe Glu Ile Gly Pro Cys
            340                 345                 350

Tyr Arg Lys Glu Ser Asp Gly Lys Glu His Leu Glu Glu Phe Thr Met
        355                 360                 365

Leu Asn Phe Cys Gln Met Gly Ser Gly Cys Thr Arg Glu Asn Leu Glu
    370                 375                 380

Ala Ile Ile Lys Asp Phe Leu Asp Tyr Leu Gly Ile Asp Phe Glu Ile
385                 390                 395                 400

Val Gly Asp Ser Cys Met Val Tyr Gly Asp Thr Leu Asp Val Met His
                405                 410                 415

Gly Asp Leu Glu Leu Ser Ser Ala Val Val Gly Pro Val Pro Met Asp
            420                 425                 430

Arg Asp Trp Gly Ile Asn Lys Pro Trp Ile Gly Ala Gly Phe Gly Leu
        435                 440                 445

Glu Arg Leu Leu Lys Val Met His Asn Phe Lys Asn Ile Lys Arg Ala
    450                 455                 460

Ser Arg Ser Glu Ser Tyr Tyr Asn Gly Ile Ser Thr Asn Leu
465                 470                 475

<210> SEQ ID NO 6
<211> LENGTH: 416
<212> TYPE: PRT
<213> ORGANISM: Methanococcoides burtonii

<400> SEQUENCE: 6

Met Glu Lys Gln Leu Leu Asp Val Leu Val Glu Leu Asn Gly Val Trp
1               5                   10                  15
```

Leu Ser Arg Ser Gly Leu Leu His Gly Ile Arg Asn Phe Glu Ile Thr
            20                  25                  30

Thr Lys His Ile His Ile Glu Thr Asp Cys Gly Ala Arg Phe Thr Val
        35                  40                  45

Arg Asn Ser Arg Ser Ser Arg Ser Ala Arg Ser Leu Arg His Asn Lys
    50                  55                  60

Tyr Arg Lys Pro Cys Lys Arg Cys Arg Pro Ala Asp Glu Gln Ile Asp
65                  70                  75                  80

Arg Phe Val Lys Lys Thr Phe Lys Glu Lys Arg Gln Thr Val Ser Val
                85                  90                  95

Phe Ser Ser Pro Lys Lys His Val Pro Lys Lys Pro Lys Val Ala Val
            100                 105                 110

Ile Lys Ser Phe Ser Ile Ser Thr Pro Ser Pro Lys Glu Ala Ser Val
        115                 120                 125

Ser Asn Ser Ile Pro Thr Pro Ser Ile Ser Val Val Lys Asp Glu Val
    130                 135                 140

Lys Val Pro Glu Val Lys Tyr Thr Pro Ser Gln Ile Glu Arg Leu Lys
145                 150                 155                 160

Thr Leu Met Ser Pro Asp Asp Lys Ile Pro Ile Gln Asp Glu Leu Pro
                165                 170                 175

Glu Phe Lys Val Leu Glu Lys Glu Leu Ile Gln Arg Arg Arg Asp Asp
            180                 185                 190

Leu Lys Lys Met Tyr Glu Glu Asp Arg Glu Asp Arg Leu Gly Lys Leu
        195                 200                 205

Glu Arg Asp Ile Thr Glu Phe Phe Val Asp Arg Gly Phe Leu Glu Ile
    210                 215                 220

Lys Ser Pro Ile Met Ile Pro Phe Glu Tyr Ile Glu Arg Met Gly Ile
225                 230                 235                 240

Asp Lys Asp Asp His Leu Asn Lys Gln Ile Phe Arg Val Asp Glu Ser
                245                 250                 255

Met Cys Leu Arg Pro Met Leu Ala Pro Cys Leu Tyr Asn Tyr Leu Arg
            260                 265                 270

Lys Leu Asp Lys Val Leu Pro Asp Pro Ile Arg Ile Phe Glu Ile Gly
        275                 280                 285

Pro Cys Tyr Arg Lys Glu Ser Asp Gly Ser Ser His Leu Glu Glu Phe
    290                 295                 300

Thr Met Val Asn Phe Cys Gln Met Gly Ser Gly Cys Thr Arg Glu Asn
305                 310                 315                 320

Met Glu Ala Leu Ile Asp Glu Phe Leu Glu His Leu Gly Ile Glu Tyr
                325                 330                 335

Glu Ile Glu Ala Asp Asn Cys Met Val Tyr Gly Asp Thr Ile Asp Ile
            340                 345                 350

Met His Gly Asp Leu Glu Leu Ser Ser Ala Val Val Gly Pro Ile Pro
        355                 360                 365

Leu Asp Arg Glu Trp Gly Val Asn Lys Pro Trp Met Gly Ala Gly Phe
    370                 375                 380

Gly Leu Glu Arg Leu Leu Lys Val Arg His Asn Tyr Thr Asn Ile Arg
385                 390                 395                 400

Arg Ala Ser Arg Ser Glu Leu Tyr Tyr Asn Gly Ile Asn Thr Asn Leu
                405                 410                 415

<210> SEQ ID NO 7
<211> LENGTH: 279
<212> TYPE: PRT

<213> ORGANISM: Desulfitobacterium hafniense

<400> SEQUENCE: 7

Met Ser Ser Phe Trp Thr Lys Val Gln Tyr Gln Arg Leu Lys Glu Leu
1               5                   10                  15

Asn Ala Ser Gly Glu Gln Leu Glu Met Gly Phe Ser Asp Ala Leu Ser
            20                  25                  30

Arg Asp Arg Ala Phe Gln Gly Ile Glu His Gln Leu Met Ser Gln Gly
        35                  40                  45

Lys Arg His Leu Glu Gln Leu Arg Thr Val Lys His Arg Pro Ala Leu
    50                  55                  60

Leu Glu Leu Glu Gly Leu Ala Lys Ala Leu His Gln Gln Gly Phe
65                  70                  75                  80

Val Gln Val Val Thr Pro Thr Ile Ile Thr Lys Ser Ala Leu Ala Lys
                85                  90                  95

Met Thr Ile Gly Glu Asp His Pro Leu Phe Ser Gln Val Phe Trp Leu
            100                 105                 110

Asp Gly Lys Lys Cys Leu Arg Pro Met Leu Ala Pro Asn Leu Tyr Thr
        115                 120                 125

Leu Trp Arg Glu Leu Glu Arg Leu Trp Asp Lys Pro Ile Arg Ile Phe
    130                 135                 140

Glu Ile Gly Thr Cys Tyr Arg Lys Glu Ser Gln Gly Ala Gln His Leu
145                 150                 155                 160

Asn Glu Phe Thr Met Leu Asn Leu Thr Glu Leu Gly Thr Pro Leu Glu
                165                 170                 175

Glu Arg His Gln Arg Leu Glu Asp Met Ala Arg Trp Val Leu Glu Ala
            180                 185                 190

Ala Gly Ile Arg Glu Phe Glu Leu Val Thr Glu Ser Ser Val Val Tyr
        195                 200                 205

Gly Asp Thr Val Asp Val Met Lys Gly Asp Leu Glu Leu Ala Ser Gly
    210                 215                 220

Ala Met Gly Pro His Phe Leu Asp Glu Lys Trp Glu Ile Val Asp Pro
225                 230                 235                 240

Trp Val Gly Leu Gly Phe Gly Leu Glu Arg Leu Leu Met Ile Arg Glu
                245                 250                 255

Gly Thr Gln His Val Gln Ser Met Ala Arg Ser Leu Ser Tyr Leu Asp
            260                 265                 270

Gly Val Arg Leu Asn Ile Asn
        275

<210> SEQ ID NO 8
<211> LENGTH: 312
<212> TYPE: PRT
<213> ORGANISM: Desulfitobacterium hafniense

<400> SEQUENCE: 8

Met Asp Arg Ile Asp His Thr Asp Ser Lys Phe Val Gln Ala Gly Glu
1               5                   10                  15

Thr Pro Val Leu Pro Ala Thr Phe Met Phe Leu Thr Arg Arg Asp Pro
            20                  25                  30

Pro Leu Ser Ser Phe Trp Thr Lys Val Gln Tyr Gln Arg Leu Lys Glu
        35                  40                  45

Leu Asn Ala Ser Gly Glu Gln Leu Glu Met Gly Phe Ser Asp Ala Leu
    50                  55                  60

Ser Arg Asp Arg Ala Phe Gln Gly Ile Glu His Gln Leu Met Ser Gln

```
                65                  70                  75                  80
        Gly Lys Arg His Leu Glu Gln Leu Arg Thr Val Lys His Arg Pro Ala
                            85                  90                  95

Leu Leu Glu Leu Glu Glu Gly Leu Ala Lys Ala Leu His Gln Gln Gly
                        100                 105                 110

Phe Val Gln Val Val Thr Pro Thr Ile Ile Thr Lys Ser Ala Leu Ala
                        115                 120                 125

Lys Met Thr Ile Gly Glu Asp His Pro Leu Phe Ser Gln Val Phe Trp
                    130                 135                 140

Leu Asp Gly Lys Lys Cys Leu Arg Pro Met Leu Ala Pro Asn Leu Tyr
        145                 150                 155                 160

Thr Leu Trp Arg Glu Leu Glu Arg Leu Trp Asp Lys Pro Ile Arg Ile
                            165                 170                 175

Phe Glu Ile Gly Thr Cys Tyr Arg Lys Glu Ser Gln Gly Ala Gln His
                        180                 185                 190

Leu Asn Glu Phe Thr Met Leu Asn Leu Thr Glu Leu Gly Thr Pro Leu
                    195                 200                 205

Glu Glu Arg His Gln Arg Leu Glu Asp Met Ala Arg Trp Val Leu Glu
                210                 215                 220

Ala Ala Gly Ile Arg Glu Phe Glu Leu Val Thr Glu Ser Ser Val Val
        225                 230                 235                 240

Tyr Gly Asp Thr Val Asp Val Met Lys Gly Asp Leu Glu Leu Ala Ser
                            245                 250                 255

Gly Ala Met Gly Pro His Phe Leu Asp Glu Lys Trp Glu Ile Val Asp
                        260                 265                 270

Pro Trp Val Gly Leu Gly Phe Gly Leu Glu Arg Leu Leu Met Ile Arg
                    275                 280                 285

Glu Gly Thr Gln His Val Gln Ser Met Ala Arg Ser Leu Ser Tyr Leu
                290                 295                 300

Asp Gly Val Arg Leu Asn Ile Asn
        305                 310

<210> SEQ ID NO 9
        <211> LENGTH: 288
        <212> TYPE: PRT
        <213> ORGANISM: Desulfitobacterium hafniense

<400> SEQUENCE: 9

Met Phe Leu Thr Arg Arg Asp Pro Pro Leu Ser Ser Phe Trp Thr Lys
        1               5                   10                  15

Val Gln Tyr Gln Arg Leu Lys Glu Leu Asn Ala Ser Gly Glu Gln Leu
                        20                  25                  30

Glu Met Gly Phe Ser Asp Ala Leu Ser Arg Asp Arg Ala Phe Gln Gly
                    35                  40                  45

Ile Glu His Gln Leu Met Ser Gln Gly Lys Arg His Leu Glu Gln Leu
                50                  55                  60

Arg Thr Val Lys His Arg Pro Ala Leu Leu Glu Leu Glu Glu Lys Leu
        65                  70                  75                  80

Ala Lys Ala Leu His Gln Gln Gly Phe Val Gln Val Val Thr Pro Thr
                            85                  90                  95

Ile Ile Thr Lys Ser Ala Leu Ala Lys Met Thr Ile Gly Glu Asp His
                        100                 105                 110

Pro Leu Phe Ser Gln Val Phe Trp Leu Asp Gly Lys Lys Cys Leu Arg
                    115                 120                 125
```

```
Pro Met Leu Ala Pro Asn Leu Tyr Thr Leu Trp Arg Glu Leu Glu Arg
    130                 135                 140

Leu Trp Asp Lys Pro Ile Arg Ile Phe Glu Ile Gly Thr Cys Tyr Arg
145                 150                 155                 160

Lys Glu Ser Gln Gly Ala Gln His Leu Asn Glu Phe Thr Met Leu Asn
                165                 170                 175

Leu Thr Glu Leu Gly Thr Pro Leu Glu Glu Arg His Gln Arg Leu Glu
            180                 185                 190

Asp Met Ala Arg Trp Val Leu Glu Ala Ala Gly Ile Arg Glu Phe Glu
                195                 200                 205

Leu Val Thr Glu Ser Ser Val Val Tyr Gly Asp Thr Val Asp Val Met
    210                 215                 220

Lys Gly Asp Leu Glu Leu Ala Ser Gly Ala Met Gly Pro His Phe Leu
225                 230                 235                 240

Asp Glu Lys Trp Glu Ile Phe Asp Pro Trp Val Gly Leu Gly Phe Gly
                245                 250                 255

Leu Glu Arg Leu Leu Met Ile Arg Glu Gly Thr Gln His Val Gln Ser
            260                 265                 270

Met Ala Arg Ser Leu Ser Tyr Leu Asp Gly Val Arg Leu Asn Ile Asn
            275                 280                 285

<210> SEQ ID NO 10
<211> LENGTH: 277
<212> TYPE: PRT
<213> ORGANISM: Desulfotomaculum acetoxidans

<400> SEQUENCE: 10

Met Ser Phe Leu Trp Thr Val Ser Gln Gln Lys Arg Leu Ser Glu Leu
1               5                   10                  15

Asn Ala Ser Glu Glu Lys Asn Met Ser Phe Ser Thr Ser Asp
                20                  25                  30

Arg Glu Ala Ala Tyr Lys Arg Val Glu Met Arg Leu Ile Asn Glu Ser
            35                  40                  45

Lys Gln Arg Leu Asn Lys Leu Arg His Glu Thr Arg Pro Ala Ile Cys
    50                  55                  60

Ala Leu Glu Asn Arg Leu Ala Ala Leu Arg Gly Ala Gly Phe Val
65                  70                  75                  80

Gln Val Ala Thr Pro Val Ile Leu Ser Lys Lys Leu Leu Gly Lys Met
                85                  90                  95

Thr Ile Thr Asp Glu His Ala Leu Phe Ser Gln Val Phe Trp Ile Glu
            100                 105                 110

Glu Asn Lys Cys Leu Arg Pro Met Leu Ala Pro Asn Leu Tyr Tyr Ile
        115                 120                 125

Leu Lys Asp Leu Leu Arg Leu Trp Glu Lys Pro Val Arg Ile Phe Glu
    130                 135                 140

Ile Gly Ser Cys Phe Arg Lys Glu Ser Gln Gly Ser Asn His Leu Asn
145                 150                 155                 160

Glu Phe Thr Met Leu Asn Leu Val Glu Trp Gly Leu Pro Glu Glu Gln
                165                 170                 175

Arg Gln Lys Arg Ile Ser Glu Leu Ala Lys Leu Val Met Asp Glu Thr
            180                 185                 190

Gly Ile Asp Glu Tyr His Leu Glu His Ala Glu Ser Val Val Tyr Gly
        195                 200                 205

Glu Thr Val Asp Val Met His Arg Asp Ile Glu Leu Gly Ser Gly Ala
    210                 215                 220
```

```
Leu Gly Pro His Phe Leu Asp Gly Arg Trp Gly Val Gly Pro Trp
225                 230                 235                 240

Val Gly Ile Gly Phe Gly Leu Glu Arg Leu Leu Met Val Glu Gln Gly
            245                 250                 255

Gly Gln Asn Val Arg Ser Met Gly Lys Ser Leu Thr Tyr Leu Asp Gly
        260                 265                 270

Val Arg Leu Asn Ile
        275

<210> SEQ ID NO 11
<211> LENGTH: 419
<212> TYPE: PRT
<213> ORGANISM: Artificial Sequence
<220> FEATURE:
<223> OTHER INFORMATION: Mutant Synthetase

<400> SEQUENCE: 11

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
50                  55                  60

Tyr Arg Lys Thr Cys Lys Arg Cys Arg Val Ser Gly Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
            245                 250                 255

Asp Lys Asn Leu Cys Leu Arg Pro Met Val Ala Pro Thr Ile Phe Asn
        260                 265                 270

Tyr Ala Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300
```

Glu Phe Thr Met Val Asn Phe Phe Gln Met Gly Ser Gly Cys Thr
305                 310                 315                 320

Arg Glu Asn Leu Glu Ala Leu Ile Lys Glu Phe Leu Asp Tyr Leu Glu
            325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
            355                 360                 365

Pro Val Ser Leu Asp Arg Glu Trp Gly Ile Asp Lys Pro Trp Ile Gly
370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
            405                 410                 415

Thr Asn Leu

<210> SEQ ID NO 12
<211> LENGTH: 419
<212> TYPE: PRT
<213> ORGANISM: Artificial Sequence
<220> FEATURE:
<223> OTHER INFORMATION: Mutant Synthetase

<400> SEQUENCE: 12

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
            85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
            165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

```
Phe Gly Ile Asn Asn Asp Thr Glu Leu Ser Lys Gln Ile Phe Arg Val
                245                 250                 255

Asp Lys Asn Leu Cys Leu Arg Pro Met Leu Ser Pro Thr Leu Cys Asn
            260                 265                 270

Tyr Met Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 13
<211> LENGTH: 454
<212> TYPE: PRT
<213> ORGANISM: Artificial Sequence
<220> FEATURE:
<223> OTHER INFORMATION: Mutant Synthetase

<400> SEQUENCE: 13

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
```

```
            180                 185                 190
Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Val Ala Pro Asn
    290                 295                 300

Ile Phe Asn Tyr Ala Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Phe Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 14
<211> LENGTH: 454
<212> TYPE: PRT
<213> ORGANISM: Artificial Sequence
<220> FEATURE:
<223> OTHER INFORMATION: Mutant Synthetase

<400> SEQUENCE: 14

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
```

```
                    85                  90                  95
Val Val Ser Ala Pro Thr Arg Thr Lys Lys Ala Met Pro Lys Ser Val
                100                 105                 110

Ala Arg Ala Pro Lys Pro Leu Glu Asn Thr Glu Ala Ala Gln Ala Gln
                115                 120                 125

Pro Ser Gly Ser Lys Phe Ser Pro Ala Ile Pro Val Ser Thr Gln Glu
                130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
                180                 185                 190

Ser Gln Thr Asp Arg Leu Glu Val Leu Leu Asn Pro Lys Asp Glu Ile
                195                 200                 205

Ser Leu Asn Ser Gly Lys Pro Phe Arg Glu Leu Glu Ser Glu Leu Leu
                210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
                260                 265                 270

Ile Glu Arg Phe Gly Ile Asp Asn Asp Thr Glu Leu Ser Lys Gln Ile
                275                 280                 285

Phe Arg Val Asp Lys Asn Phe Cys Leu Arg Pro Met Leu Ser Pro Asn
                290                 295                 300

Leu Cys Asn Tyr Met Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
                340                 345                 350

Gly Cys Thr Arg Glu Asn Leu Glu Ser Ile Ile Thr Asp Phe Leu Asn
                355                 360                 365

His Leu Gly Ile Asp Phe Lys Ile Val Gly Asp Ser Cys Met Val Tyr
                370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
                420                 425                 430

Asp Phe Lys Asn Ile Lys Arg Ala Ala Arg Ser Glu Ser Tyr Tyr Asn
                435                 440                 445

Gly Ile Ser Thr Asn Leu
    450
```

<210> SEQ ID NO 15
<211> LENGTH: 47
<212> TYPE: DNA
<213> ORGANISM: Artificial Sequence
<220> FEATURE:
<223> OTHER INFORMATION: primer

```
<400> SEQUENCE: 15
accagggtct cgatgcatag aaaaccggac tgaaggagct gcccatg                    47

<210> SEQ ID NO 16
<211> LENGTH: 45
<212> TYPE: DNA
<213> ORGANISM: Artificial Sequence
<220> FEATURE:
<223> OTHER INFORMATION: primer

<400> SEQUENCE: 16
ttgcaggtct ctgcatcata gttagataag actgctaagg catag                     45
```